(12) United States Patent
Coleman et al.

(10) Patent No.: US 10,046,126 B2
(45) Date of Patent: Aug. 14, 2018

(54) APPARATUS AND METHOD FOR DELIVERING FLUIDS AND/OR GASES TO THE LUNGS

(71) Applicant: Suspended Animation, Inc., Rancho Santa Margarita, CA (US)

(72) Inventors: Nathan John Coleman, Murrieta, CA (US); Philip P. Morello, Costa Mesa, CA (US)

(73) Assignee: Suspended Animation, Inc., Rancho Santa Margarita, CA (US)

( * ) Notice: Subject to any disclaimer, the term of this patent is extended or adjusted under 35 U.S.C. 154(b) by 0 days.

(21) Appl. No.: 15/498,429

(22) Filed: Apr. 26, 2017

(65) Prior Publication Data

US 2017/0312123 A1  Nov. 2, 2017

Related U.S. Application Data

(60) Provisional application No. 62/328,526, filed on Apr. 27, 2016.

(51) Int. Cl.
| | |
|---|---|
| *A61M 16/00* | (2006.01) |
| *A61M 16/20* | (2006.01) |
| *A61F 7/12* | (2006.01) |
| *A61M 31/00* | (2006.01) |
| *A61M 16/04* | (2006.01) |
| *A61F 5/37* | (2006.01) |
| *A61F 7/00* | (2006.01) |

(52) U.S. Cl.
CPC ........... *A61M 16/0054* (2013.01); *A61F 5/37* (2013.01); *A61F 7/12* (2013.01); *A61M 16/04* (2013.01); *A61M 16/201* (2014.02); *A61M 31/00* (2013.01); *A61F 2007/0069* (2013.01); *A61F 2007/126* (2013.01); *A61M 2016/0027* (2013.01); *A61M 2202/02* (2013.01); *A61M 2202/04* (2013.01); *A61M 2205/366* (2013.01)

(58) Field of Classification Search
CPC A61M 16/0054; A61M 16/14–16/147; A61M 16/201
See application file for complete search history.

(56) References Cited

U.S. PATENT DOCUMENTS

| | | | | |
|---|---|---|---|---|
| 4,676,232 | A | * | 6/1987 | Olsson ................. A61H 9/0078 601/106 |
| 5,335,650 | A | * | 8/1994 | Shaffer ............. A61M 16/0054 128/200.24 |
| 5,437,272 | A | * | 8/1995 | Fuhrman ........... A61M 16/0054 128/203.12 |
| 5,540,225 | A | * | 7/1996 | Schutt .................. A61K 9/0026 128/207.15 |
| 5,706,830 | A | * | 1/1998 | Parker ............... A61M 16/0054 128/203.12 |
| 6,041,777 | A | * | 3/2000 | Faithfull ........... A61M 16/0054 128/200.24 |
| 6,694,977 | B1 | * | 2/2004 | Federowicz .............. A61F 7/12 128/201.13 |

(Continued)

*Primary Examiner* — Valerie L Woodward
(74) *Attorney, Agent, or Firm* — Buchalter

(57) ABSTRACT

An apparatus and method for providing heat exchange in the lungs of the mammal during partial liquid ventilation are provided. The apparatus and method can control delivery and removal of partial liquid ventilation to the lungs of a mammal by responding to pressure change in the lungs to minimize danger of causing barotrauma to the patient.

20 Claims, 28 Drawing Sheets

(56) References Cited

U.S. PATENT DOCUMENTS

| | | | | |
|---|---|---|---|---|
| 7,726,311 B2* | 6/2010 | Robert | ............... | A61M 1/1068 |
| | | | | 128/204.21 |
| 2010/0012122 A1* | 1/2010 | Shaffer | ............ | A61M 16/0054 |
| | | | | 128/204.18 |

* cited by examiner

FIG. 8B

| AUTOPULSE STATE | → | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|
| | | | | | | | | | | | REDUNDANT → OF 9 | | | | | | | | | | P | V | P | V |
| OFF | 0 | 0 | 0 | 0 | 0 | PRES | PRES | 18V | VAC° | ? | VAC | 18V | 18V | | 18V | 1 | | | 0 | 0 | 0 | 0 | 0 | 0 |
| COMPR | .375 | 18V | PRES | 0 | 18V | PRES | PRES | 18V | VAC° | PRES° | PRES | 18V | 18V | | 18V | VAC | VAC | PRES | 18V | 0 | 18V | 0V | 0 | 0 |
| RELAX | .750 | 18V | 18V | 18V | 18V | VAC | OT↓ VAC | 18V | OT↓ PRES | VAC | PRES | 18V | 18V | | 18V | PRES | PRES | VAC | 0 | 18V | OT 0V | OT 0V | OT 0V | OT 0V |
| COMPR | 1.125 | 18V | PRES | 0 | 18V | PRES | PRES | 18V | VAC | PRES° | VAC | 18V | 18V | | 18V | VAC | VAC | PRES | 18V | 0 | 18V | 0V | 0 | 18V |
| RELAX | 1.500 | 18V | VAC | 18V | 0V | VAC | OT↓ VAC | 18V | OT↓ PRES | VAC | PRES | 18V | 18V | | 18V | PRES | PRES | VAC | 0 | 18V | OT 0V | OT 18V | OT 0V | OT 0V |
| COMPR | 1.875 | | | | | | | | | | | | | | | | | | | | | | | |
| RELAX | 2.250 | | | | | | | | | | | | | | | | | | | | | | | |

810
820
830

APPARATUS AND METHOD FOR DELIVERING FLUIDS AND/OR GASES TO THE LUNGS

PRIORITY

This application claims priority to U.S. Provisional Application No. 62/328,526, filed Apr. 27, 2016, titled "Apparatus and Method for Delivering Fluids and/or Gases to the Lungs," which is incorporated by reference in its entirety herein.

BACKGROUND

Ventilators are machines that support breathing by providing air or oxygen into the lungs. Some ventilators may supply an oxygen-rich liquid, such as a perfluorocarbon (PFC), to an air-breathing organism. Partial liquid ventilation ("PLV") can involve infusing the lungs with a liquid, such as a perfluorocarbon (PFC) and/or gases while mechanical ventilation is provided with a standard ventilator.

There are situations in both human and veterinary medicine where it is desirable to rapidly reverse hyperthermia. Specifically, there are clinical situations where it can be important to be able to rapidly reduce dangerously elevated body temperature of the patient to near normal to reverse hyperthermia from heat stroke, drug or surgical anesthetic reaction, and febrile illness secondary to stroke, infection or other illness. Temperature reduction following events such as trauma, stroke, and heart attack can prolong patient viability by a reduction in metabolic rate. There are situations in both human and veterinary medicine where it is desirable to preserve the life of living tissue, organs or the entire mammal body by reduction in temperature and thus metabolic rate. Liquid ventilation can use the lungs as heat exchangers by pumping a chilled liquid and gas mixture into the lungs and, in turn cooling the blood as it flows through the lung tissue. The lungs have a very large surface area and have many blood vessels spread through them, making them very effective for both gas exchange and heat exchange.

SUMMARY

This following disclosure relates to methods and apparatuses for providing heat exchange to the lungs and/or support of life via ventilation. Some embodiments of the disclosure relate to methods and apparatuses of providing heat exchange to the lungs of a mammal during partial liquid ventilation.

U.S. Pat. No. 8,465,535 to Harris, et al discloses a PLV apparatus that can be used for the heat exchange in the lungs of a mammal. However, one aspect of certain embodiments of the disclosure is the recognition that the disclosed device of U.S. Pat. No. 8,465,535 is bulky and heavy, requiring an assembly of pumps for various parts of the flow of the liquid and multiple reservoirs for volume-measured delivery of the liquid. In addition, one aspect of certain embodiments of the disclosure is the recognition that although the liquid in the device disclosed in U.S. Pat. No. 8,465,535 is cooled before leaving the reservoirs, the liquid may warm up again by the ambient air during its travel in the tube assembly before entering an endotracheal tube, leading to less efficient heat exchange.

Another aspect of certain embodiments of the disclosure is the recognition that PLV devices are not adaptive to pressure change in a patient's lungs due to a cardiopulmonary resuscitation (CPR) procedure or to the patient's own breathing which can make them dangerous to use. In other words, Applicant has recognized that prior PLV devices can continue filling the lungs of the patient even when pressure in the patient's airway has reached a threshold level, which can cause physical damage to the airway due to excessively high pressure, and that volumetric extraction may create excessive negative pressure in the thoracic cavity either by accumulation of small fluid accounting error during the procedure, or the common leakage of breathing fluid past the endotracheal tube cuff for which the volumetric ventilator is not equipped to account. Such excessive negative pressure can result in patient harm. Another aspect of certain embodiments of the disclosure is the recognition that volumetric ventilation devices also cannot exploit the "deep breath" cycle that is available in automated CPR and taught to practitioners of manual CPR.

Another aspect of certain embodiments of the disclosure is the recognition that pressure based PLV or LV when used as a heating or cooling device adapts to the individual patient and situation to maximize heat transfer while preventing potential patient harm. Another aspect of certain embodiments of the disclosure is the recognition that pressure based PLV or LV when used in resuscitation can be configured to enhance blood flow from chest compressions by momentarily delaying the extraction phase thereby increasing compression/contraction force on the heart muscle.

One aspect of certain embodiments of the disclosure is to provide a more compact and lighter PLV apparatus that provides more efficient heat exchange to the lungs and/or that can also respond to pressure change due to a CPR procedure or to a patient's own breathing to reduce likelihood of barotrauma to the patient.

In accordance with certain embodiments disclosed herein, an apparatus for providing partial liquid ventilation to lungs of a mammal provides heat exchange in the lungs of the mammal without or reduced danger of causing barotrauma to the patient.

Certain embodiments comprise an apparatus for providing fluid to a lung. The apparatus can include a delivery device configured to deliver liquid and/or gas to the lung; a liquid delivery passage, a gas delivery passage and a suction passage, the liquid delivery, the gas delivery and the suction passages in fluid communication with the delivery device, a fluid reservoir in fluid communication with the liquid delivery passage; a vacuum source in communication with the suction passage; a gas source in communication with the gas delivery passage; and one or more pressure sensors. The apparatus can include one or more valves configured to control flow through the liquid delivery, the gas delivery and/or the suction passages when the apparatus switches between an inhale phase and an exhale phase. A control unit can be operatively connected to the patient's airway pressure sensor(s) or optionally other non-patient airway connected sensors, switches or a manual switch(es) and one or more valves, the control unit configured to, in response to a signal from the pressure sensor(s), to switch the apparatus between an inhale phase in which the liquid from the fluid reservoir is delivered through the liquid delivery passage and to the delivery device to the patient and/or gas can be delivered from the gas source to the gas delivery passage to the delivery device to the patient and an exhale phase in which liquid and/or gas can be withdrawn from the patient through the delivery device into the suction passage.

Certain embodiments can comprise a method for partial liquid ventilation of lungs, comprising detecting a pressure in the lungs; when upon conclusion of the patient's exhalation breath, the airway pressure reaches an initial value, which initiates the delivery of gas into the lungs and subsequent delivery of a liquid to the lungs during an inhale phase; and when the pressure reaches a second value, switching back to the exhale phase and withdrawing liquid and/or gas from the lungs until the pressure reaches the previous initial value or a third value repeating the breathing cycle. In lieu of patient airway pressure sensing, optionally, manual control or other sensor means could be employed to switch between inhale and exhale breathing cycles.

Certain embodiments can comprise a method for partial liquid ventilation of lungs, comprising, in response to detecting a patient's breathing, delivering gas into the lungs and subsequently delivering a liquid to the lungs during an inhale phase; detecting a pressure in the lungs; and when the pressure reaches a first value, switching to an exhale phase and withdrawing liquid and/or gas from the lungs until the pressure reaches a second value.

Certain embodiments can comprise a method for partial liquid ventilation of lungs, comprising in response to an application of pressure to a patient's lungs during a cardiopulmonary resuscitation, delivering gas into the lungs and subsequently delivering a liquid to the lungs during an inhale phase; detecting a pressure in the lungs; and when the pressure reaches a first value, switching to an exhale phase and withdrawing liquid and/or gas from the lungs until the pressure reaches a second value.

Certain embodiments can comprise a method for liquid ventilation of lungs, comprising aerating a liquid with a turbine pump; and delivering the aerated liquid to the lungs.

Certain embodiments can comprise a method for liquid ventilation of lungs, comprising with a turbine pump mixing a first liquid with a second fluid to create an emulsification of the first liquid and second fluid, wherein the second fluid is at a different temperature and/or may have different properties including being a gas than the first liquid; and delivering the emulsification or aerated liquid to the lungs.

Certain embodiments can comprise an apparatus for providing liquid and/or gas to a lung that includes a delivery device configured to deliver liquid and/or gas to the lung; a liquid delivery passage, a gas delivery passage and a suction passage, the liquid delivery, the gas delivery and the suction passages in fluid communication with the delivery device, a fluid reservoir in fluid communication with the liquid delivery passage; a vacuum source in communication with the suction passage; a gas source in communication with the gas delivery passage; and a one or more valves configured to control flow through the liquid delivery, the gas delivery and/or the suction passages when the apparatus switches between an inhale phase and an exhale phase. The apparatus can switch between a gas ventilation mode, and partial liquid ventilation mode and/or a total liquid ventilation mode.

Certain embodiments can comprise an apparatus for providing liquid and/or gas to a lung that includes one or more magnetic or non-mechanical contact switches configured to prevent arcing.

Certain embodiments can include an apparatus for providing liquid and/or gas to a lung that includes a fluid containment and/or filter for containing and/or filtering gas and/or liquid removed from the lung.

Certain embodiments can include a method for ventilating of a lung of a patient that includes applying a band configured to limit stretching of a patient's lungs; and supplying ventilation to the patient.

Further, modified and additional embodiments, features and advantages of the disclosure will become apparent from the detailed description taken in conjunction with the accompanying figures showing illustrative embodiments of the disclosure and the claims.

BRIEF DESCRIPTION OF THE DRAWINGS

The drawings and following associated descriptions are provided to illustrate embodiments of the present disclosure and do not limit the scope of the claims. Corresponding numerals indicate corresponding parts.

FIG. 8B is a timing table for the apparatus and an AutoPulse® CPR device as shown in FIG. 8A.

DETAILED DESCRIPTION OF THE PREFERRED EMBODIMENTS

Figure 1A:
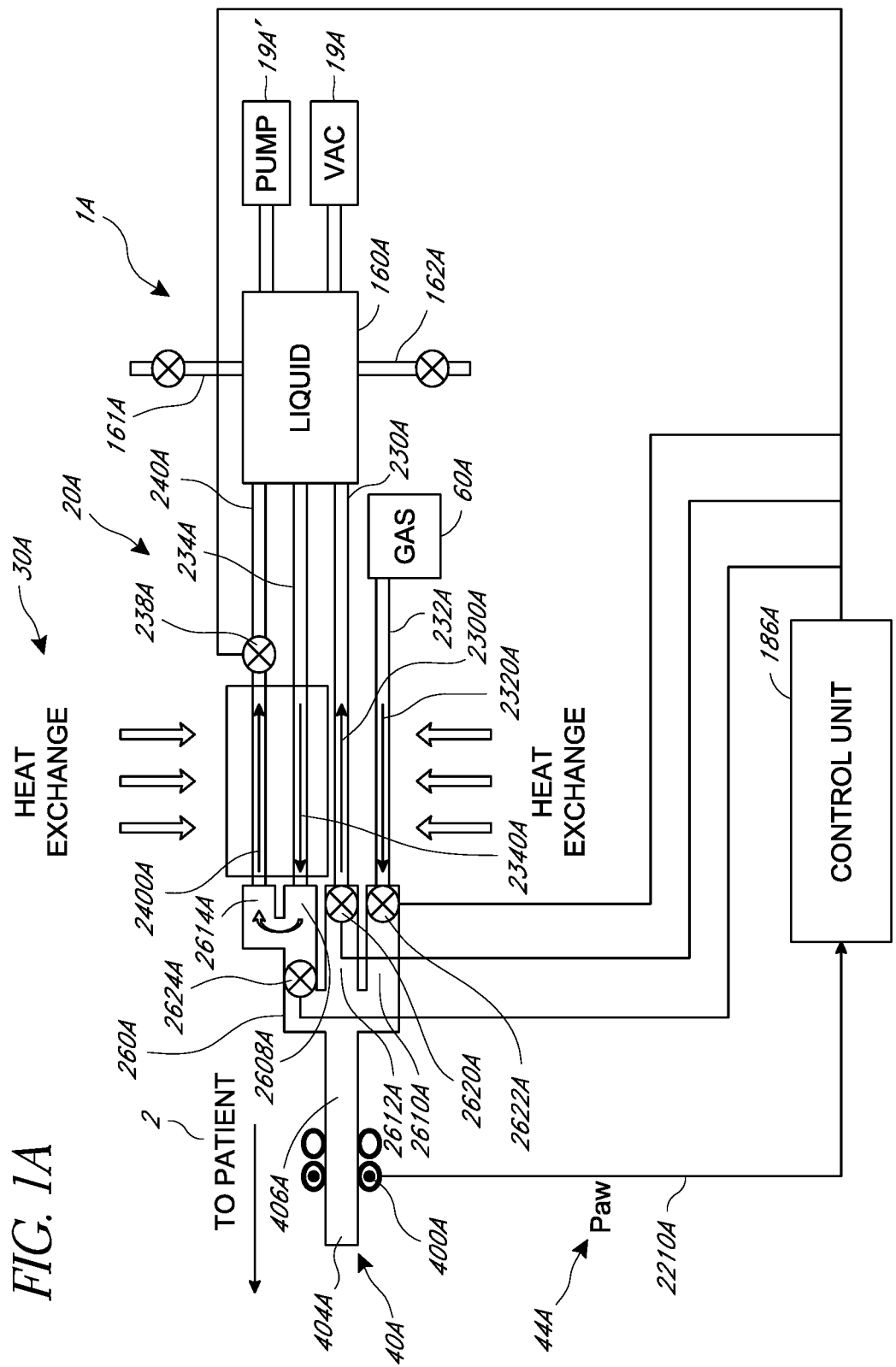
FIG. 1A illustrates a schematic diaphragm of an apparatus in accordance with an example embodiment of the present disclosure.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments. In addition, embodiments of the inventions can comprise several novel features and no single feature is solely responsible for its desirable attributes or is essential to practicing the inventions herein described.

Although certain aspects, advantages, and features are described herein, it is not necessary that any particular embodiment include or achieve any or all of those aspects, advantages, and features. Some embodiments may not achieve the advantages described herein, but may achieve other advantages instead. Any structure, feature, or step in any embodiment can be used in place of, or in addition to, any structure, feature, or step in any other embodiment, or omitted. This disclosure contemplates all combinations of features from the various disclosed embodiments. No feature, structure, or step is essential or indispensable. Features may also be integrated or subdivided as necessary, such that the any combination of features, whether integrated, separated, removed, added, duplicated, or otherwise recombined fall within the scope of the instant disclosure.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

FIG. 1A illustrates schematically an example embodiment of a fluid ventilation apparatus 1A (also referred to as an "apparatus" herein). As will be described below, the apparatus 1A can be used to deliver liquid and/or gas ventilation to the lungs of a mammal, such as a human patient 2 (see FIG. 11). In some embodiments, the apparatus 1A can provide a heated and/or cooled liquid to the lungs. In some embodiments, the apparatus 1A can also provide gas ventilation to the lungs of a patient. For example, in some embodiments, the apparatus 1A provides cooled partial liquid ventilation (PLV) to the lungs. As will be explained below, in certain embodiments, the apparatus described herein can operate in gas ventilation mode, partial liquid ventilation (PLV) mode and/or a total liquid ventilation mode (PLV) and in certain embodiments the apparatus can be configured to switch between such modes. In addition, certain features and aspects of the embodiments described herein can find utility and/or advantages in a device that is configured only for gas ventilation mode, only for partial liquid ventilation (PLV) mode and/or only for total liquid ventilation mode (PLV) or sub-combinations thereof.

The liquid used in the apparatus 1A can be any liquid suitable for being delivered into the lungs of a mammal, for example, any biocompatible fluid, water, saline, and/or perfluorocarbon (PFC). In certain embodiments, the liquid can be an oxygen carrying liquid such as, for example perfluorocarbon (PFC). In certain embodiments, the liquid may or may not be oxygenated prior to the delivery to the lungs. In addition, as noted above, in certain embodiments the liquid can be heated and/or cooled. Gas used in the apparatus 1A can be oxygen, atmospheric air, and/or an anesthetic gas or combinations thereof. In certain embodiments, the gas can be also heated and/or cooled.

The terms "cold", "cooled", "hot," "warm" and their equivalents in this disclosure are relative to the body temperature of a mammal before administration of heat exchange as understood by an artisan. "Cold," "cooled" and their equivalents refer to temperatures below the body temperature of a mammal before administration of heat exchange. "Hot," "warm" and their equivalents refer to temperatures above the body temperature of a mammal before administration of heat exchange.

With continued reference to FIG. 1A, the apparatus 1A can include a delivery device, which in the illustrated embodiment comprises an endotracheal tube 40A having a proximal end 406A and a distal end 404A. In certain embodiments, the delivery device can comprise other devices configured to aid in interfacing with a patient to deliver fluid to a patient's lungs such as a mask and/or nasal cannula and/or a tracheostomy tube and/or device allowing for immersion of the patient in a breathing liquid. The proximal end 406A of the endotracheal tube can be connected to a hub 260A. The hub 260A can have one or more passages for delivering and/or removing fluid to and/or from the delivery device, which as noted above in the illustrated arrangement is an endotracheal tube 40A. In the illustrated embodiment, the hub 260A can include a liquid delivery passage 2608A, a suction passage 2612A, a gas delivery passage 2610A and a recirculation tube passage 2614A. As will be described below, the liquid and/or gas flowing through these passages can be controlled by one or more valves, which can be placed in these passages 2608A, 2612A, 2610A, 2614A.

As shown in FIG. 1A, the hub 260A can be connected to a tube assembly 20A. In one embodiment, the tube assembly 20A can include one or more tubes that correspond to the passages in the hub 260A. In one embodiment, the tube assembly 20A is generally flexible and can have various lengths, and in one example embodiment, the tube assembly 20A can have a length between about 2 to 12 feet. In one arrangement, the tube assembly 20A includes a suction tube 230A that can be in fluid communication with the suction passage 2612A of the hub 260A. The tube assembly 20A can also include a gas delivery tube 232A that can be in fluid communication with the gas delivery passage 2610A of the hub 260A. The tube assembly 20A can also include a liquid delivery tube 234A that can be in fluid communication with the liquid delivery passage 2608A of the hub 20A. The tube assembly 20A can also include a liquid recirculation tube 240A in fluid communication with the recirculation tube passage 2614A of the hub 260A.

The gas delivery tube 232A can be connected to a gas source 60A which can provide pressurized and/or unpressurized air and/or gas to the gas delivery tube 232A. The term "gas source" is a broad term that is intended to comprise any source for pressurized and/or unpressurized air and/or gas such that the gas source 60A can comprise any of a wide variety of sources of pressurized and/or unpressurized air and/or gas such as, for example, a pressurized air and/or gas tank and/or a pump and/or compressor and/or an opening and/or connection to atmospheric air. In a similar manner, the liquid delivery tube 234A can be connected to the fluid reservoir 160A which can comprise a reservoir of liquid and/or a pump for delivering the liquid from the fluid reservoir 160A to the liquid delivery tube 234A. The reservoir can include a gas outlet 162A which can be coupled to a scrubber or similar device configured to remove $CO_2$ from the liquid in the reservoir 160A. The fluid reservoir 160A can also include an inlet 161A through which air, $O_2$ and/or another gas can be introduced into the fluid reservoir 160A. As described herein, in certain embodiments, the patient or subject will be consuming oxygen and throwing off $CO_2$ during a treatment process. The $CO_2$ can be removed from the liquid via the outlet 162A and additional $O_2$ can be added to the liquid via the inlet 161A. The suction tube 230A can be placed in communication with a vacuum source 19A. The fluid reservoir 160A can include a pump 19A' for delivering liquid from the fluid reservoir 160A through the liquid delivery tube 234A and the liquid delivery passage 2608A and to the delivery device 40A. The vacuum source 19A can be used to apply suction or vacuum through the suction tube 230A, the suction passage 2612A and the delivery device 40A. In the illustrated embodiment, the suction tube 240 can also be in fluid communication with the fluid reservoir such that any liquid withdrawn through the suction tube 240 can be returned to the fluid reservoir 160A. As will be explained below, in certain embodiments, a single pump can be used to alternatively replace or with the fluid reservoir 160A under pressure or under vacuum such that the fluid reservoir can function as the vacuum source in communication with the suction tube 230A and/or the pressure source in communication with 234A.

In the illustrated embodiments, the suction tube 230A, the gas delivery tube 232A, the liquid delivery tube 234A and the liquid recirculation tube 240A are shown as separate components from the hub 260A and the associated passages 2612A, 2601A, 2608A, 2614A within the hub 260A. In certain embodiments, these components can be combined such that the passages and tubes form a single component and/or additional components can be provided between these tubes and passages.

The distal end 404A of the endotracheal tube 40A can be configured to be inserted into the human patient 2's airway (trachea). The distal end 404A of the endotracheal tube 40A can also include a pressure sensor 400A that can measure a human patient's airway pressure $P_{aw}$ 44A when the endotracheal tube 40A is positioned within the patient 2. As used herein the term "pressure sensor" is intended to include any of a variety of sensors that can provide a signal and/or other indication that is directly and/or indirectly indicative of pressure at a desired location. Accordingly, the pressure sensor 400A can comprise any of a variety of sensors that are indicative of pressure at a desired location such as, for example, conventional electric pressure sensors that measure or sense strain or deflection due to pressure and/or Micro-Electro-Mechanical Systems (MEMS) and/or an optic based systems and/or the pressure sensing apparatuses and fiber optic pressure sensors described in U.S. Pat. Nos. 8,022,835; 7,284,436; 7,096,737; and/or 6,604,427, which are incorporated by reference herein in their entirety for all purposes. In the illustrated embodiment, the pressure sensor 400A is illustrated as positioned on the endotracheal tube 40A and optionally can be connected to a pilot tube positioned down the length of the endotracheal tube and made to be easily removable for periodic cleaning or replacement while ventilating. In certain embodiments, the pressure sensor 400A can be positioned at a location remote from the endotracheal tube 40A but connected through a pilot tube or similar apparatus with an opening on or near the endotracheal tube 40A and/or a connection of the endotracheal tube 40A to the hub 260A. In one embodiment, the pressure sensor 400A can be part of a balloon cuff, the details of certain embodiments will be provided below. The pressure sensor 400A advantageously can be configured to sense pressure change when only gas is delivered, when a mixture of gas and liquid is delivered, and/or when only liquid is delivered by the apparatus 1A. The endotracheal tube 40A can optionally feature a lumen in the wall, in addition to any lumen(s) used for cuff inflation, which ends at or near the distal end of the tube. The pressure sensor 400A can be incorporated into this lumen.

As shown in FIG. 1A, the pressure sensor 400A can be operatively connected to a control unit 186A. The control unit 186A can use the information from the pressure sensor 400A to output electrical signals and/or instructions (as described below) to control the flow of the liquid and gas between the tube assembly 20A and the endotracheal tube 40A by controlling opening and closing of one or more two-way valves (described below) that can be provided in the hub 260A and/or in other parts of the apparatus 1A, such as a manifold as described in a later illustrated embodiment. Accordingly, in the illustrated arrangement, the control unit 186A can be operatively connected to a suction valve 2620A, a gas delivery valve 2622A and/or a liquid delivery valve 2624A. The control unit 186A can also be operatively connected to a recirculation valve 238A. These valves 2620A, 2622A, 2624A, 238A can be two-way valves selected from a variety of types of valves. In one embodiment, the two-way valves are pneumatically piloted valves. Opening and closing of the two-way valves 2620A, 2622A, 2624A, 238A according to the signals sent by the control unit 186A can be done by any conventional actuators, such as electrical, hydraulic or pneumatic actuation. In one embodiment, the two-way valves comprise piloted valves, which are controlled by smaller pilot solenoid valves, which in turn can be three way valves or triple ported valves. The apparatus 1A can include additional sensors and/or switches such as adjustable pressure switches, vacuum sensors, adjustable vacuum switches, pressure meters, vacuum meters and/or thermometers.

Figure 12:
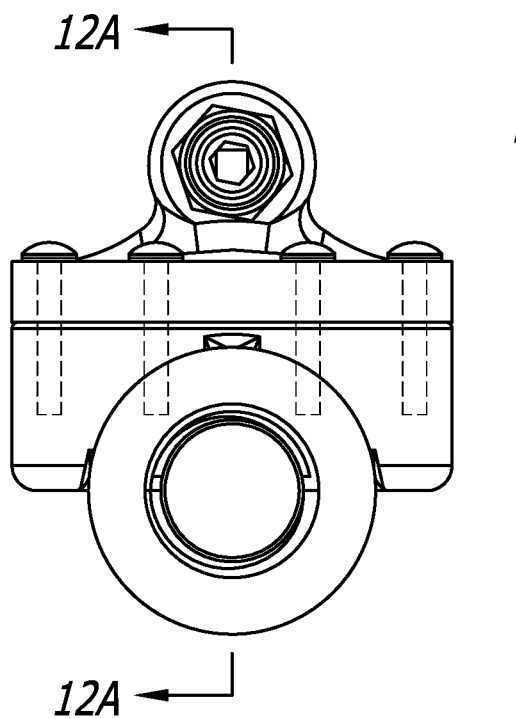
FIG. 12 illustrates an exemplary contoured diaphragm to create a sealing surface for valves according to embodiments described herein.
Figure 12A:
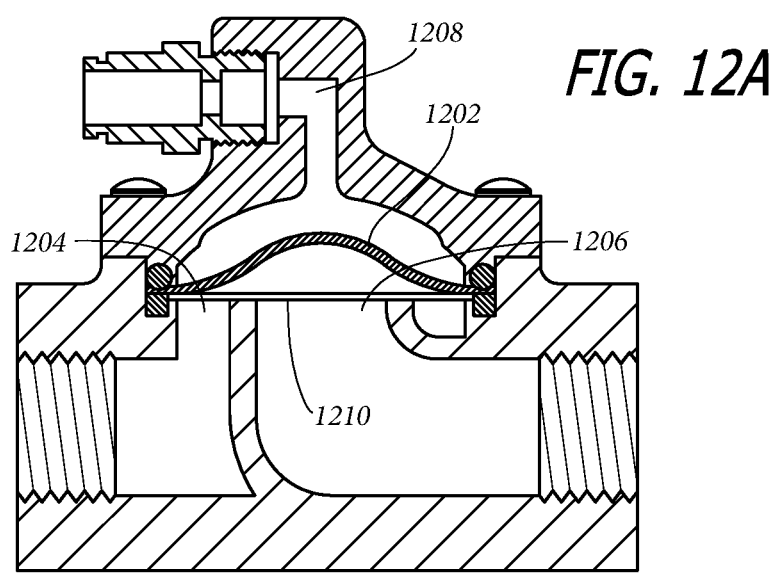
FIG. 12A illustrates an exemplary cross section of FIG. 12.

In an exemplary embodiment, valves described herein may include a diaphragm. FIG. 12 illustrates an exemplary contoured diaphragm to create a sealing surface for the valve. As shown, the valve is normally open, and closes with the application of pressure. However, the valve may be normally closed. The valve may also be opened with pressure and/or opened or closed with a vacuum. As shown, having a normally open valve that opens with a change in pressure permits one of the pressure sources to be removed from the system. For instance, the vacuum pump may be removed, and a single pump used to control the valves. In this case, the valve may be controlled by applying a greater than atmospheric pressure to close the valve, and applying atmospheric pressure or simply opening the line to atmosphere to open the valve. As illustrated in the cross section of FIG. 12A, the valve includes a diaphragm 1202 in a normally open configuration that permits to and from flow between a first opening 1204 and a second opening 1206. As shown, the first and second openings are in a common plane 1210 and positioned on the same side of the diaphragm. The valve diaphragm in a relaxed or normal configuration is in contact with the plane containing the first and second opening at an outer perimeter of the diaphragm and out of contact with the plane on an interior region of the diaphragm. For example, the diaphragm may be curved or dome shaped. The valve may include a control opening 1208 on an opposite side of the diaphragm from the first and second opening. The control opening configured to supply pressure or vacuum or remove pressure or vacuum to control the position of the diaphragm, such as in either a closed or open configuration. There may be a spring element incorporated into the valve to cause or assist closure, or the diaphragm may be configured such that it returns to some shape with removal of the controlling pressure or controlling vacuum.

In this disclosure, various components are described as being "operatively connected" to the control unit. It should be appreciated that this is a broad term that includes physical connections (e.g., electrical wires) and non-physical connections (e.g., radio or infrared signals). It should also be appreciated that "operatively connected" includes direct connections and indirect connections (e.g., through an additional intermediate device, control unit or processor). In various embodiments, the control unit 186A may include one or more processors, one or more memories, and one or more communication mechanisms. In some embodiments, more than one control unit may be used to execute the modules, methods, and processes discussed herein. Additionally, the modules and processes herein may each run on one or multiple processors, on one or more control units or processes; or the modules herein may run on dedicated electrical hardware and may have non-dedicated peripherals, data storage, data sharing, diagnostics, virtually real time monitoring and post data processing and analysis such as with cloud communications. The control unit 186A may include an input device such as one or more keyboards (one-handed or two-handed), a mouse, touch screens, voice commands and associated hardware, gesture recognition, or any other device or method of providing communication between an operator and the control unit 186A.

The hub 260A can connect the proximal end 406A of the endotracheal tube 40A to the tube assembly 20A. In the illustrated embodiment, the suction valve 2620A, the gas delivery valve 2622A, and the liquid delivery valve 2624A can be located in the hub 260A. In other words, in the illustrated embodiment, these three valves 2620A, 2622A, 2624A can be located near a distal end of the tube assembly 20A. In the illustrated embodiment, the recirculation valve 238A can be located at a location nearer to a proximal end of the tube assembly 20A and closer to the fluid reservoir 160A than the other three valves 2620A, 2622A, 2624A. In modified embodiments, the location of these valves 2620A, 2622A, 2624A, 238A can be modified. In the illustrated embodiment, having the suction valve 2620A, the gas delivery valve 2622A and the liquid delivery valve 2624A located on the hub 260A can advantageously reduce an overall size of the tube assembly 20A. In certain embodiments, these valves 2620A, 2622A, 2624A can be located at other parts of the apparatus 1A. In the illustrated embodiment, the liquid delivery tube 234A, the liquid recirculation tube 240A and the suction tube 230A can also be connected on a proximal end to the single fluid reservoir 160A. In some embodiments, the liquid recirculation tube 240A and the suction tube 230A can be connected to a top of the fluid reservoir 160A to return the liquid to the fluid reservoir 160A and the liquid delivery tube 234A can be connected a bottom of the fluid reservoir 160A to collect the liquid. One of the advantages of having a single fluid reservoir is to reduce the size and weight of the apparatus 1A and to reduce the need for refilling the reservoir with fresh liquid because at least a portion of the liquid leaving the fluid reservoir 160A is recycled back to the fluid reservoir 160A via the liquid recirculation tube 240A and the suction tube 230A. Other advantages of the single fluid reservoir will be discussed below.

While a single fluid reservoir has certain advantages, in certain arrangements, the apparatus 1A can be provided with more than one fluid reservoir. For example, one or more of the liquid delivery tube 234A, the liquid recirculation tube 240A and the suction tube 230A can be connected to separate reservoirs. In certain embodiments, one or more of directions of flow 2300A, 2320A, 2340A, and 2400A may additionally be driven by one or more pumps (not shown in FIG. 1A) that are capable of exerting pressure or negative pressure (vacuum) on the liquid or the gas. In the illustrated embodiment, the gas delivery tube 232A can also connected to the gas source 60A, which can be atmospheric air, a source of anesthetic gas, or other types of ventilation gas according to the need of the patient 2. Multiple containers may serve the purpose of preventing liquids from entering certain parts of the machine.

The control unit 186A can be configured to send control signals to open and/or close the suction valve 2620A, the gas delivery valve 2622A, the liquid delivery valve 2624A and/or the recirculation valve 238A based on changes in the human patient's or animal's airway pressure ($P_{aw}$) 44A according to certain protocols and/or control routines as described herein. In certain embodiments, the timing of opening and closing of some of the valves may be synchronized. For example, the liquid delivery valve 2624A and the gas delivery valve 2622A can be closed at the same time as the suction valve 2620A is opened when $P_{aw}$ 44A reaches a predetermined maximum threshold pressure value and the apparatus 1A switches from an inhale phase to an exhale phase. The liquid and the ventilation gas that has been delivered inside the patient's lungs can be vacuumed from the lungs via the suction tube 230A under a vacuum, with the removed liquid returned to the fluid reservoir 160A and the removed gas pumped out of the fluid reservoir 160A and released into the atmosphere or captured in an external capture system in certain embodiments. During the exhale phase, vacuum extraction can additionally aid removal of carbon dioxide from the removed liquid due to lower partial pressure of carbon dioxide in the vacuum than in the liquid. In certain embodiments, the liquid delivery valve 2624A and the gas delivery valve 2622A can be closed independently at different times instead of closing simultaneously. During the exhale phase, the recirculation valve 238A can also be opened at the same time so that the liquid can be recirculated back to the fluid reservoir 160A and thus can receive in the certain embodiment additional heat extraction. The predetermined threshold pressure and/or the preset vacuum can be adjusted and/or set by the user of the apparatus for example by using an input device associated with the control unit 186A.

Reversely, during an inhale phase, the suction valve 2620A can be closed when $P_{aw}$ 44A reaches a predetermined minimum threshold pressure value and the apparatus 1A switches from an exhale phase to an inhale phase. During the inhale phase, the liquid delivery valve 2624A and the gas delivery valve 2622A can open at the same time the suction valve 2620A is closed. Again, the liquid delivery valve 2624A and the gas delivery valve 2622A can be opened simultaneously or independently. The gas and/or the liquid can then be delivered to the endotracheal tube 40A under a pressure. Pressured delivery of the liquid may help oxygenate the liquid delivered to the patient 2 because the partial pressure of oxygen can be higher in the inhaled fresh air or other supplied gas than in the liquid. In certain modified embodiments, the control unit 186A can be configured to open and close the suction valve 2620A, the gas delivery valve 2622A, the liquid delivery valve 2624A and the recirculation valve 238A according to other timing schedules, such as adding a delay to the opening or closing of any of the valves and/or in response to other sensed values. In certain embodiments, the apparatus 1A can be used as a time division multiplexed blender. For example, in certain embodiments, using time division multiplexing, timing schedules can be configured to precisely mix multiple gasses and/or liquids and/or gasses to synthesize a prescribed blend, which can be delivered to the lungs. In certain example arrangements, gasses could be added on a breath by breath basis, for example, trace gasses could be added in defined percentages to perform diagnostics such as the addition of helium or acetylene for the purpose of metabolic rate measurements with the addition of complementary diagnostic devices. In certain embodiments, the apparatus 1A can be configured with a user controlled setting such that Partial Liquid Ventilation ("PLV") and/or Total Liquid Ventilation ("TLV") can be provided to the patient via control of the fluid reservoir 160A, and/or control of the gas delivery tube 232A, and/or control of the gas delivery valve 2622A. Applicant's current understanding based on experiments is that Partial Liquid Ventilation has the advantage of keeping the alveoli open and receptive to subsequent filling with liquid, increasing thermal exchange efficiency, while keeping some normal gas to gas exchange in the presence of the liquid. Nevertheless, in certain embodiments of the apparatuses described herein PLV and/or TLV may be beneficially provided according to the needs of the patient, such as life support, lung lavage and/or needs of the environment, and/or to closely maintain the materials that have been in contact with the patient.

The predetermined threshold pressure can be achieved in a variety of circumstances. For example, the lungs could have filled to their volume available with the fluid and gas by the apparatus. Alternatively, CPR could have been applied, exerting a pressure equal to or exceeding the predetermined threshold pressure in the lungs. Another possibility would be that the patient attempts to breathe on his or her own. An advantage to certain embodiments of the apparatus described herein is that the apparatus can be sensitive to pressure change from a CPR procedure or a patient's own breathing in addition to active filling by the apparatus so that active filling can stop as soon as the pressure in the patient's airway reaches the threshold regardless of how the threshold pressure is achieved, thereby minimizing harm to the patient and/or and acting as a breathing aid to a patient not fully capable of breathing on his/her own.

Also as shown in FIG. 1A, a heat exchanger 30A can be provided to the tube assembly 20A to heat and/or cool the gas and/or liquid flowing through the tube assembly 20A, thereby providing heated and/or cooled liquid and/or heated and/or cooled ventilation gas to the lungs of the patient. In a modified embodiment, the entire apparatus 1A or portions thereof can be heated and/or cooled including the fluid reservoir 160A and/or gas supply 60A. Providing the heat exchanger 30A at the tubing assembly 20A instead of at or close to the fluid reservoir 160A can advantageously eliminate or reduce the need for a bulky heat exchange manifold in connection with the fluid reservoir 160A, which can in certain embodiments reduce the overall size and weight of the apparatus, and also can in certain embodiments reduce the cooled liquid and/or gas warming up or heated liquid and/or gas cooling down in the delivery tubes. In certain embodiments, the already cooled or heated liquid in the liquid recirculation tube 260A returns to the same fluid reservoir 160A, which can provide even more efficient cooling or heating of the liquid.

Figure 1B:
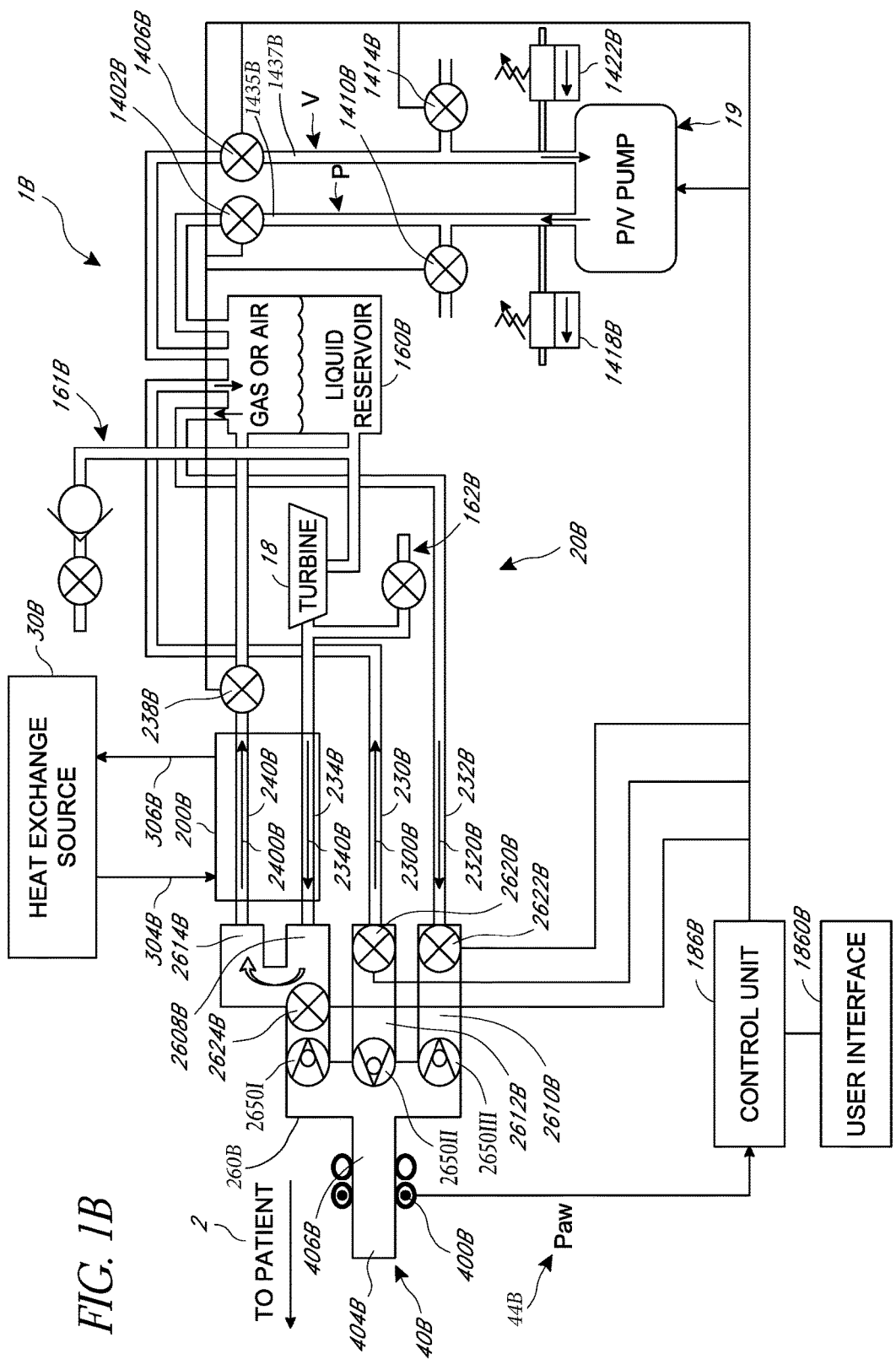
FIG. 1B illustrates a schematic diaphragm of an apparatus in accordance with another example embodiment of the present disclosure.

FIG. 1B illustrates another example embodiment of a fluid ventilation apparatus 1B (also referred to as an "apparatus" herein), which can be used to deliver liquid and/or gas ventilation to the lungs of a mammal, such as a human patient 2. As with the embodiment of FIG. 1A, the apparatus 1B can provide a heated and/or cooled liquid to the lungs. In some embodiments, the apparatus 1B can also provide gas ventilation to the lungs of a patient. For example, in some embodiments, the apparatus 1B provides cooled partial liquid ventilation (PLV) to the lungs. For another example, in some embodiments, or in the same embodiment, the apparatus 1B provides cooled total liquid ventilation (TLV) to the lungs as controlled by a user controlled or automatic setting, or conventional gas ventilation as controlled by a user controlled or automatic setting, or any of PLV, TLV and conventional gas ventilation modes at different times as required. An advantage of certain embodiments is that if no liquid is present in the fluid reservoir 160A, 160B, the apparatus 1A, 1B can function as a dry ventilator. This may be due to the use of the apparatus 1A, 1B as a dry ventilator, and/or in the emergency application, the liquid simply has not been added to the fluid reservoir 160B yet and/or has left the system such as through evaporation, and/or through faults in the system or the patient or animal, and/or the apparatus 1B is being used as a lavage and the liquid in the fluid reservoir 160B is in the process of being cleaned replace, renewed and/or oxygenated. As noted above, the fluid reservoir 160B can include an outlet which can be used to drain liquid from the fluid reservoir 160B such that the apparatus 1B can be used as dry ventilator. Features of the embodiment of FIG. 1B corresponding to those described with reference FIG. 1A are referenced by the same reference numerals but ending with "B" instead of A". Accordingly, the apparatus of FIG. 1B can be similar to the apparatus 1A of FIG. 1A except as described differently below. In certain arrangements, the features of the apparatus 1B can be incorporated into the apparatus 1A and the features of the apparatus 1A can be incorporated into the apparatus 1B. Features of FIGS. 1A and 1B may be combined or substituted as required to achieve the desired objective. The disclosed embodiments are exemplary only and not mutually exclusive.

With continued reference to FIG. 1B, the apparatus 1B can include a delivery device, which in certain embodiments can be an endotracheal tube 40B having a proximal end 406B and a distal end 404B. In certain embodiments, the delivery device can comprise other delivery devices configured to aid in interfacing with a patient to deliver liquid and/or gas to a patient's lungs such as a mask and/or nasal cannula and/or device allowing for immersion of the patient in a breathing liquid. The proximal end 406B of the endotracheal tube can be connected to a hub 260B. The hub 260B can have one or more passages for delivering and/or removing liquid or gas to and/or from the endotracheal tube. In the illustrated embodiment, the hub 260B includes a liquid delivery passage 2608B, a suction passage 2612B, a gas delivery passage 2610B and a recirculation tube passage 2614B. As will be described below, the liquid and/or gas flowing through these passages can be controlled by one or more valves, which are placed in the passages.

As shown in FIG. 1B, the hub 260B can be connected to a proximal end 406B of a tube assembly 20B. In one embodiment, the tube assembly 20B includes one or more tubes that correspond to the passages in the hub 260B. In one embodiment, the tube assembly 20B is generally flexible and can have lengths and in one embodiment can be about 2 to 12 feet in length. Similar to the tube assembly 20A, the tube assembly 20B can comprise a heat exchanger 200B, which can connect to a heat exchange source 30B via a heat exchange inlet 304B and a heat exchange outlet 306B. In one arrangement, the tube assembly 20B includes a suction tube 230B that can be in fluid communication with the suction passage of the hub. The tube assembly 20B can also include a gas delivery tube 232B that can be in fluid communication with the gas delivery passage 2610B of the hub. The tube assembly 20B can also include a liquid delivery tube 234B that can be in fluid communication with the liquid delivery passage 2608B of the hub. The tube assembly can also include a liquid recirculation tube 240B in fluid communication with the recirculation tube passage 2614B of the hub.

The hub 260B can include a plurality of two-way valves 2620B, 2622B, 2624B, which are respectively positioned within the suction, the gas delivery, and the liquid delivery passages of the hub 260B. In addition, the hub 260B can include a plurality of one-way check valves 2650I, 2650II, 2650III within the liquid delivery, the suction, and/or the gas delivery passages respectively. The check valve 2650I in the liquid delivery passage 2608B only allows liquid to flow from the tube assembly 20B to the endotracheal tube 40B and is located distally of the liquid delivery valve 2624B. The check valve 2650III in the gas delivery passage only allows gas to flow from the tube assembly 20B to the endotracheal tube 40B and is located distally of the gas delivery valve 2622B. The check valve 2650II in the suction passage can be configured to only allow liquid and/or gas along with any suspended solids to flow from the endotracheal tube 40B to the tube assembly 20B and is located distally of the suction valve 2620B. More specifically, the check valve 2650I can be configured to only open in the direction 2340B that allows a liquid to flow from a liquid delivery tube 234B to the endotracheal tube 40B. The check valve 2650III can be configured to only open in the direction 2320B that allows the air and/or oxygen and/or other gases to flow from a gas delivery tube 2320B to the endotracheal tube 40B. The check valve 2650II can be configured to only allow flow in the direction 2300B that allows a mixture of liquid(s) and gas(es) that was in the patient's lungs to flow from the endotracheal tube 40B to the suction tube 230B. In certain embodiments, having the check valves advantageously provides additional safety of the apparatus 1B by ensuring that directions of flow in the hub 260B are as intended and also reducing the likelihood of backflow of the gas and/or liquid in the tube assembly 20B. In some embodiments, additional one-way check valves may be places in other tubes of the apparatus 1B. In certain embodiments, the check valves can be used to enable differential timing of fluid with automatic dry ventilation.

The apparatus 1B can also include a turbine pump 18 between a fluid reservoir 160B, which will be described below, and the liquid delivery tube 234B. The turbine pump 18 can be small in size and light in weight, but can be powerful enough to advantageously draw the liquid out of the fluid reservoir 160B and eventually to the endotracheal tube 40B faster than without the turbine pump 18, which in certain embodiments can make the apparatus 1B more efficient. In certain embodiments, the turbine pump 18 advantageously has no seals like in a piston pump or liquid contacting diaphragms, which can make the turbine pump 18 easy to be incorporated into the apparatus 1B. In certain embodiments, the turbine pump 18 can advantageously also run dry of liquid, and can continue to run without damage if there are stoppages of the flow of liquid through it. While the turbine pump 18 has certain advantages as described above, in other embodiments, a different type of pump can be used.

The turbine pump 18 can include an aerator feature 161B as shown in FIG. 1B, which in certain embodiments can advantageously aerate the liquid by withdrawing gases allowed into the aerator feature 161B and causing them to be dissolved into the liquid via agitation and size reduction of the bubbles in the liquid(s) as the liquid(s) passes through the turbine pump 18. The aerator feature 161B also can be advantageously used as a point to fill the system with liquid while it is running and providing gas ventilation to the patient as liquid will be drawn through this aerator feature 161B during the exhale phase. In some embodiments, the aerator feature 161B can comprise a valved connector and a check valve. In some embodiments, the aerator feature 161B can be located at an inlet side of the turbine pump 18. The aerator feature 161B may be one used in a conventional bait pump or other types of aerator features, such as tall bubblers and gas exchange surfaces. Using the aerator feature of the bait pump can advantageously provide a lowered cost and reduce size and weight of the apparatus 1B. Oxygen in the air bubbles that are not absorbed into the liquid due to agitation at evacuation or agitation by a turbine of the turbine pump 18 can be absorbed within the travel in the tube assembly 20B. The turbine pump 18 may also be used to emulsify water or saline, or other liquids or compounds, into the fluid, such as PFC, to improve thermal properties before the heavier PFC separates from water or saline. Thermal capacitance of water is several times higher than PFC and therefore improves the thermal performance of the liquid delivered to the patient when water or saline is emulsified into PFC. Thus, in certain embodiments, the liquid delivered to the patient can be cooled or heated by emulsifying a cooled or heated first liquid (e.g., water or saline, and/or other liquids) in to the second liquid (e.g., PFC) intended to be delivered to the lungs. Accordingly, in one example embodiment, PFC can be cooled by emulsifying water from recently melted ice into the PFC before it is delivered to the lungs. A gas outlet 162B can be located at an outlet side of the turbine pump 18. The gas outlet 162B can be coupled to a scrubber or similar device configured to remove $CO_2$ from the liquid in the reservoir 160B.

With continued reference to FIG. 1B, similar to the tube assembly 20A, the liquid delivery tube 234B, the liquid recirculation tube 240B and the suction tube 230B can be connected to the single fluid reservoir 160B. The liquid recirculation tube 240B and the suction tube 230B are connected to a top portion of the fluid reservoir 160B and the liquid delivery tube 234B is connected to a bottom portion of the fluid reservoir 160B. Unlike the tube assembly 20A, the gas delivery tube 232B can also be connected to the top portion of the fluid reservoir 160B instead of directly to a gas source. Supply of gas to the gas delivery tube 232B will be described in detail below.

Also as shown in FIG. 1B, the apparatus 1B can include a pressure/vacuum ("P/V") pump 19 connected to the fluid reservoir 160B. The P/V pump 19 switches between a pressure state and a vacuum state as the apparatus 1B switches between an inhale phase and an exhale phase, making pressure P on one side and vacuum V on another side of the pump 19. More particularly, in certain embodiments, the P/V pump 19 can apply pressure P via a pressure line 1435B to the fluid reservoir 160B to push the liquid in the fluid reservoir 160B to enter the liquid delivery tube 234B (in addition to the turbine pump 18) when the apparatus 1B is in the inhale phase. The gas delivery tube 230B is in fluid communication with the top portion of the reservoir 160B so that gas from the P/V pump 19 enters into the reservoir 160B in a space not occupied by liquid. Gas in this space is also pushed into the gas delivery tube 232B by the P/V pump 19 in the inhale phase. The same P/V pump 19 can apply vacuum V via a vacuum line 1437B to the top portion of the fluid reservoir 160B to cause the liquid and/or gas from the suction tube 230B to enter the fluid reservoir 160B when the apparatus 1B is in the exhale phase. In one embodiment, the single pump 19 can be a diaphragm pump. In some embodiments, the P/V pump 19 can run continuously. In certain embodiments, having one state-switching pump can advantageously result in fewer components, reduced weight and lower power consumption for the apparatus 1B.

A pressure relief valve 1418B can be located on the pressure side of the P/V pump 19. A vacuum relief valve 1422B can be located on the vacuum side of the P/V pump 19. Any excess pressure or vacuum building up in the apparatus or in the patient's lungs can be released through the relief valves. The relief valves are optional and can protect the safety of the patient when abnormal $P_{aw}$ 44B, as well as protect the reservoir 160B and other components if excessive pressure or vacuum are generated or when the apparatus malfunctions, such as when there is a potential overpressure or excessive vacuum condition. The relief valves can also advantageously provide greater reliability and safety of the apparatus 1B without the need for pressure sensor or controls that are required on a large P/V pump, allowing a smaller, lighter and cheaper pump to be used. In some embodiments, the relief valves comprise adjustable spring-loaded diaphragms. However, exemplary embodiments may not include relief valves 1418B and/or 1422B as the control system may prevent over or under pressure within the system.

Returning to the endotracheal tube 40B, the distal end 404B of the endotracheal tube 40B can be configured to be inserted into the human patient 2's airway (trachea). The distal end 404B of the endotracheal tube 40B can include a pressure sensor 400B that measures a human patient's airway pressure $P_{aw}$ 44B while the apparatus 1B delivers liquid and/or gas ventilation to the lungs of the patient 2. Similar to the apparatus 1A, the pressure sensor 400B can be directly or indirectly coupled to a control unit 186B. The control unit 186B in turn can output instructions controlling the opening and closing of the valves 1402B, 1406B, 1410B, 1414B connected to the P/V pump 19 as well as the valves 238B, 2620B, 2622B, 2624B according to signals from the pressure sensor 400B as described above with respect to apparatus 1A of FIG. 1A, thereby deciding whether the apparatus is in the inhale phase (under P) or the exhale phase (under V). In some embodiments, the control unit 186B can comprise a user interface 1860B for turning the apparatus 1B on and off and/or controlling the operating parameters of the apparatus 1B such as, for example, the duration of an inhale and/or exhale phase and/or the timing and/or delay of such phase and/or the timing and/or delay of the delivery of liquid as compared to gas delivery. In certain embodiments, the user interface 1860B includes one or more magnetic switches. For example, that user interface 1860B can include an "on"/"off" magnetic switch, such as, for example, a vacuum envelop isolated magnetic reed switch construction, which prevent arcing into a flammable atmosphere. Use of such magnetic switches in the apparatus 1B can advantageously decrease fire risk when flammable gases are present.

As with many features and aspects described in this disclosure, the use of a magnetic switch that does not create sparks or arcing can also find utility and be advantageous when used in combination with a conventional gas ventilation device, and/or other apparatuses configured for ventilation, TLV and/or PLV and need not be used in combination with the features of the embodiments described herein. In certain embodiments, the primary pressure and vacuum lines from 19 to 160B can optionally include variable restrictors to control the cadence, or breath rate of the apparatus 1B.

In an exemplary embodiment, the turbine pump 18 can be controlled by the pressure in the fluid reservoir 160B. In this case, the circuitry to control unit 186B associated with the valve 238B can be removed, thereby simplifying the supporting electronics to the system. For example, when a pressure in the fluid reservoir reaches or surpasses a preset or programmable threshold, the turbine may activate, sending liquid to the patient. At the beginning an inhale phase, the suction valve 2620B can be closed when $P_{aw}$ 44B reaches a predetermined threshold pressure value and the apparatus 1B switches from an exhale phase to an inhale phase. During the inhale phase, the liquid delivery valve 2624B and the gas delivery valve 2622B can open at the same time the suction valve 2620B is closed. Again, the liquid delivery valve 2624B and the gas delivery valve 2622B can be opened simultaneously or independently. The gas and/or the liquid can then be delivered to the endotracheal tube 40B under a pressure. The pump 19 may supply pressure to move gas and/or liquid from the reservoir 160B to patient 2. Once the pressure reaches a predetermined value, the turbine 18 may turn on and assist with liquid delivery to the patient.

Turning to state switching of the apparatus 1B, in certain embodiments in which no liquid is delivered, during the inhale phase of the apparatus 1B, the valve 1410B closes and the valve 1402B opens so that air or gas from the P/V pump 19 pressurizes the reservoir 160B. The valve 1414B opens and the valve 1406B closes so that air or gas is taken in at an opening to the valve 1414B. The gas delivery valve 2622B opens to admit air or gas from the top portion of the now pressurized reservoir 160B in the space above the liquid if any is present in this volume. The suction valve 2620B can be kept closed during the inhale phase, aided by the check valve 2650II. Air or gas can continue to flow into the patient until a certain desired pressure is reached. The desired pressure can result from filling the lungs or compression of the lungs via manual or machine driven CPR. The apparatus 1B can switch to the exhale phase at the desired pressure. During the exhale phase, the valve 1410B opens and the valve 1402B closes so that air or gas from the P/V pump 19 is released as exhaust into the atmosphere, or optionally to an exhaust collection device (not shown). The valve 1414B closes and the valve 1406B opens so that the reservoir 160B is under vacuum (V). The gas delivery valve 2622B also closes. The liquid delivery valve 2624B may be in the closed condition to prevent liquid delivery and/or the reservoir 160B may simply be empty of liquid by intent or circumstance. The suction valve 2620B opens to now the vacuumized reservoir 160B can draw gas/air from the patient until a desired level of vacuum in the lungs is achieved. These embodiments could allow for full gas ventilation for life support of the patient if there is no liquid in the reservoir. A dry snorkel could be substituted for the wet heat exchange snorkel when exclusive use as a dry ventilator is expected. Such scenarios can happen when the reservoir has not yet been filled, when the apparatus is being used as a standard pressure sensitive gas ventilator, or when a user optionally stops liquid delivery or when injury or defect has allowed loss of the available liquid. The apparatus can do so without requiring additional sensors, controls or other types of equipment.

In some embodiments in which liquid is also delivered, in additional to the states of the valves as described above for the embodiments involving no liquid delivery, additional opening and closing of some valves can be involved. For example, during the inhale phase before $P_{aw}$ 44B reaches a predetermined threshold pressure value, the apparatus 1B can provide only gas to the patient 2 via the gas delivery tube 232B of the tube assembly 20B first. After a short delay during which the gas is being delivered, the liquid can overpower the lower pressure gas to close the check valve 2650III. The liquid can then be the dominant or only fluid being delivered to the patient. The short delay can be the amount of time taken for the liquid to reach the hub 260B, and/or approximately 90 milliseconds after the inhaling of gas or air. When liquid is the dominant or only fluid being delivered to the patient, the liquid recirculation valve 238B can close to terminate looping of the liquid through the heat exchanger 200B and the liquid delivery valve 2624B can open to admit liquid into the patient. The suction valve 2620B can be kept closed during the inhale phase, aided by the check valve 2650II. Once the $P_{aw}$ 44B reaches the predetermined maximum threshold pressure value, the liquid delivery valve 2624B can be closed and the liquid recirculation valve 238B can open, allowing the liquid to "short circuit" into the reservoir 160B without entering the patient. The suction valve 2620B can open so now the vacuumized reservoir 160B can draw fluid (a mix of gas/air and the volume of liquid beyond the reserve volume of the lungs) from the patient until a desired level of vacuum in the lungs is achieved. The desired level of vacuum in the lungs can be associated with the desired removal of fluid but should be below any level of vacuum that would cause injury or airway collapse of a patient. The reserve volume of the lungs is the part of the lung volume that cannot be exhaled and is approximately 1 liter in humans.

Figure 1C:
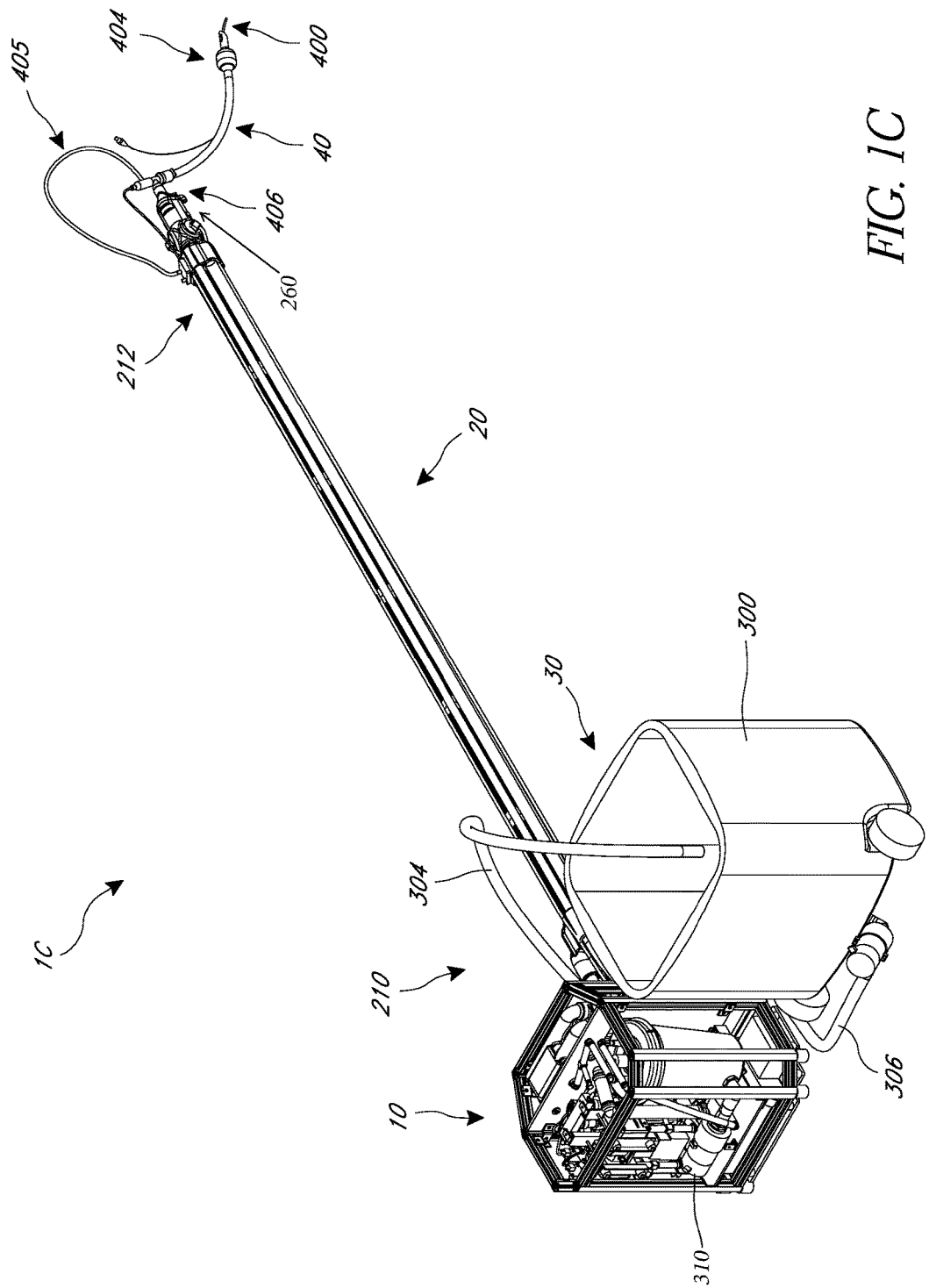
FIG. 1C illustrates a perspective view of an apparatus in accordance with yet another example embodiment of the present disclosure.
Figure 1D:
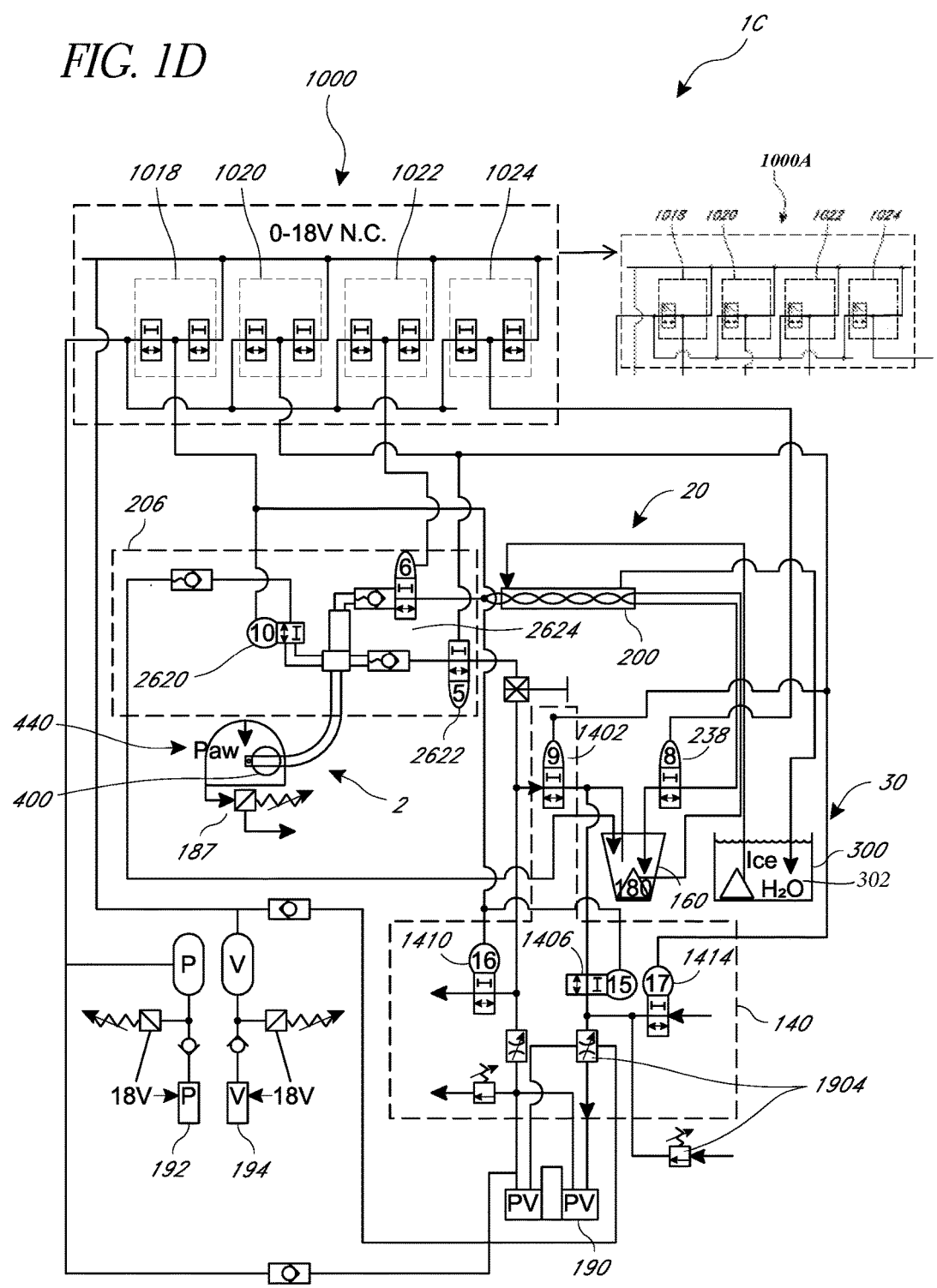
FIG. 1D is a block diaphragm illustrating operation of an apparatus in accordance with the example embodiment of the present disclosure shown in FIG. 1C.

FIGS. 1C-D illustrate another example embodiment of a liquid ventilation apparatus 1C (also referred to as an "apparatus" herein), which can be used to deliver liquid ventilation to the lungs of a mammal, such as a human patient. As with the embodiments of FIGS. 1A-B, the apparatus 1C can provide a heated and/or cooled liquid to the lungs. In some embodiments, the apparatus 1C can also provide gas ventilation to the lungs of a patient. For example, in some embodiments, the apparatus 1C provides cooled partial liquid ventilation (PLV) to the lungs. Features of the embodiment of FIG. 1C corresponding to those described with reference FIG. 1A or 1B are referenced by the same reference numerals but ending with no letters instead of "A" or "B". Accordingly, the apparatus of FIG. 1C can be similar to the apparatus 1A, 1B of FIGS. 1A and 1B except as described differently below. In certain arrangements, the features of the apparatus 1C can be incorporated into the apparatus 1A of FIG. 1A and the apparatus 1B of FIG. 1B and the features of the apparatus 1A of FIG. 1A and the apparatus 1B of FIG. 1B can be incorporated into the apparatus 1C. Therefore, any combination of features between those described in FIGS. 1A, 1B, and 1C are within the scope of the instant disclosure.

With continued reference to FIG. 1C, the apparatus 1C can include a delivery device, which in the illustrated embodiment can be an endotracheal tube 40 having a distal end 404 and a proximal end 406. As noted above, in certain embodiments, the delivery device can comprise other devices configured to aid in interfacing with a patient to deliver liquid and/or gas to a patient's lungs such as a mask and/or nasal cannula and/or device allowing for immersion of the patient in a breathing liquid. The distal end 404 of the endotracheal tube 40 connects to the airway of the patient 2 for delivering a mixture of the gas and/or the cooled liquid to the patient 2. The distal end 404B of the endotracheal tube 40B can include one or more openings to a lumen(s) in the wall of the endotracheal tube to be connected to a device or switch that measures or reacts to a human or animal patient's airway pressure $P_{aw}$ 44B while the apparatus 1B delivers liquid and/or gas ventilation to the lungs of the patient 2. For example, a pressure sensor 400 an be located near the proximal end 406B of the endotracheal tube 40 for detecting pressure $P_{aw}$ 440 in an airway of the patient 2. The pressure sensor 400 can be optionally operatively connected to a main sensor tube 2210, which can be in turn coupled to a control unit 186 located in a driver assembly 10, which will be described in detail below. In the illustrated embodiment, the pressure sensor 400 can be part of a pair of balloon cuffs circumferentially disposed on the proximal end 406 of the endotracheal tube 40. The volume, or pressure, inside a forward cuff is capable of responding to the change in $P_{aw}$ 440 even when a mixture of liquid and gas is delivered to the patient. In one embodiment, the endotracheal tube 40 may comprise a separate lumen for the balloon cuffs. In one embodiment, the endotracheal tube 40 may comprise a lumen in the wall of the tube, or a separate tube disposed distally to receive pressure/vacuum inside the patient's lungs, and disposed proximally or elsewhere for a pressure sensor(s). In one embodiment, the endotracheal tube 40 may comprise a sensor within to sense pressure/vacuum in the patient's lungs.

Figure 9:
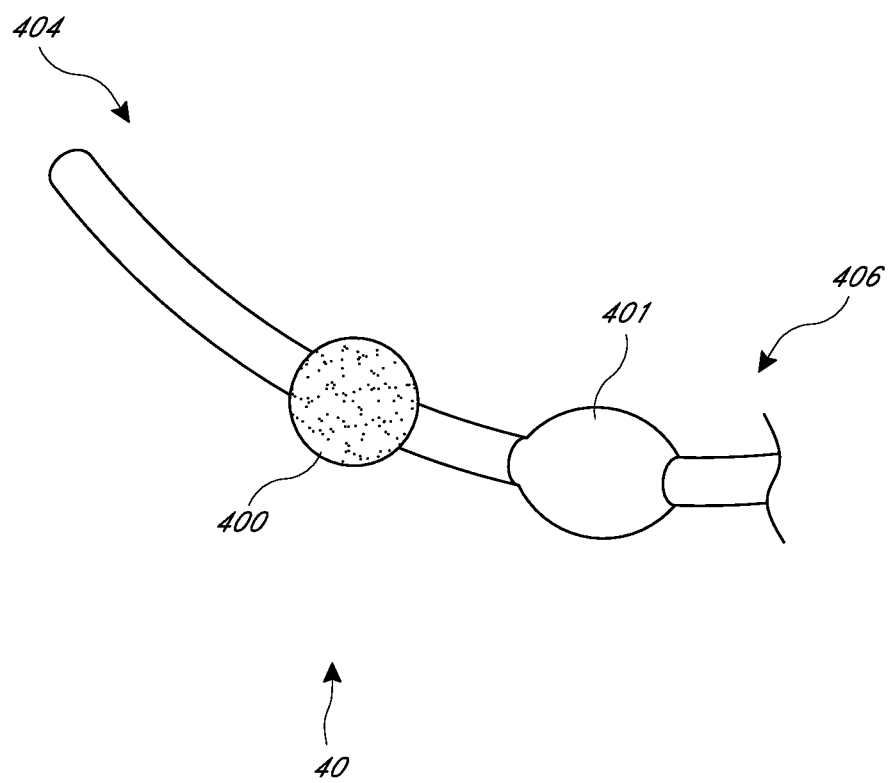
FIG. 9 illustrates an example embodiment of a distal end of an endotracheal tube in accordance with an embodiment of the present disclosure.

More specifically as shown in FIG. 9, in one embodiment, the cuff 401 of the endotracheal tube 40 can comprise an annular balloon like structure surrounding the distal end 404 of the endotracheal tube for the purpose of sealing against the inside of the trachea. An inflatable balloon device can advantageously supports passage through structures in the airway such as the vocal cords in a deflated state while providing a seal against leakage of ventilation fluids out of the airway, or unwanted fluids, solids, or secretions falling into the airway while inflated. While the illustrated cuff is preferred, in certain embodiments, cuffs and sealing structures of different configurations and structures can be used. In certain embodiments, commercially available endotracheal tubes with tapered cuffs, such as the cuff 401 shown in FIG. 9, can be adapted to be used with certain embodiments described herein. For example, a Sheridan Stat-Med tube or a Mallinckrodt™ EMT tube can be used. Also as shown in FIG. 9, a forward cuff 400 can include a pressure sensor capable of detecting pressure change in $P_{aw}$ 440. In some embodiments, the endotracheal tube 40 comprises a second in-wall lumen (not shown) open at the distal end of the tube and a luered or other port at the proximal end of the lumen parallel to a first, inflation lumen. The second lumen can extend between an inflation/deflation port and the cuff. The second lumen can be filled in and plugged distal to the cuff and can contain the pressure sensor. In some embodiments, the endotracheal tube 40 comprises multiple cuffs in tandem (not shown), with a distal seal for additional sealing if the proximal cuff is ruptured during procedures such as tonsillectomy or other in-trachea surgeries. In certain embodiments, the distal cuff is not required as a back-up seal in the trachea. The distal cuff can also be used to sense pressure in the patient's lungs. The distal cuff can also be subject to pressure in use. The pressure sensor 400 can be operatively connected to a main sensor tube (not illustrated), which is in turn can be coupled to a control unit 186 located contained in a driver assembly 10, which will be described in detail below.

The distal end 404B of the endotracheal tube 40B can include one or more openings to a lumen(s) in the wall of the endotracheal tube to be connected to a device or switch that measures or reacts to a human or animal patient's airway pressure $P_{aw}$ 44B while the apparatus 1B delivers liquid and/or gas ventilation to the lungs of the patient 2. FIG. 7B illustrates the endotracheal tube 40 in accordance with another embodiment of the present disclosure. In FIG. 7B, the endotracheal tube 40B can be constructed with a port 402 at or near the proximal end or as part of a connector attached at the proximal end for the purpose of observing pressure, adding medication, or withdrawing samples of fluid. The port may feature locking features, such as a luer fitting or locking luer geometry.

Figure 6A:
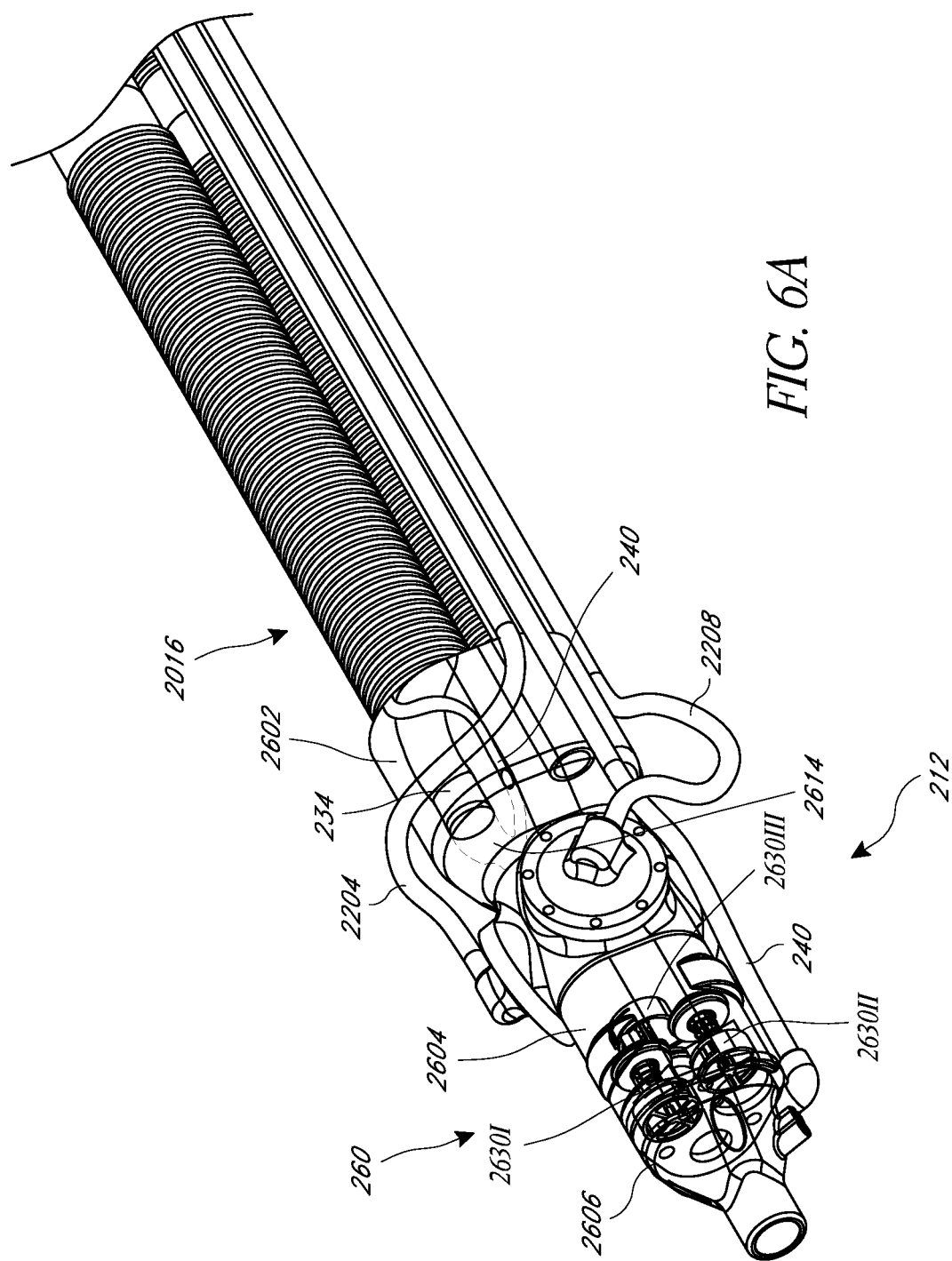
FIG. 6A is a perspective view of a distal end of the tube assembly in accordance with an example embodiment of the present disclosure.

With continued reference to FIGS. 1C and 7B, the proximal end 406 of the endotracheal tube can be connected to a distal nose portion 2606 of a distal flow connector 260 (shown in FIGS. 6B and 7B) directly or via any common commercially available airway connectors as desired. The distal flow connector 260 can have one or more channels for delivering and/or removing liquid or gas to and/or from the endotracheal tube 40 as well as features such as a pop-open device as an additional level of protection against patient over-pressure, or for access in an emergency situation requiring direct manual ventilation. In the illustrated embodiment as shown in FIGS. 6A and 7A, the distal flow connector 260 includes a liquid delivery channel 2608, a suction channel 2612, a gas delivery channel 2610 and a fluid recirculation channel 2614 as will be described below, the liquid and/or gas flowing through these channels can be controlled by one or more valves, which are placed in the channels.

Figure 7A:
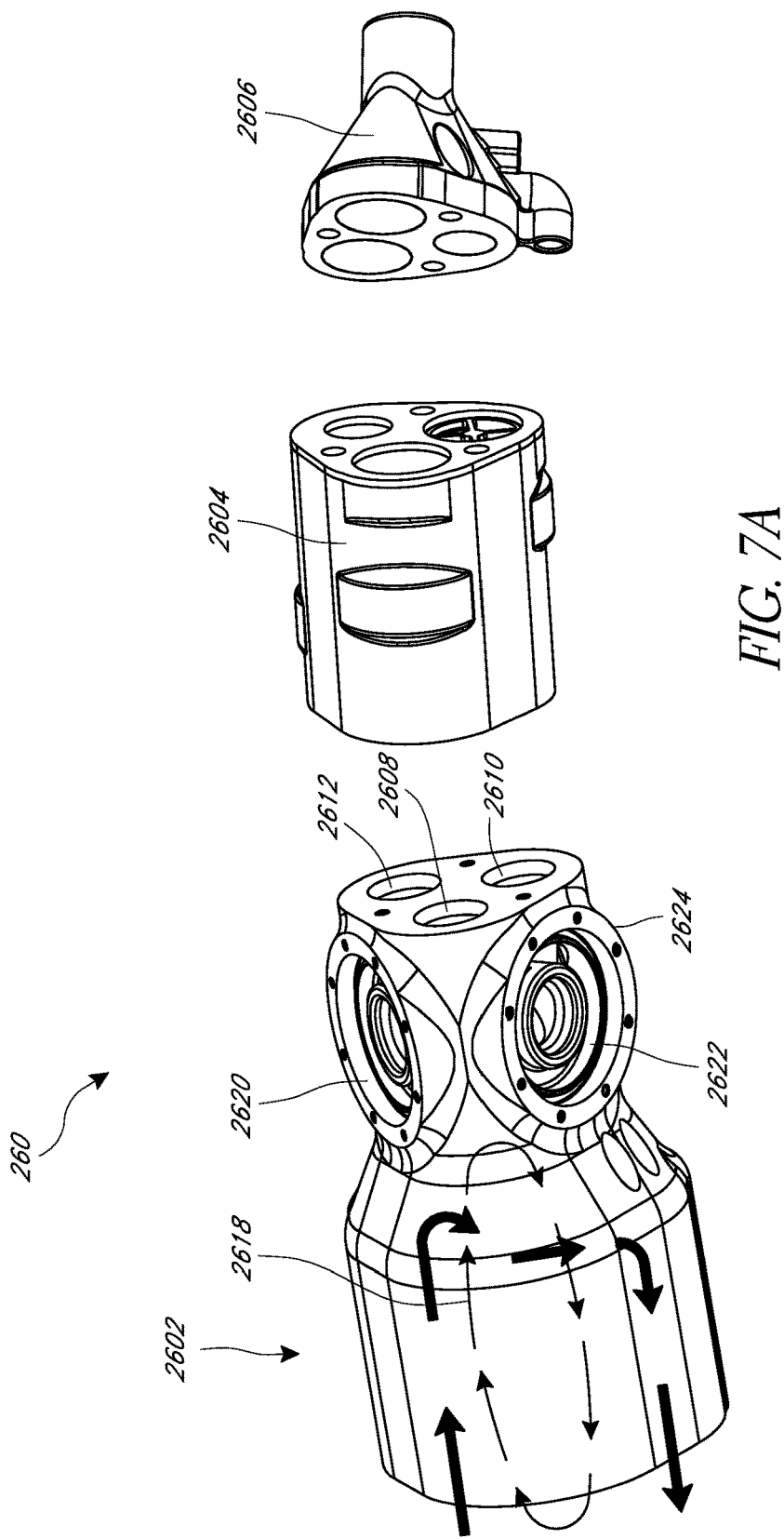
FIG. 7A illustrates an exploded view of a distal flow connector in accordance with an embodiment of the present disclosure.
Figure 7B:
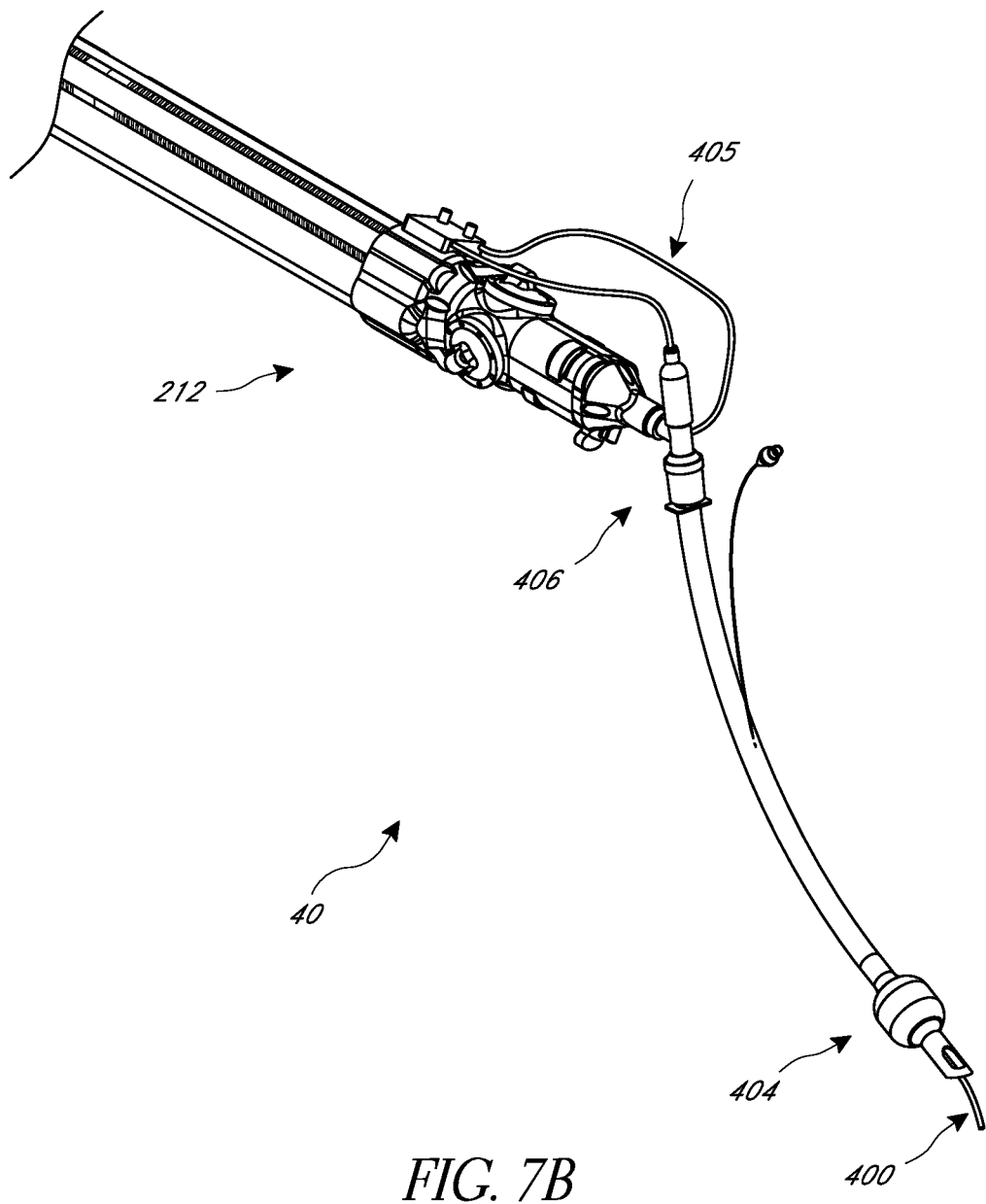
FIG. 7B illustrates a use of a distal flow connector with an endotracheal tube in accordance with an embodiment of the present disclosure.

FIG. 7A illustrates examples of components of the illustrated distal flow connector 260 in an exploded view. In the illustrated embodiment, the distal flow connector 260 can comprise a proximal portion 2602, a middle portion 2604, and the distal nose portion 2606. The distal nose portion 2606 of the distal flow connector can be suitable for connecting to the endotracheal tube 40, as shown in FIG. 7B. The proximal portion 2602 of the distal flow connector 260 can be an integral plastic part comprising the four channels plus co-axial cooling water flow in accordance with an embodiment of the present disclosure in order to make the distal flow connector more compact and easier to use. It is contemplated that the proximal portion 2602 can be 3D printed, which can be cheaper and faster than conventional machining or molding, and also can allow for easy update of design or adding customized configurations on a CAD model. Furthermore, machining and molding may not be feasible due to the complex structure of the proximal portion 2602 and the resistance to flow that would arise from features so configured as to be producible through means other than 3D printing. The middle portion 2604 of the distal flow connector can house a plurality of one-way check valves 2630I, 2630II, 2630III, also shown in the block diagram in FIG. 1D. The check valves act as additional safety features to ensure that the directions of flow in the distal flow connector 260 are as intended. As described earlier, the check valves can also provide for an automatic shutoff of gas by higher pressure liquid delivery, which can be timed as required to produce the desired mix of gas to liquid by a delay of delivery of the liquid to the proximal portion 2602. The proximal portion 2602 can also comprise a suction valve 2620, a gas delivery valve 2622, and a liquid delivery valve 2624.

In an exemplary embodiment, the gas delivery valve 2622 is located in the gas delivery channel 2610 and connects to a gas delivery pilot tube 2204. The liquid delivery valve 2624 is located in the liquid delivery channel 2608 and connects to a liquid delivery pilot tube 2206. The suction valve 2620 is located in the suction channel 2612 and connects to a suction pilot tube 2202. The distal flow connector 260 can additionally comprise the liquid recirculation (No. 8) valve 238 (not shown in FIG. 7A but shown in FIG. 5B) in the liquid recirculation channel 2614 and connects to a liquid recirculation pilot tube 2208. The suction, gas delivery, liquid delivery and recirculation pilot tubes, 2202, 2204, 2206, 2208, and the main sensor tube 2210 all extend along a tube assembly 20 from a distal end 212 to a proximal end 210. In modified embodiments, the liquid recirculation valve 238 can be located at other locations. For example, the liquid recirculation (No. 8) valve 238 can be located between the liquid recirculation port 130 and the liquid recirculation tube 240. In some embodiments, the valves 2620, 2622, 2624 can be two-way exhalation valves. In the illustrated embodiment, each of the valves 2620, 2622, 2624 on the proximal portion 2602 can comprise a diaphragm 2626 and a cap 2828. The diaphragm 2626 is designed to "oil can" to enhance flow.

With continued reference to FIG. 1C, the distal flow connector 260 can be connected to the distal end 212 of the tube assembly 20. In one embodiment, the tube assembly 20 includes one or more tubes that correspond to the channels in the distal flow connector 260. In the illustrated embodiment, the tube assembly 20 is generally flexible and can have a length of about 6 feet. In one arrangement as shown in FIGS. 4A-6A, the tube assembly 20 includes a suction tube 230 that can be in fluid communication with the suction channel 2612 of the distal flow connector. The tube assembly 20 can also include a gas delivery tube 232 that can be in fluid communication with the gas delivery channel 2610, seen in FIG. 7A, of the distal flow connector 260. The tube assembly 20 can also include a liquid delivery tube 234 that can be in fluid communication with the liquid delivery channel 2608, seen in FIG. 7A, of the distal flow connector. The tube assembly can also include a liquid recirculation tube 240 in fluid communication with the liquid recirculation channel 2614 of the distal flow connector.

As shown in FIG. 1C, the tube assembly 20 can include a heat exchange assembly 200 (more clearly shown in FIGS. 1D and 5A) on a distal portion of the tube assembly 20. The heat exchange assembly 200 can comprise an outer tube 2006, a proximal flow connector 250, at least a portion of the liquid delivery tube 234, and at least a portion of the liquid recirculation tube 240. The outer tube 2006 can provide thermal insulation (and containment) to the cold water 302, the liquid delivery tube 234, and the liquid recirculation tube 240 inside the outer tube 2006. As shown in FIG. 6A, a distal end 2016 of the heat exchange assembly 200 can fit into the proximal portion 2602 of the distal flow connector 260. A cold water inlet pipe 242 is connected to the proximal portion 2602 of the distal flow connector 260 such that the cold water 302 enters the heat exchange assembly 200 at its distal end 2016. As shown in FIG. 6B, the cold water 302 can flow in the direction 2616. The direction 2616 allows better cooling efficiency. One of ordinary skill in the art may appreciate that the water can also flow in an opposite direction. The cold water 302 cools the liquid in both the liquid delivery tube 234 and the liquid recirculation tube 240 as the cold water 302 flows from the distal end 2016 towards a proximal end 2014 of the heat exchange assembly to return to a cold water bath 300. Furthermore, the liquid delivery tube 234 and the liquid recirculation tube 240 can be twisted into a double helix 2012 inside the outer tube 2006 in accordance with one embodiment of the present disclosure. In some embodiments, the liquid delivery tube 234 and the liquid recirculation tube 240 are also corrugated. As shown in FIGS. 1C and 7B, temperature probe 405 can be connected at the proximal end of the endotracheal tube 40 for readout on a thermometer display or recording device of the measured temperature of the fluids entering and exiting the lungs.

In addition to the advantages described above for providing heat exchange at the tube assembly, another advantage of the heat exchange assembly in accordance with the illustrated embodiment is to maximize and/or increase heat exchange and the resulting cooling and/or heating. Specifically, the illustrated double helix configuration and/or using corrugated tubes can provide more surface area and/or turbulence and thus additional cooling time through increased surface contact for the liquid without making the tube assembly excessively long and cumbersome to use. Furthermore, having the liquid recirculation tube 240 as part of the heat exchange assembly 200 can allow additional cooling of the liquid when it is being circulated in a closed loop formed by the liquid delivery tube 234, the liquid recirculation tube 240, and a canister 160 (or fluid reservoir) comprising a reservoir of the liquid located in a driver assembly 10. In certain embodiments, the liquid delivery tube 234 and/or the liquid recirculation tube 240 at a proximal end 210 of the tube assembly (shown in FIG. 4B), that is, before they become part of the heat exchange assembly 200, can be wrapped with an insulating material 270 to help the liquid stay cooled for a longer period of time.

Figure 4A:
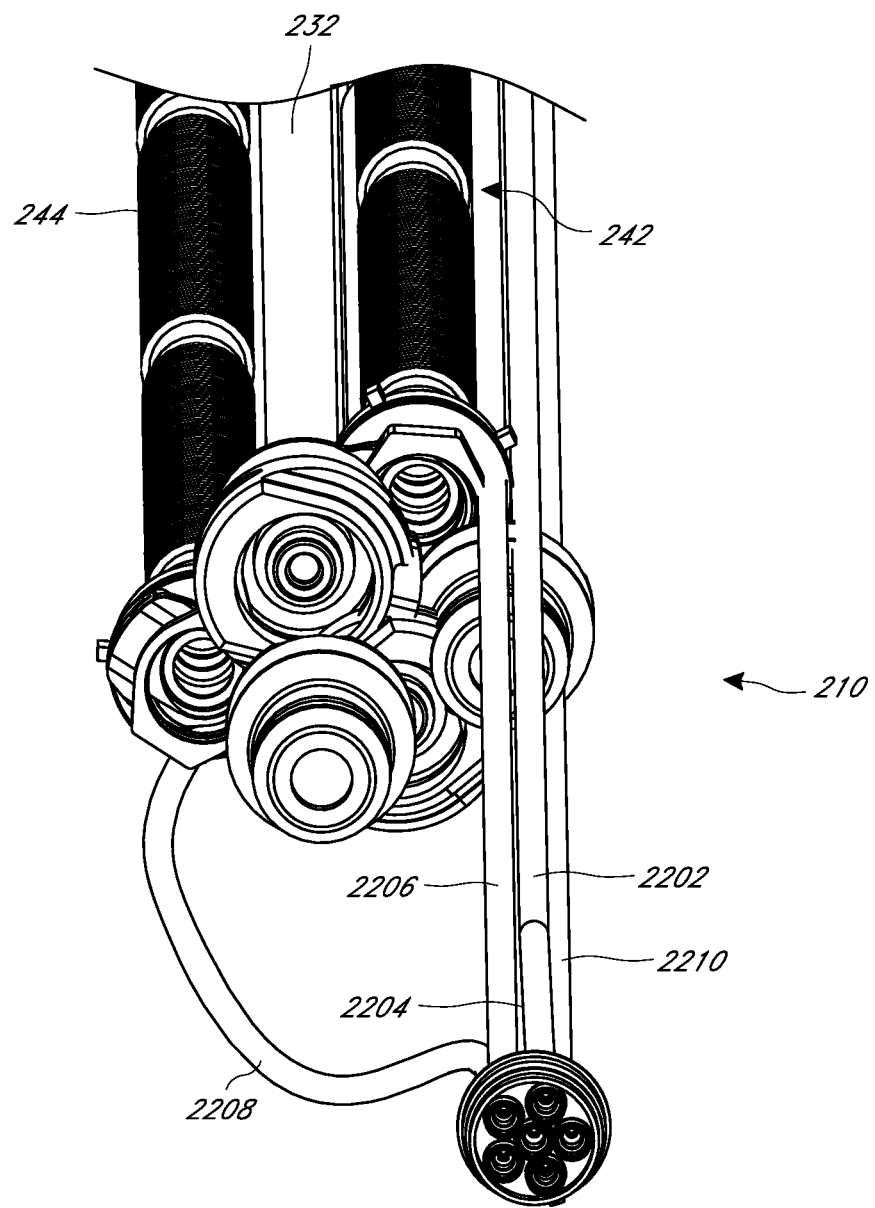
FIG. 4A illustrates a top perspective view of a proximal end of the tube assembly in accordance with an embodiment of the present disclosure.
Figure 5A:
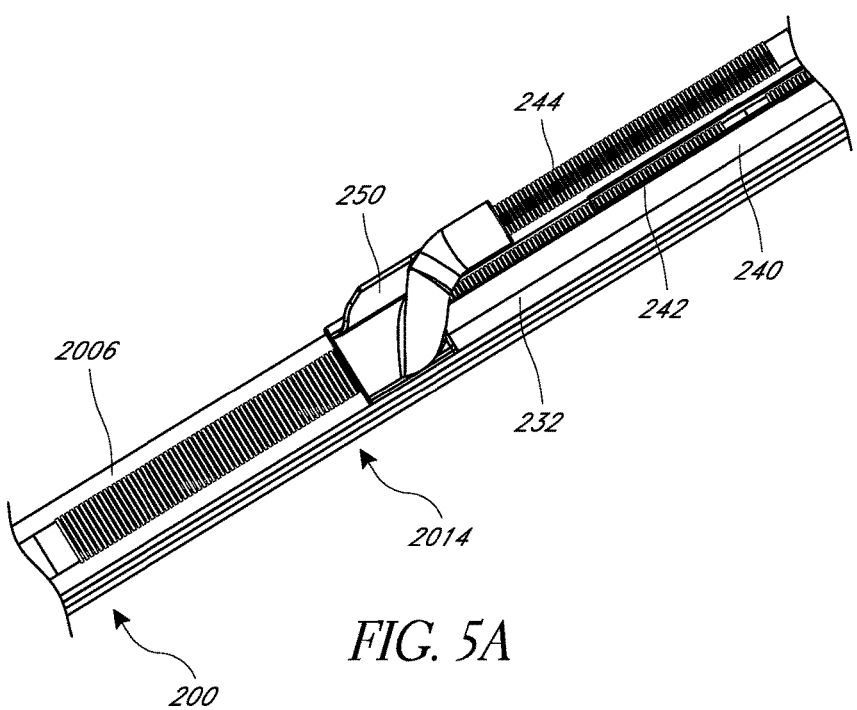
FIG. 5A is a perspective view of a proximal end of a heat exchange assembly of the tube assembly in accordance with an example embodiment of the present disclosure.
Figure 6B:
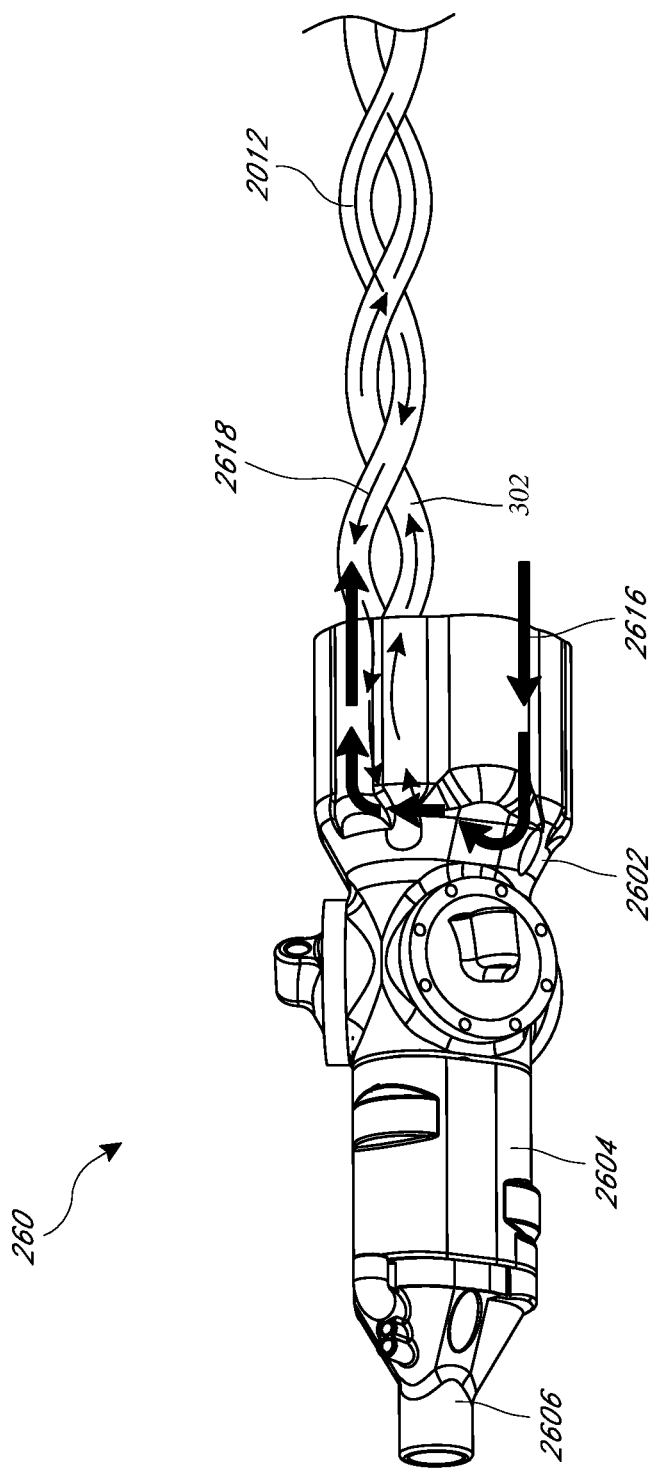
FIG. 6B illustrates a perspective view of a proximal part of an example distal flow connector connected to a liquid delivery tube and a liquid recirculation tube arranged in a double helix configuration in accordance with an example embodiment of the present disclosure.

FIG. 5A illustrates the proximal end 2014 of the heat exchange assembly 200. The proximal flow connector 250 of the heat exchange assembly 200 can connect to a cold water outlet pipe 244. The cold water inlet pipe 242 and a cold water outlet pipe 244 (shown in FIG. 4A) can be connected to a cold water bath assembly 30 for cooling the liquid 50 and/or the gas. The cold water bath assembly 30 can have a cold water bath 300 containing cold water 302, a water bath outflow tube 304 connected to the tube assembly 20 at the cold water inlet pipe 242, shown in FIG. 4A, and a water bath inflow tube 306 connected to the tube assembly 20 at the cold water outlet pipe 244, shown in FIGS. 1C and 4A. In an embodiment as shown in FIGS. 1C-1D, the water bath inflow tube 306, which is in fluid communication with the cold water outlet pipe 244, connects to a lid (not shown) of the cold water bath 300. The water bath outflow tube 304, which is in fluid communication with the cold water inlet pipe 242, connects to a turbine 310 that can drive the cold water 302 from the cold water bath 300. During operation of the apparatus 1C, cold water 302 flows in a loop from the cold water bath 300 through the cold water inlet pipe 242 and the cold water outlet pipe 244 and back to the cold water bath 300. The cold water bath 300 may contain ice or other materials suitable for cooling the water that is known or obvious to a person of ordinary skill in the art. Instead of having a cold water bath built into a driver assembly for heat exchange, the apparatus 1C reduces an overall size and weight of the driver assembly 10 by having a stand-alone cold water bath, which can be obtained separately at a patient site instead of having to be transported to the patient site as part of the apparatus. In another arrangement, a common ice cooler can be used as the transportation case for the driver and double as the cold water bath. The ice cooler can be a common ice chest of flyable luggage size so that the apparatus 1C can advantageously be transported on a commercial air craft.

Figure 5B:
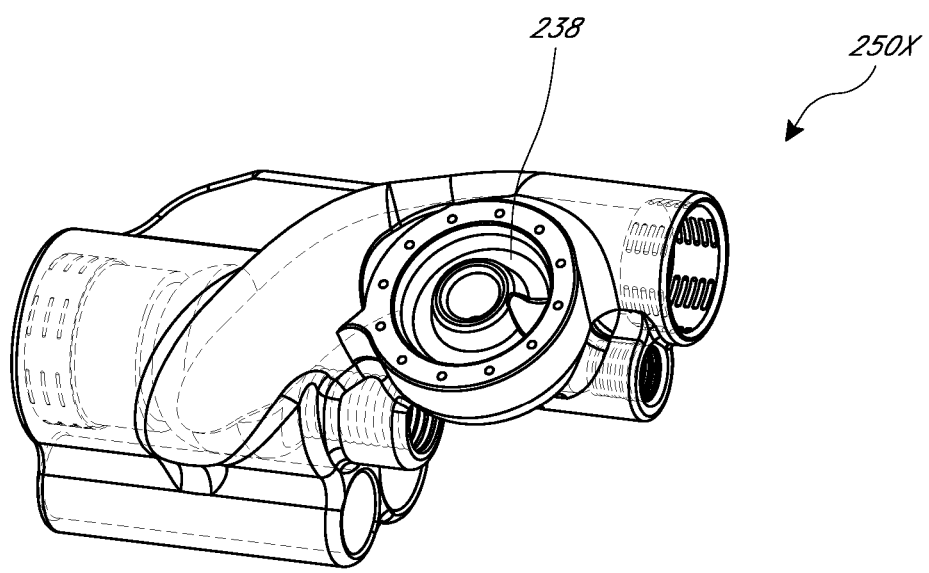
FIG. 5B illustrates a perspective view of a proximal flow connector in accordance with another example embodiment of the present disclosure.

FIG. 5B provides another embodiment of a proximal flow connector 250X having features similar to those of the proximal flow connector 250. The proximal flow connector 250X additionally comprises the liquid recirculation (No. 8) valve 238. Having the liquid recirculation valve 238 on the proximal flow connector 250X advantageously reduces the overall size of the tube assembly 20. As described above, updating the design of the proximal flow connector to incorporate the liquid recirculation valve 238 can be done efficiently on a 3D CAD model.

Figure 4B:
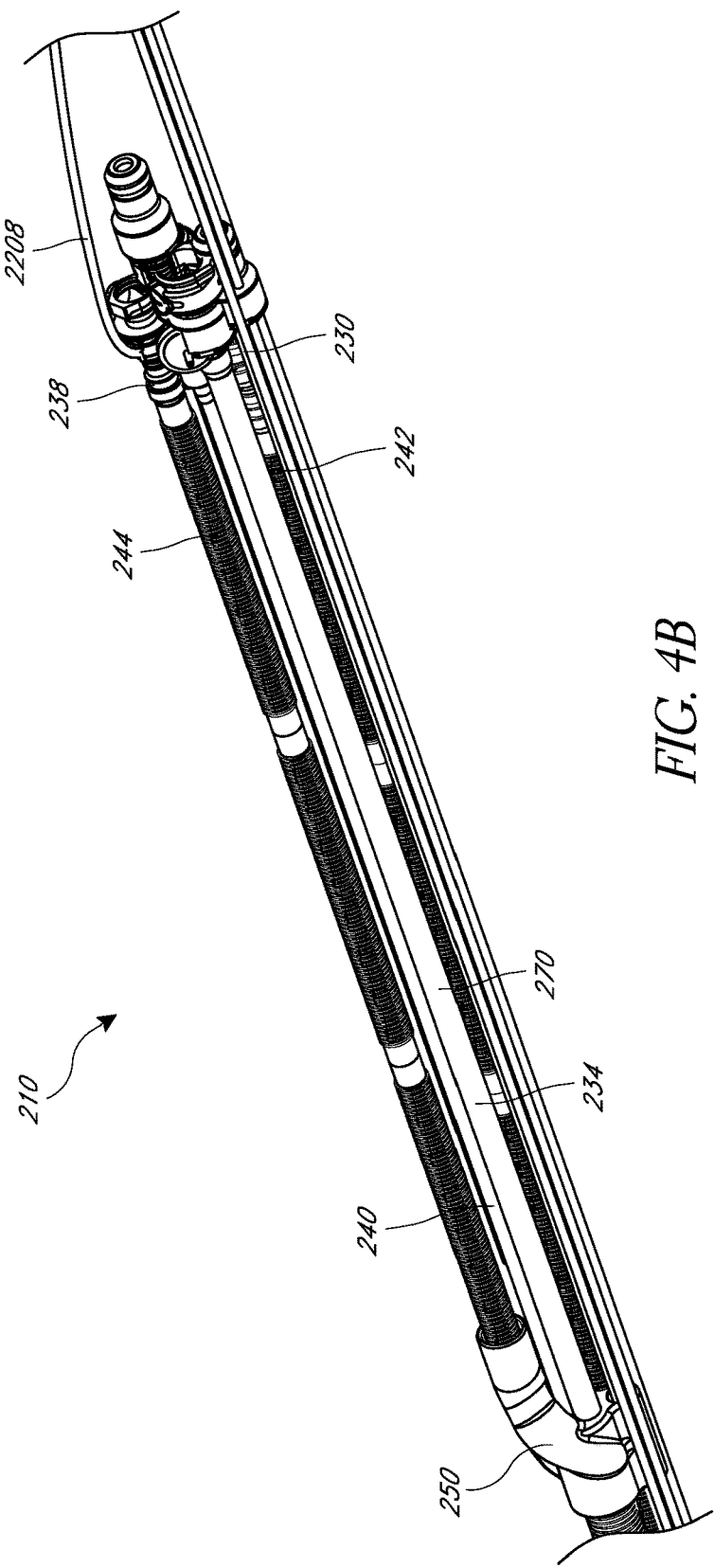
FIG. 4B illustrates a side perspective view of the proximal end of the tube assembly in FIG. 4A.
Figure 4C:
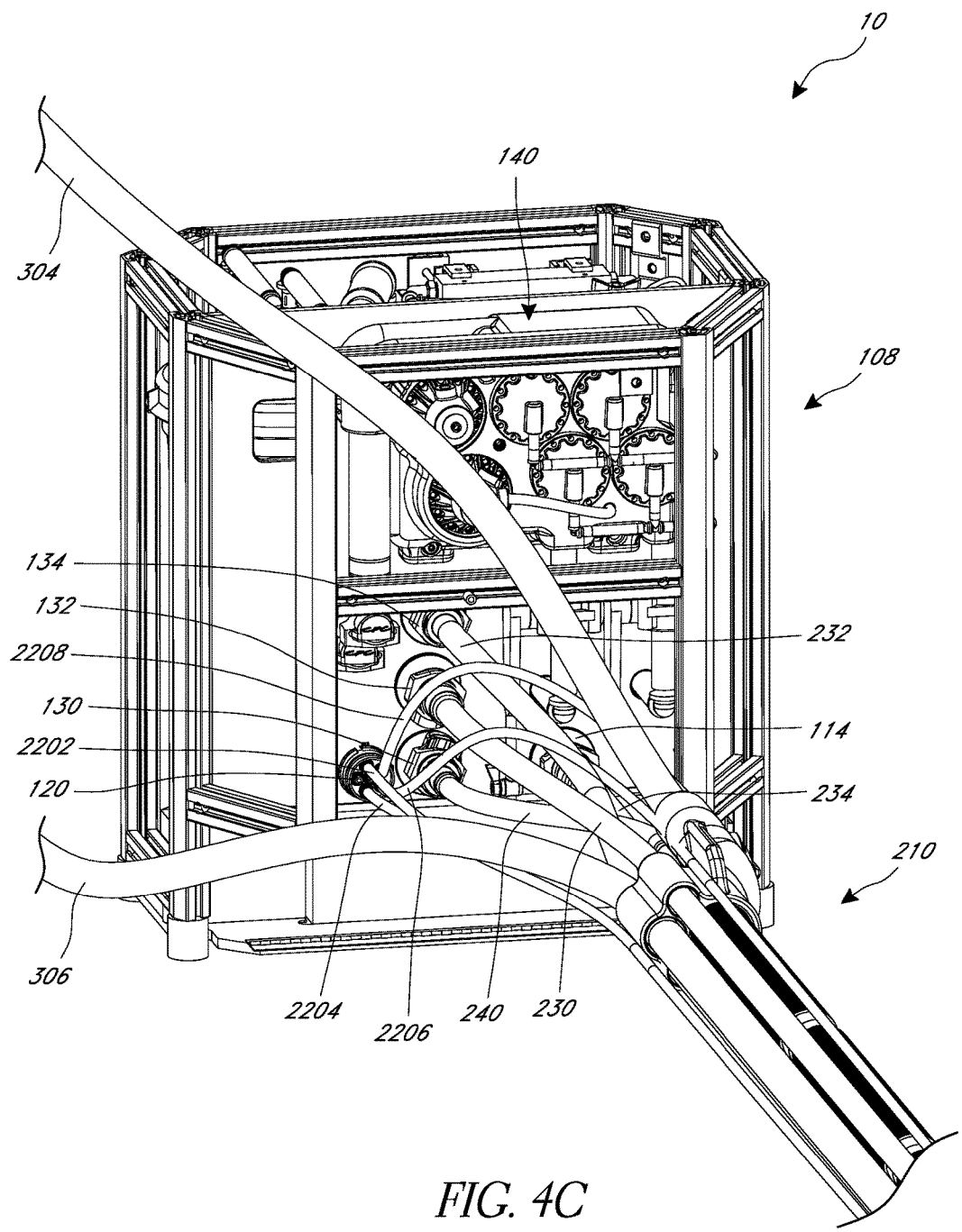
FIG. 4C illustrate a perspective view of the proximal end of the tube assembly in FIG. 4A connected to the driver assembly in FIG. 2A.

Turning to a proximal end 210 of the tube assembly 20 as illustrated in FIG. 4A and FIG. 4B, the proximal end 210 of the tube assembly connects to the driver assembly 10 through an opening 110 of the driver assembly. FIG. 4C illustrate how the proximal end 210 of the tube assembly connects to the driver assembly 10. As shown in FIG. 4C, the liquid delivery tube 234 is in fluid communication with a liquid-delivery port 114 (also shown in FIG. 2C) on the driver assembly 10, the suction tube 230 is in fluid communication with a suction port 132 (also shown in FIG. 2C) on the driver assembly 10, the gas delivery tube 232 is in fluid communication with an gas delivery port 134 (also shown in FIG. 2C) on the driver assembly 10, and the liquid recirculation tube 240 is in fluid communication with a liquid recirculation port 130 (also shown in FIG. 2C) on the driver assembly 10. The proximal end 210 of the tube assembly 20 can further comprise a plurality of pilot tubes configured to be connected to a circuit connection port 120 (also shown in FIG. 2C) on the driver assembly 10. The plurality of pilot tubes can include the suction pilot tube 2202, the gas delivery pilot tube 2204, the liquid delivery pilot tube 2206, the liquid recirculation pilot tube 2208, and the main sensor tube 2210 in one connector to facilitate connection of the control tubes to their respective pilot lines ending at a circuit connection port 120 on the driver assembly 10. The circuit connection port 120 may be eliminated in select embodiments for reduced cost and weight and replaced with a quick disconnect (QD) fitting.

Figure 2A:
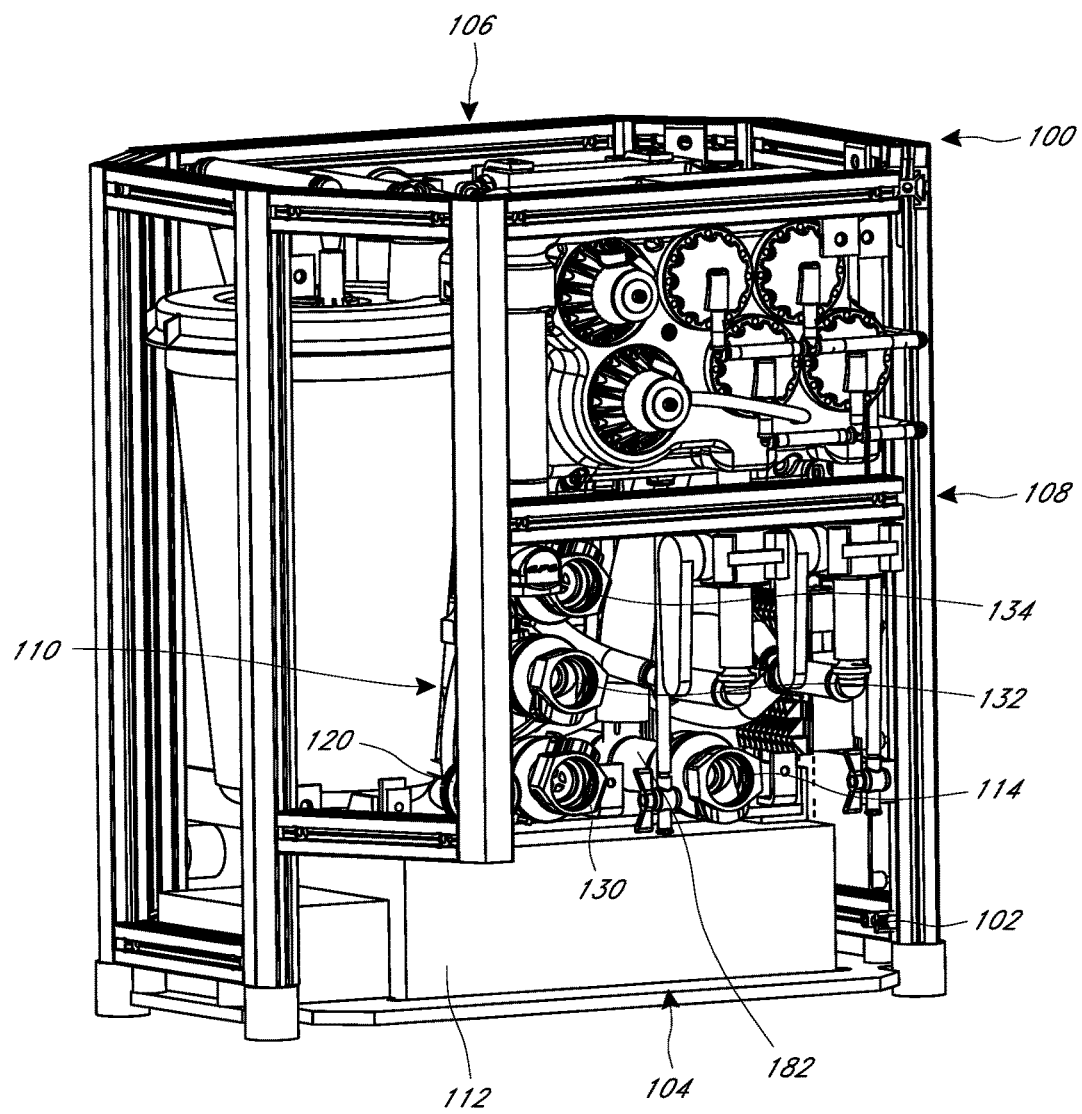
FIG. 2A illustrates a front perspective view of an example embodiment of a driver assembly in FIGS. 1C-1D.

Turning to an example embodiment of the driver assembly 10 as shown in FIG. 2A, the driver assembly 10 can be encased in an octagonal-shaped protective see-through cage-like frame 108. The ability to see through the frame 108 can advantageously provide visual confirmation that the apparatus 1C is running as intended or that the apparatus 1C is malfunctioning. The ability to see through the frame in some embodiments, the octagonal shape of the frame 108 fits into a flyable-sized off-the-shelf cooler. The driver assembly 10 has a front side 104 and a back side 106. The driver assembly 10 also has an upper side 100 and a lower side 102. The cage-like frame 108 has the opening 110 located on the front side 104 of the driver assembly towards the lower side 102 of the driver assembly, leaving exposed on the front side 104 a power source 112 located at the lower side 102 of the driver assembly, the liquid delivery port 114, the circuit connection port 120, the liquid recirculation port 130, the suction port 132, and the gas delivery port 134. It is contemplated that the apparatus 1C can be operated by both a DC power source, such as batteries and back up batteries using a back-up battery switch, and an AC to DC power supply, by plugging into a AC wall outlet, in accordance with an embodiment of the present disclosure. Dual power source allow the apparatus to be used for potentially unlimited amount of time when powered by the AC wall outlet. When in transport or when no AC wall outlet is available, operation from the battery power is possible. In certain arrangements, typically one hour of continuous operation is possible with a properly sized battery. A similarly sized auxiliary battery could power the system an additional hour. In certain arrangements, batteries can be swapped and charged using a quick charge method in one hour and can be swapped back into service without interruption to the ventilation procedure.

Figure 2B:
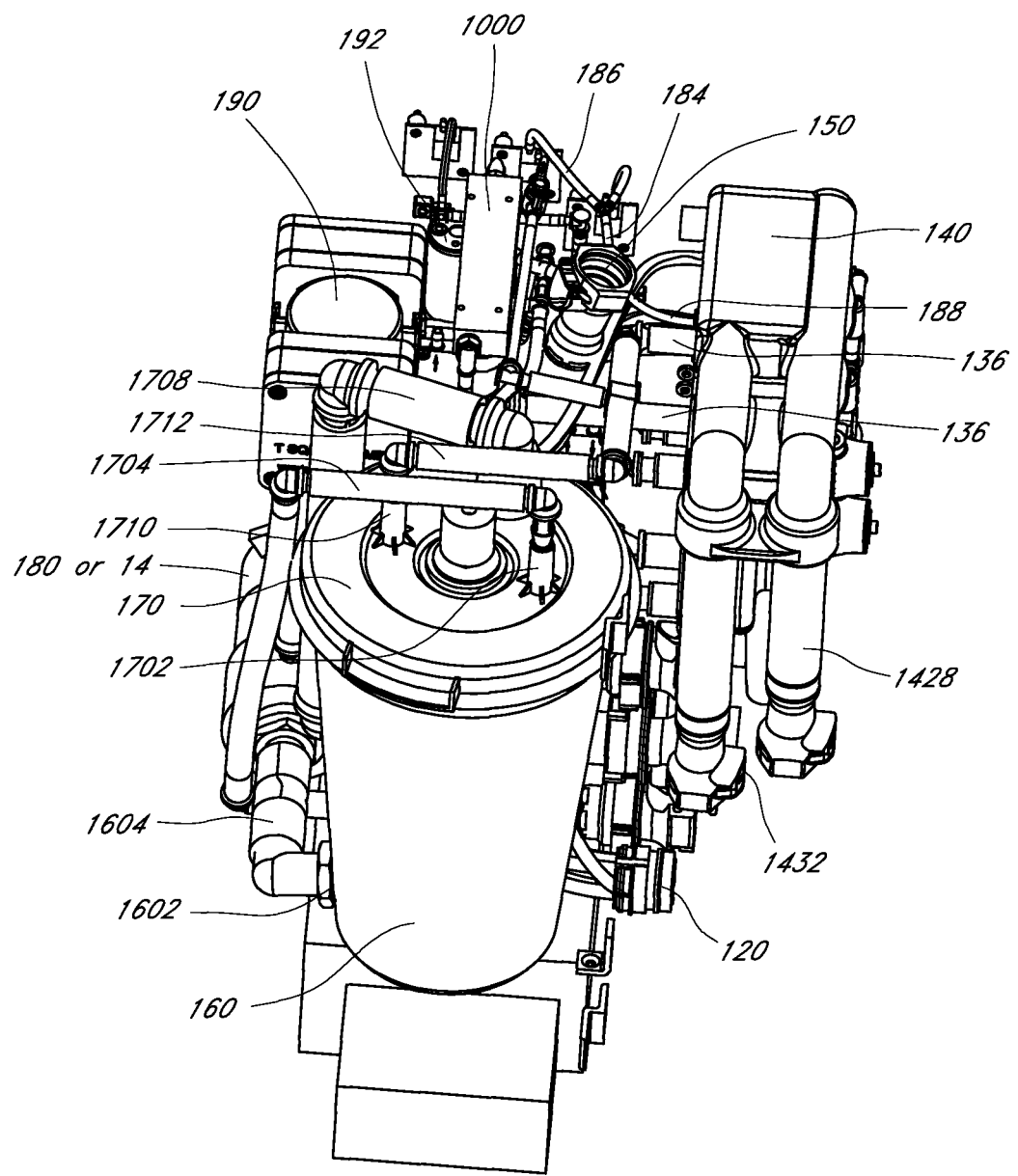
FIG. 2B illustrates a top perspective view of the driver assembly in FIGS. 1C and 1D without a protective frame.
Figure 2C:
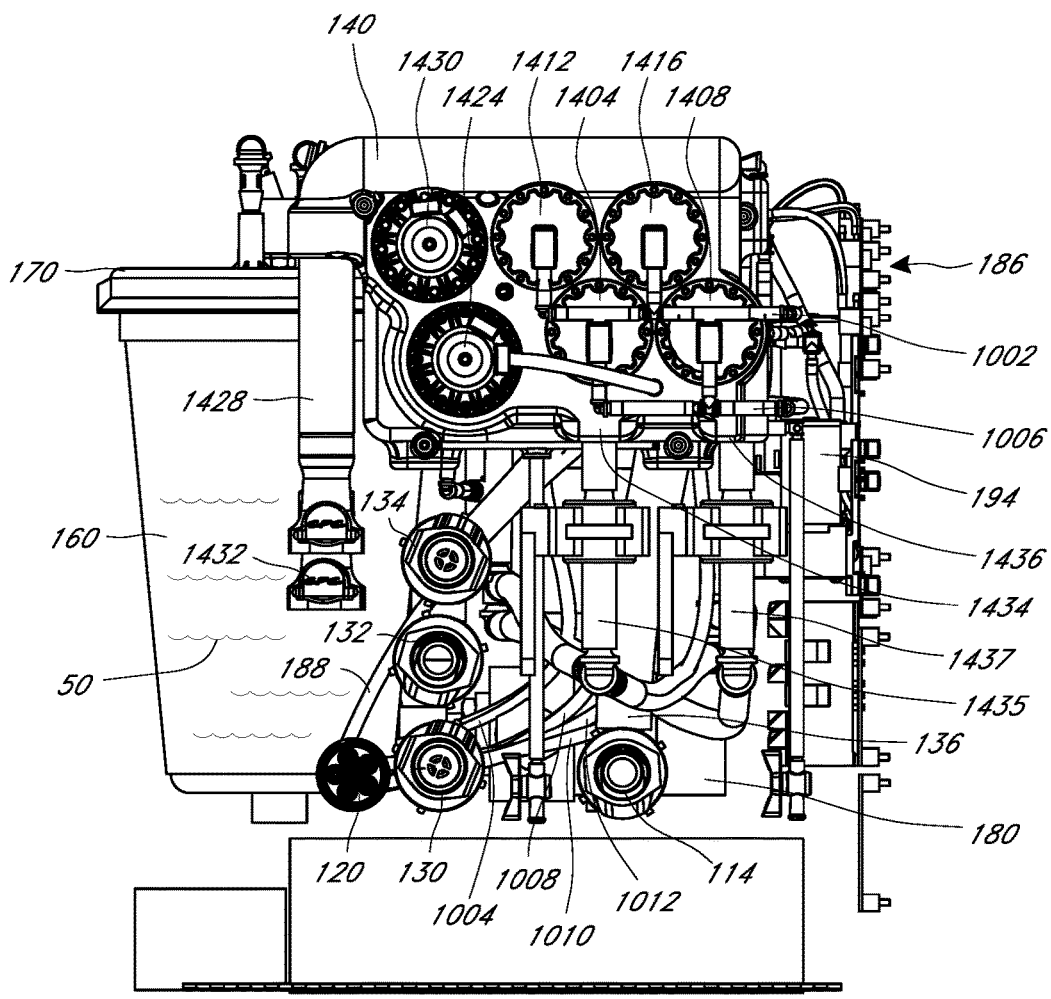
FIG. 2C illustrates a front view of the driver assembly in FIGS. 1C and 1D without the protective frame.

With continued reference to FIGS. 2C and 4C, the main sensor tube 2210 can be operatively coupled to the control unit 186 located within the driver assembly 10 via the circuit connection port 120. The control unit 186 can comprise a state controller and a plurality of boards with pressure/vacuum sensing chips mounted on them. The control unit 186 can be configured to decide whether the apparatus should be in the inhale phase or the exhale phase according to information from the pressure sensor 400 via the main sensor tube 2210. The apparatus 1C can be configured to avoid response lags, inaccuracies in pressure sending due to elevation changes of the driver assembly relative to the patient when there is a liquid column in the main sensor tube 2210. One of ordinary skill in the art may appreciate that other forms of communication between the pressure sensor 400 and the control unit 186 can be used. The control unit 186 outputs instructions to control the flow of the liquid and gas between the tube assembly 20 and the endotracheal tube 40 by controlling opening and closing of the one or more two-way valves 2620, 2622, 2624, 238 described above and shown in FIGS. 5B and 7A. In the illustrated embodiment, opening and closing the valves 2620, 2622, 2624, 238 can be done by smaller pilot valves 1018, 1020, 1022, 1024 (shown in FIG. 1D) and/or three way solenoid valves (also controlled by the control unit 186 and described below; shown in FIG. 10B) located in the driver assembly 10. The pilot valves and solenoid can be four pairs of 2-way valves. The pilot valves can also be four 3-way valves.

In an exemplary embodiment, valves described herein may include a diaphragm. FIG. 12 illustrates an exemplary contoured diaphragm to create a sealing surface for the valve. As shown, the valve is normally open, and closes with the application of pressure. However, the valve may be normally closed. The valve may also be opened with pressure and/or opened or closed with a vacuum. As shown, having a normally open valve that closes with a change in pressure permits one of the pressure sources to be removed from the system. For instance, the vacuum pump may be removed, and a single pump used to control the valves. In this case, the valve may be controlled by applying a greater than atmospheric pressure to close the valve, and applying atmospheric pressure or simply opening the line to atmosphere to open the valve. As illustrated in the cross section of FIG. 12A, the valve includes a diaphragm in a normally open configuration that permits to and from flow between a first opening and a second opening. As shown, the first and second openings are in a common plane and positioned on the same side of the diaphragm. The valve diaphragm in a relaxed or normal configuration is in contact with the plane containing the first and second opening at an outer perimeter of the diaphragm and out of contact with the plane on an interior region of the diaphragm. For example, the diaphragm may be curved or dome shaped. The valve may include a control opening on an opposite side of the diaphragm from the first and second opening. The control opening configured to supply pressure or vacuum or remove pressure or vacuum to control the position of the diaphragm, such as in either a closed or open configuration.

When the pressure in the airway $P_{aw}$ 440, of FIG. 1D, is below a predetermined maximum threshold pressure, the apparatus 1C can operate in the inhale phase to deliver the gas and/or the cooled liquid 50 to the lungs of the patient 2 with the gas delivery (No. 5) valve 2622 and/or the liquid delivery (No. 6) valve 2624 open and the suction (No. 10) valve 2620 and the recirculation (No. 8) valve 238 closed. In certain example embodiments, in the threshold pressure can be approximately 30 cm water (cm $H_2O$). In certain embodiments, the threshold pressure can be greater than or less than approximately 30 cm water (cm $H_2O$). For example, as described below, in certain embodiments a band around the chest can be used in combination with an embodiment of the apparatus described herein. In such embodiments, it is anticipated that a higher threshold pressure can be used. Once the pressure sensor 400 detects the predetermined maximum threshold pressure, the apparatus 1C switches to the exhale phase to withdraw the gas and the liquid 50 from lungs of the patient 2 via the endotracheal tube 40 with the suction valve 2620 open and the gas delivery valve 2622 and the liquid delivery valve 2624 closed until some preset vacuum, or minimum threshold pressure, is reached. In certain example embodiments, in the preset vacuum can be approximately negative 30 cm water (cm $H_2O$). In certain embodiments, the threshold pressure can be greater than or less than approximately negative 30 cm water (cm $H_2O$). The recirculation valve 238 is also open during the exhale phase to allow the liquid 50 to flow in the closed loop 2618 as shown in FIG. 6B and back to the canister 160. The preset vacuum causes the apparatus 1C to switch back to the inhale phase. As described above, the predetermined threshold pressure can be achieved in a variety of circumstances.

In some embodiments, the device can be equipped with an optional second control 187 (shown in FIG. 1D) configured for use with CPR by synchronizing the second control 187 with the manual or automated CPR. The second control 187 can be a small bag such as a blood pressure cuff that is pneumatically pressurized and compressed by a band or piston of an automated CPR device or is compressed between hands of a human CPR provider and the patient's chest. In certain embodiments, the second control 187 can be a tension sensor in a band type and/or automated CPR device (such as Zoll AutoPulse®), or driven by the pressure of a piston-cylinder arrangement (such as Michigan Instruments "Thumper") or other pneumatic, force, or pressure sensing means of determining synchronization with an automated or manual CPR procedure. The predetermined threshold pressure and/or the preset vacuum can be adjusted and/or set by the user of the apparatus.

The liquid delivery tube 234 of the tube assembly can be operatively coupled to a canister 160 (shown in FIGS. 2A-2D) located within the driver assembly 10 which can comprise a reservoir of liquid and/or a pump for delivering the fluid from the canister 160 to the liquid delivery tube 243. In a similar manner, the suction tube 230 and the liquid recirculation tube 240 of the tube assembly can be operatively coupled to the canister 160. As shown in FIG. 2B, the canister 160 is air-sealed with a canister lid 170. The canister 160 can be located behind and to the left of the circuit manifold 140. The canister 160 can be located at other locations on other embodiments. The canister 160 contains the liquid 50 and has a liquid delivery opening 1602 near a bottom of the canister 160. The liquid delivery opening 1602 is in fluid communication with a turbine pump 180 (shown in FIG. 2C) via a turbine pump connecting tube 1604, and the turbine pump 180 in turn connects to one end of a liquid delivery pipe 182, illustrated in FIG. 2A. An opposite end of the liquid delivery pipe 182 terminates at the liquid delivery port 114 of FIG. 2A for connecting with the fluid delivery tube 234. When the apparatus 1C is in an inhale phase, the liquid 50 can leave the canister 160 under a pressure (discussed below) to be delivered to the patient 2. Similar to the turbine pump 18 in FIG. 1B, the turbine pump 180 can pump the liquid 50 from the canister 160 to the liquid delivery pipe 182 and eventually to the heat exchange assembly 200 faster and could aerate the fluid 50 as it goes through the turbine. Additional liquid may be added through a refill port 150 which is also coupled to the turbine pump 180.

Figure 2D:
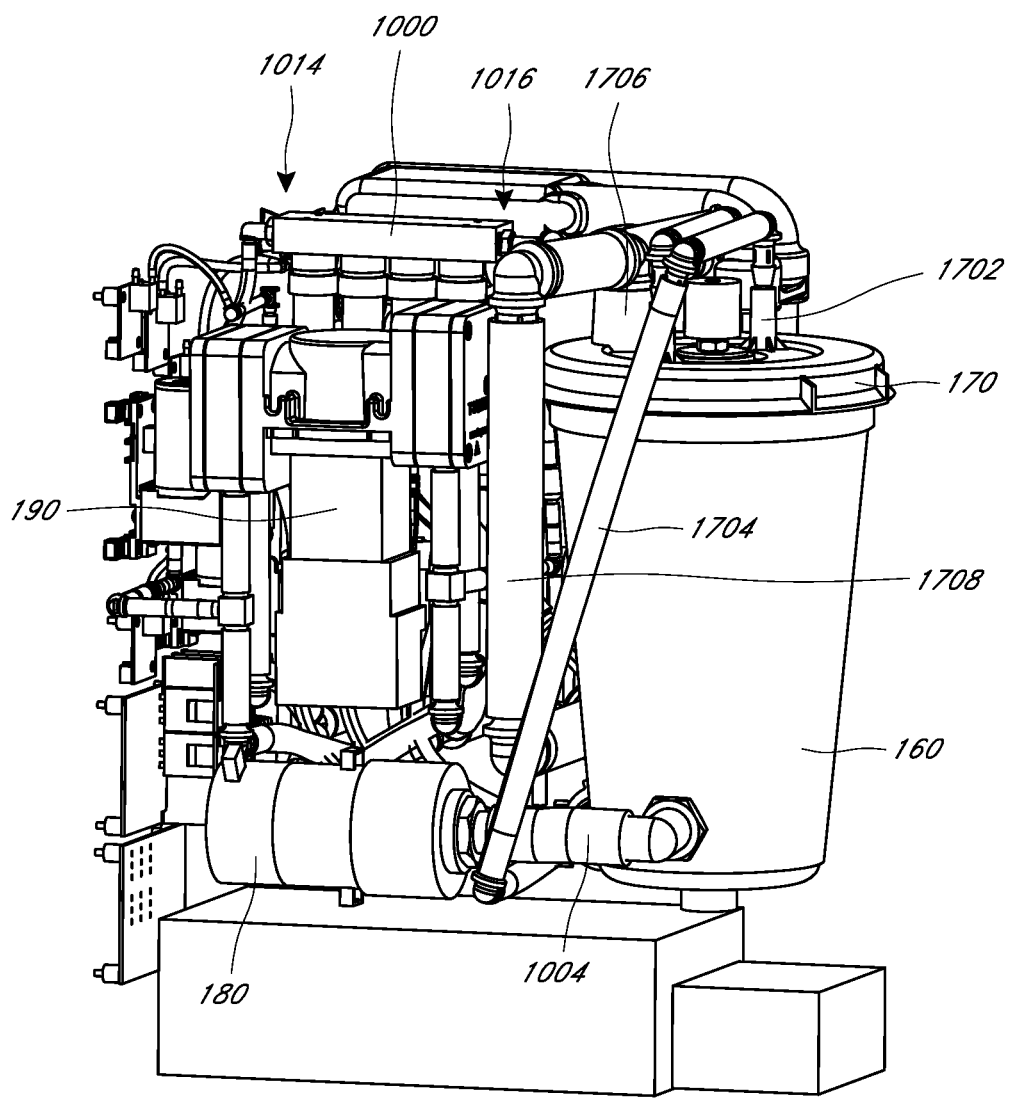
FIG. 2D illustrates a back view of the driver assembly in FIGS. 1C and 1D without the protective frame.

The canister lid 170 can also have a liquid recirculation opening 1702, a suction opening 1706 illustrated in FIG. 2D, and a pressure control opening 1710. The liquid recirculation opening 1702 is in fluid communication with a liquid recirculation return tube 1704, which in turn connects to the liquid recirculation port 130 for connecting to the liquid recirculation tube 240. The suction opening 1706 is in fluid communication with a canister suction tube 1708, which in turn connects to the suction port 132 for connecting with the suction tube 230. The pressure control opening 1710 connects to the canister pressure control tube 1712. When the apparatus 1C is in an exhale phase, the fluid 50 in the liquid recirculation return tube 1704 and a mixture of the gas and the fluid 50 withdrawn from the lungs of the patient 2 are returned to the canister 160. An advantage of returning the gas withdrawn from the patient into the sealed canister is to control exhaled air being released into the room and capture exhaled air which could be toxic, flammable (such as anesthetics), or contains infectious bacteria or viruses. Keeping the exhaled air contained protects medical personnel or first aid providers when rescuing biological or chemical event victims using a fluid for lung lavage. Liquid samples may also be saved in the canister 160 for analysis. Air samples can be taken from element 1428.

Turning to FIG. 2B, which illustrates the driver assembly 10 in FIG. 2A without the protective frame 108, the driver assembly 10 further comprises a pressure/vacuum circuit manifold 140. The pressure/vacuum circuit manifold 140 can be located toward the front side 104 of the driver assembly. One of ordinary skill in the art may appreciate that the manifold 140 can be placed at other locations. The pressure/vacuum circuit manifold 140 can be an integral circuit that houses a plurality of valves, shown in greater detail in FIG. 3B. An embodiment of the present disclosure having the one-part circuit manifold 140 has the advantage of providing efficient flow paths and reducing the size of the driver assembly, making the apparatus more portable. It is contemplated that the one-part circuit manifold 140 can be 3D printed to save cost and time for making the manifold. The printed flow paths in a 3D printed manifold can be readily optimized for flow characteristics. With 3D modeling, it will also be easy to change and update designs of the manifold, or make customized configurations thereof. Conventional machining and molding may not even be feasible due to the complex flow paths of the manifold 140 and could result in less optimal flow.

Figure 3A:
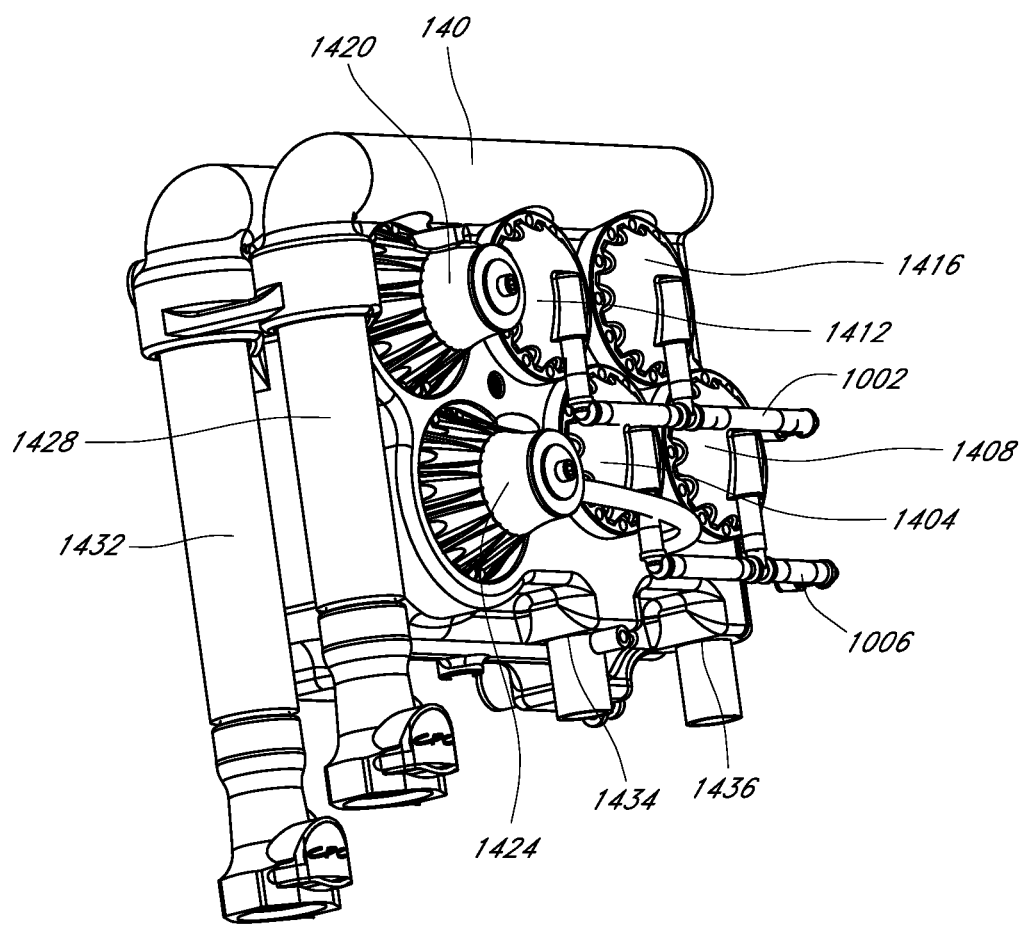
FIG. 3A illustrates an isolated perspective view of a circuit manifold with connecting parts in accordance with an example embodiment of the present disclosure.
Figure 3B:
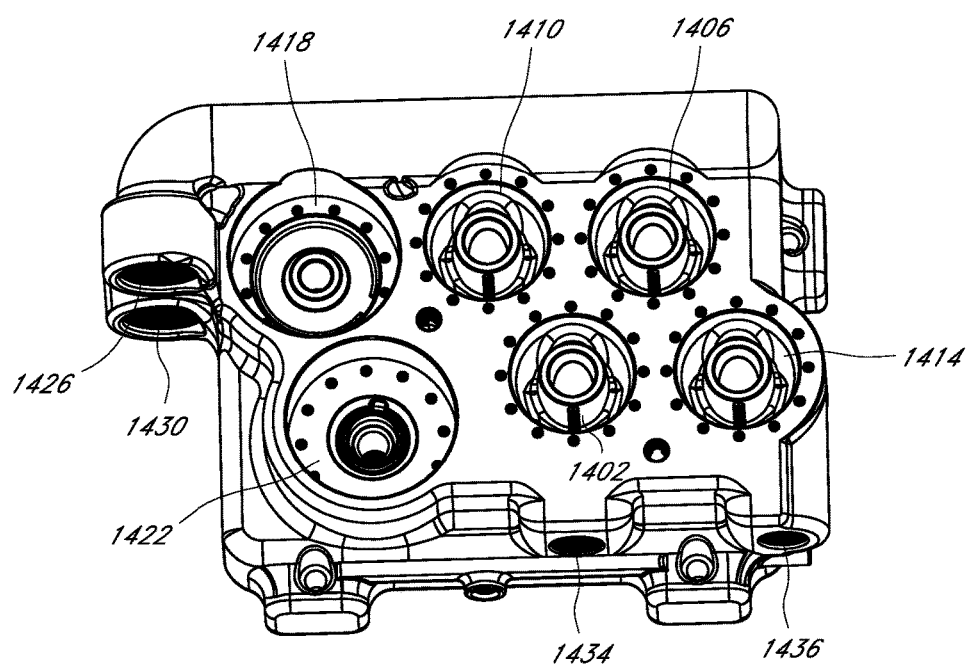
FIG. 3B illustrates a front perspective view of the circuit manifold in FIG. 3A.

An isolated perspective view of the manifold 140 with its connecting parts are shown in FIG. 3A. The manifold 140 can comprise a manifold air inlet 1426 of FIG. 3B connected to a manifold air inlet tube 1428 and a manifold air outlet 1430 connected to a manifold air outlet tube 1432. The manifold air inlet tube 1428 provides convenient connection and disconnection to any prescribed gas, such as oxygen or an anesthetic gas depending on the needs of the patient 2. The manifold air outlet tube 1432 provides quick connection and disconnection of device for containing the exhaled gasses as may be required for diagnosis or user safety.

Figure 3C:
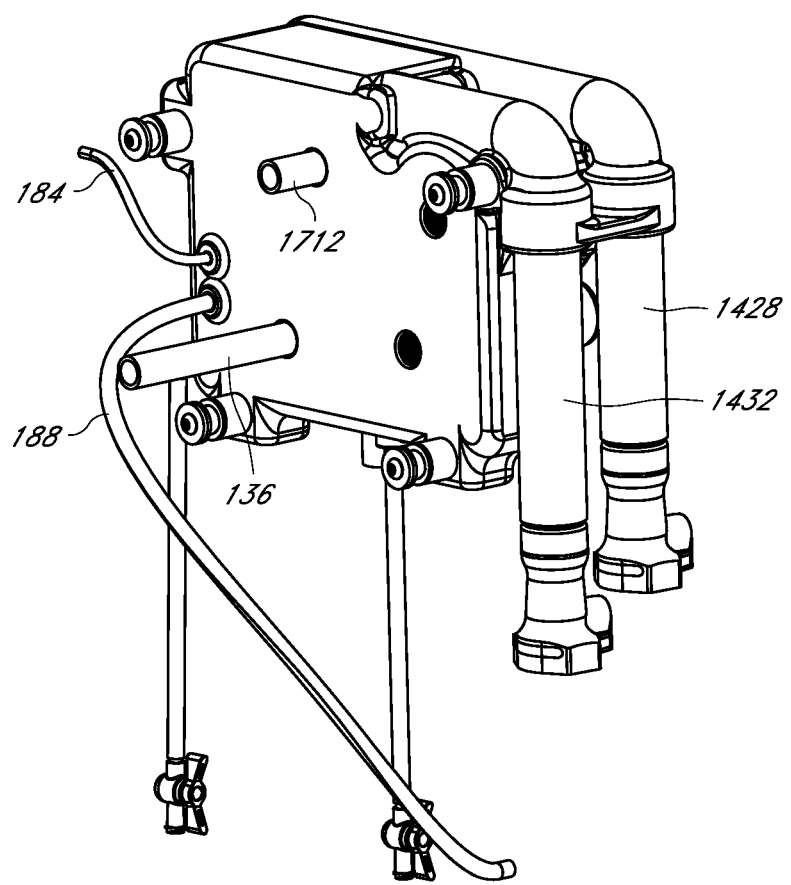
FIG. 3C illustrates back perspective view of the circuit manifold in and its connecting parts FIGS. 3A-3B.

As shown in the block diagram illustrating operations of the apparatus 1C in FIG. 1D, the manifold 140 can control gas inflow from the manifold air inlet 1426 to a breathing tube 136 of FIG. 3C, which is in fluid communication with the gas delivery port 134 of FIG. 2C and the gas delivery tube 232 to delivery gas to the patient 2. In addition, the circuit manifold 140 can connect to the canister pressure control tube 1712 to provide negative or positive pressure in the canister 160 so that the liquid 50 and gas withdrawn from the patient 2 can reenter the air-sealed canister 160 or to assistant in its delivery to the patient.

FIG. 3C also shows that the circuit manifold 140 can connect to a sensor drain and a breather drain to remove the fluid that builds up in the manifold 140. These drains prevent sensors and the diaphragm pump 190 from contacting water and the breathing liquid, such as PFC. Also as shown in FIG. 2B, an incoming line 188 and an outgoing line 184 join pneumatically in a chamber inside the manifold 140. The lines 188, 184 also serve as a liquid trap to protect pressure/vacuum sensors in the apparatus 1C. Liquid can also be trapped in an additional volume above the liquid in the canister 160 and be removed through a canister pressure control tube 1712 during the exhale phase.

Turning to the valves on the manifold 140, the manifold 140 can house four piloted pneumatic valves, a No. 9 valve 1402, a No. 15 valve 1406, a No. 16 valve 1410, a No. 17 valve 1414. The manifold 140 can also house a pressure relief valve 1418, and a vacuum relief valve 1422 (shown in FIG. 3B). The No. 17 valve 1414 is covered by a first valve cap 1416, illustrated in FIG. 3A. The No. 15 valve 1406 is covered by a second valve cap 1408. The No. 9 valve 1402 is covered by a third valve cap 1404. The No. 16 valve 1410 is covered by a fourth valve cap 1412. The pressure relief valve 1418 is covered by a pressure relief cap 1420 and the vacuum relief valve 1422 is covered by a vacuum relief cap 1424. As described above, these relief valves are optional and protect safety of the patient when abnormal $P_{aw}$ 440 is detected or when the apparatus malfunctions. The relief valves can also serve the function of enhancing reliability and portability of the device by eliminating or reducing the need for sensors or controls on a main diaphragm pump 190, which is described below. As described above, any of the relief values may be removed and over or under pressure handled with speed controls of the respective pump directly.

Figure 3D:
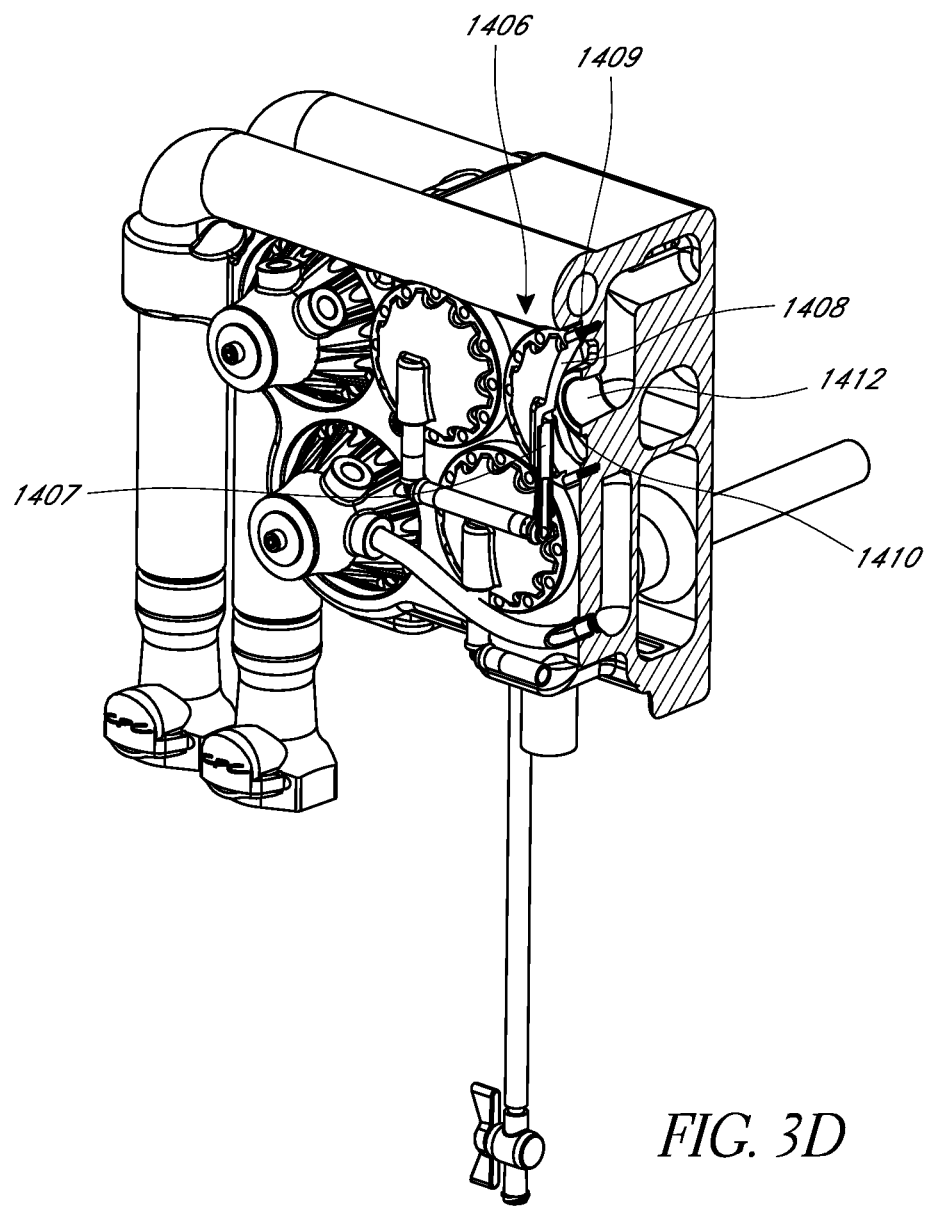
FIG. 3D illustrates a cross-section of a pneumatic piloted valve located on the circuit manifold in FIGS. 3A-3C.

FIG. 3D illustrates a cross-section of an exemplary pneumatic piloted valve, the No. 15 valve 1406. The valve 1406 comprises a diaphragm 1410, such as a thin rubber sheet, clamped between a dome 1409 and a passage 1412. When pressure is exerted downward from above 1407 the second valve cap 1408 by a pilot valve, the diaphragm 1410 is flattened to block the passage 1412, closing the No. 15 valve 1406. When vacuum is exerted downward from above 1407, the second valve cap 1416 by a pilot valve, the diaphragm 1410 is lifted up and away from the passage 1412, opening the No. 15 valve 1406.

In the illustrated embodiment, the opening and closing of the valves 1402, 1406, 1410, 1414 can cause the apparatus to switch between a pressure mode and a vacuum mode depending on whether an exhaust side of the diaphragm pump 190 goes to the atmosphere or to pressurize connected tubes, and vice versa on an vacuum side of the diaphragm pump 190 (shown I FIGS. 2B and 2D) as described above. More specifically as shown in FIG. 2C, a pressure line 1435 can connect the diaphragm pump 190 to the manifold 140 at a pressure port 1434 and a vacuum line 1437 can connect the diaphragm pump 190 to the manifold 140 at a vacuum port 1436. The No. 9 valve 1402, the No. 15 valve 1406, the No. 16 valve 1410 and the No. 17 valve 1414 on the manifold 140 are also connected to the diaphragm pump 190 and function similarly as the valves 1402B, 1406B, 1410B, 1414B in FIG. 1B so that the diaphragm pump 190 can exert a pressure in the inhale phase and a vacuum in the exhale phase.

In some embodiments, manually variable gate valves 1904 (shown FIG. 1D) are placed between the diaphragm pump 190 and the valves 1402, 1406, 1410, 1414, to control cadence of the machine via restricting flow. The opening and closing of the valves 1402, 1406, 1410, 1414, that is, the switching of the apparatus 1C between the inhale phase and the exhale phase, are in turn also controlled by the smaller pilot valves 1018, 1020, 1022, 1024 (described below). As described above and shown in FIG. 2B, the circuit manifold 140 also connects to the canister pressure control tube 1712. The pump 190 applies negative pressure in the canister 160 via the canister pressure control tube 1712 when the apparatus 1C is in the exhale phase so that the liquid 50 and gas withdrawn from the patient 2 can reenter the air-sealed canister 160 from the canister suction tube 1708. The pump 190 provides pressure to the canister 160 via the canister pressure control tube 1712 when the apparatus 1C is in the inhale phase to provide pressure in addition to that of the turbine pump 180 so that the liquid 50 can be delivered to the patient 2. The diaphragm pump 190 does not interact with the liquid 50 directly, keeping the design of the driver assembly 10 simple. The pump 190 can also lose any excess vacuum or pressure to atmosphere via the pressure and vacuum relief valves 1418, 1422 on the manifold 140 when more pressure or vacuum is produced than the patient needs. In some embodiments, the diaphragm pump 190 comprises a brushless motor to avoid fire and explosion hazards when gas removed from the lungs contain flammable gas. Sparks from a brushed motor could be a source of ignition for the flammable gas. All three pumps can be of brushless construction to prevent sparks in a flammable atmosphere. All switches in the embodiments described herein can be either electronic or of glass vacuum envelop isolated magnetic reed switch construction to prevent arching into a flammable atmosphere The diaphragm pump 190 is also connected via check valves (shown FIG. 1D) to a solenoid valve assembly 1000 comprising the valves 1018, 1020, 1022, 1024 (which are controlled by the control unit 186 and described below). In some embodiments, one or more auxiliary pumps 192, 194 (shown in FIGS. 1D, 2B and 2C) may be used. One of the boards of the control unit 186 can command the auxiliary pump 192 to shut off when a maximum control pressure is reached. Another one of the boards can command the auxiliary pump 194 to shut off when a maximum control vacuum is reached. The auxiliary pumps 192, 194 provide booster pressure in addition to a threshold pressure of the diaphragm pump 190 set by users in order to facilitate mode switching and/or positive opening/closing of the piloted valves. Specifically, the diaphragm pump 190 economically provides the bulk of pressure or vacuum to the valves 1018, 1020, 1022, 1024. The lower volume/higher pressure auxiliary pump 192 and higher pressure auxiliary pumps 194 can top off the bulk pressure/vacuum. The solenoid valve assembly 1000 is in turn connected to the caps/domes of valves 238, 1402, 1406, 1410, 1414, 2620, 2622, 2624 to control the captive diaphragms in those valves.

FIG. 1D illustrates an embodiment in which the solenoid valve assembly 1000 comprises four pairs of two-way solenoid valves. For each pair of valves, one valve receives pressure from the diaphragm pump 190 and the higher pressure auxiliary pump 192 on an input side and outputs pressure on an output side when the apparatus 1C is in the inhale phase. The other valve receives vacuum from the diaphragm pump 190 and the higher vacuum auxiliary pump 194 on the input side and outputs vacuum on the output side when the apparatus 1C is in the exhale phase.

As shown in FIG. 1D, the No. 15 valve 1406 and No. 16 valve 1410 on the manifold 140 and No. 10 valve 2620 on the patient circuit connect to an output side of a first pair of solenoid valves 1018 in the solenoid valves assembly 1000 via a first pressure/vacuum ("P/V") control line 1002 of FIG. 2C. The output side of the first pair of solenoid valves 1018 also connects to a suction pilot line 1004 ending in the circuit connection port 120 to provide pilot pressure vacuum to the No. 10 valve 2620. The suction pilot line 1004 connects to the suction pilot tube 2202 of the tube assembly 20 (in FIG. 4A) and the suction pilot tube 2202 controls the opening and closing of the suction (No. 10) valve 2620. The No. 9 valve 1402 and the No. 17 valve 1414 on the manifold 140 also connect to an output side of a second pair of solenoid valves 1020 in the solenoid valves assembly 1000 via a second P/V control line 1006. The output side of the second pair of solenoid valves 1020 also connects to a gas delivery pilot line 1008 ending in the circuit connection port 120. The gas delivery pilot line 1008 connects to the gas delivery pilot tube 2204 of the tube assembly 20 (in FIG. 4A) and the gas delivery pilot tube 2204 in turn controls the opening and closing of the gas delivery (No. 5) valve 2622. An output side of a third pair of solenoid valves 1022 on the solenoid valves assembly 1000 connects to a liquid delivery pilot line 1010 and an output side of a fourth pair of solenoid valves 1024 connects to a liquid recirculation pilot line 1012 respectively, both pilot lines also terminating at the circuit connection port 120. The liquid delivery pilot line 1010 connects to the liquid delivery pilot tube 2206 of the tube assembly 20 (in FIG. 4A) and the liquid delivery pilot tube 2206 controls the opening and closing of the liquid delivery (No. 6) valve 2624. The liquid recirculation pilot line 1012 connects to the liquid recirculation pilot tube 2208 of the tube assembly 20 (in FIG. 4A) and the liquid recirculation pilot tube 2208 controls the opening and closing of the liquid recirculation (No. 8) valve 238. The valves in the solenoid valves assembly 1000 can be 0-18V N.C. (normally closed when not energized) solenoid valves. Combination of the pairs of solenoid valves and the pneumatic valves form pilot-piloted valves, whereby energizing one of the pair of solenoid pilot valves opens their corresponding pneumatic piloted valve and energizing the other one of the pair of solenoid pilot valves closes their corresponding pneumatic piloted valves.

Figure 10A:
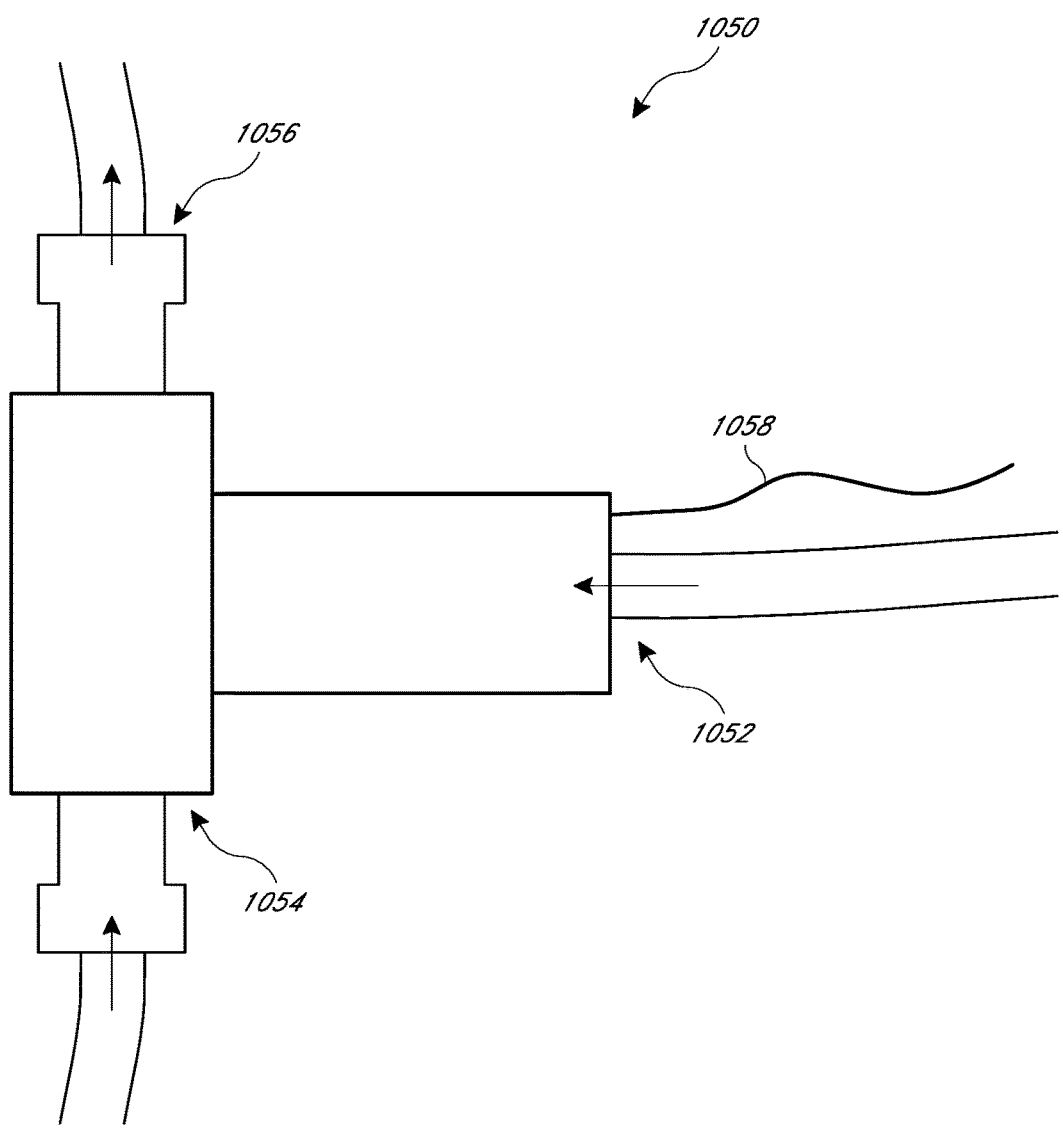
FIG. 10A is a schematic illustration of a three-way solenoid valve in accordance with an embodiment of the present disclosure.
Figure 10B:
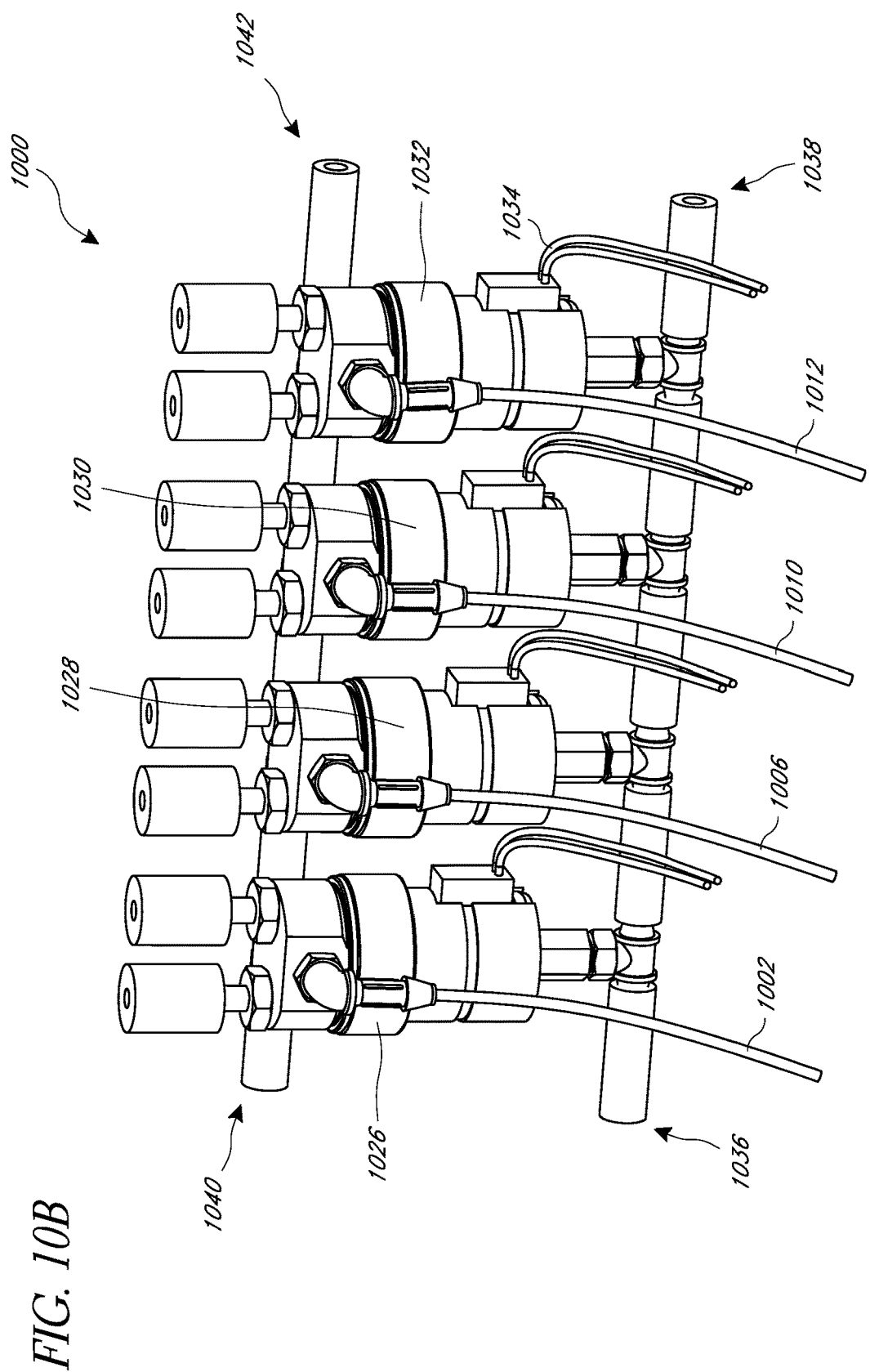
FIG. 10B illustrates a perspective view of a solenoid valve assembly comprising four three-way solenoid valves in accordance with an embodiment of the present disclosure.

In accordance with another embodiment of the present disclosure, such as shown in FIG. 2D, the solenoid valve assembly 1000 can comprise four 3-way custom-made solenoid valves instead of eight two-way solenoid valves. The 3-way solenoid valves advantageously promote portability, reliability, and economy by reduction in total parts count, lower cost per finished ventilator unit, lower power consumption, reduced volume, and reduced weight. FIG. 10A illustrate schematically a 3-way solenoid valve 1050. The 3-way solenoid valve 1050 receives pressure on a pressure inflow side 1052 when the apparatus 1C is in the inhale phase and receives vacuum on a vacuum inflow inside 1054 when the apparatus 1C is in the exhale phase. The 3-way solenoid valve 1050 output pressure or vacuum depending on the state of the apparatus 1C at an outflow side 1056. The 3-way solenoid valve 1050 receives state-switching signals from a signal wire 1058.

As shown in FIG. 2D, the diaphragm pump 190 and the auxiliary pumps 192, 194, if any, can connect to the solenoid valves assembly 1000 comprising four 3-way solenoid valves at a pressure side 1014 and an vacuum side 1016 of the solenoid valves assembly 1000. The solenoid valves assembly 1000 comprising the four 3-way solenoid valves, 1026, 1028, 1030, 1032 are more specifically shown in FIG. 10B. The 3-way solenoid valves 1026, 1028, 1030, 1032 are similar to the 3-way valve 1050 of FIG. 10A. Each valve comprises a pressure inflow side receiving pressure 1036 from the diaphragm pump 190 protected by the check valves (shown in FIG. 1D) and pressure 1038 from the pressure auxiliary pumps 192. Each valve also comprises a vacuum inflow side receiving vacuum 1040 from the diaphragm pump 190 protected by the check valves (shown in FIG. 1D) and vacuum 1042 from the vacuum auxiliary pumps 194. Each valve further comprises an outflow side providing pressure or vacuum depending on signals from signal wires 1034. More specifically, output of the first 3-way solenoid valve 1026 controls the pneumatic No. 15 valve 1406, the No. 16 valve 1410 and the suction (No. 10) valve 2620 via the first P/V control line 1002. Output of the second 3-way solenoid valve 1028 controls the pneumatic No. 9 valve 1402, the No. 17 valve 1414 and the gas delivery (No. 5) valve 2622 via the second P/V control line 1006. Output of the third 3-way solenoid valve 1030 controls the pneumatic liquid delivery (No. 6) valve 2624 via the liquid delivery pilot line 1010. Output of the fourth 3-way solenoid valve 1032 controls the pneumatic liquid recirculation (No. 8) valve 238 via the liquid recirculation pilot line 1012.

An embodiment of the present disclosure having pilot-piloted valves allow small solenoid valves to control larger pneumatically actuated valves, further reducing an overall size, power consumption, and weight of the driver assembly and making it more portable. Another advantage of this embodiment is that the first pair of 2-way solenoid valves 1018 or the first 3-way valve 1026 synchronize the opening and closing of the No. 15 valve 1406 and No. 16 valve 1410 on the manifold 140 (shown in FIG. 3B) and the suction (No. 10) valve 2620 (shown in FIG. 7A) so that the vacuum is applied to the canister 160 (shown in FIGS. 2A-2C) at the same time as to the suction tube 230 (shown in FIG. 4B) when the apparatus 1C is in the exhale phase. Likewise, the second pair of 2-way solenoid valves 1020 or the second 3-way valve 1028 synchronize the opening and closing of the No. 9 valve 1402 and the No. 17 valve 1414 on the manifold 140 (shown in FIG. 3B) and the gas delivery (No. 5) valve 2622 (shown in FIG. 7A) so that the gas flows through both the breathing tube 136 (shown in FIG. 2C) and the gas delivery tube 232 (shown in FIGS. 4A and 4C) when the apparatus 1C is in the inhale phase. In accordance with another embodiment of the present disclosure, the pressure/vacuum control tubes and lines of the apparatus 1C can be color coded or labeled to make it easy for users to perform a quick safety check to make sure that all the tubes and lines are connected correctly before using the apparatus 1C or during potential malfunctioning of the apparatus 1C.

In accordance with another embodiment of the present disclosure as described above, the valves 2620, 2622, 2624, 238 may be normally opened or closed, and therefore do not require a two state application of pressure/vacuum to control respective valves. In this case, opening and closing the valves 2620, 2622, 2624, 238 can be done by smaller pilot valves 1018, 1020, 1022, 1024. The pilot valves may define an alternative valve assembly 1000A. Each valve may be controlled by the diaphragm pump 190. When pressure is applied by the diaphragm pump 190, the higher pressure auxiliary pump 192 applies pressure on an input side, which outputs pressure on an output side. This pressure is used to close valves 2620, 2622, 2624, 238, depending on the inhale/exhale cycle. Therefore, as shown, the multiple sets of two valve controls of assembly 1000 can be replaced with multiple single valve controls having either an open or closed configuration. This alternative is illustrated in the exemplary alternative 1000A assembly in the blown out portion of FIG. 1D.

Figure 8A:
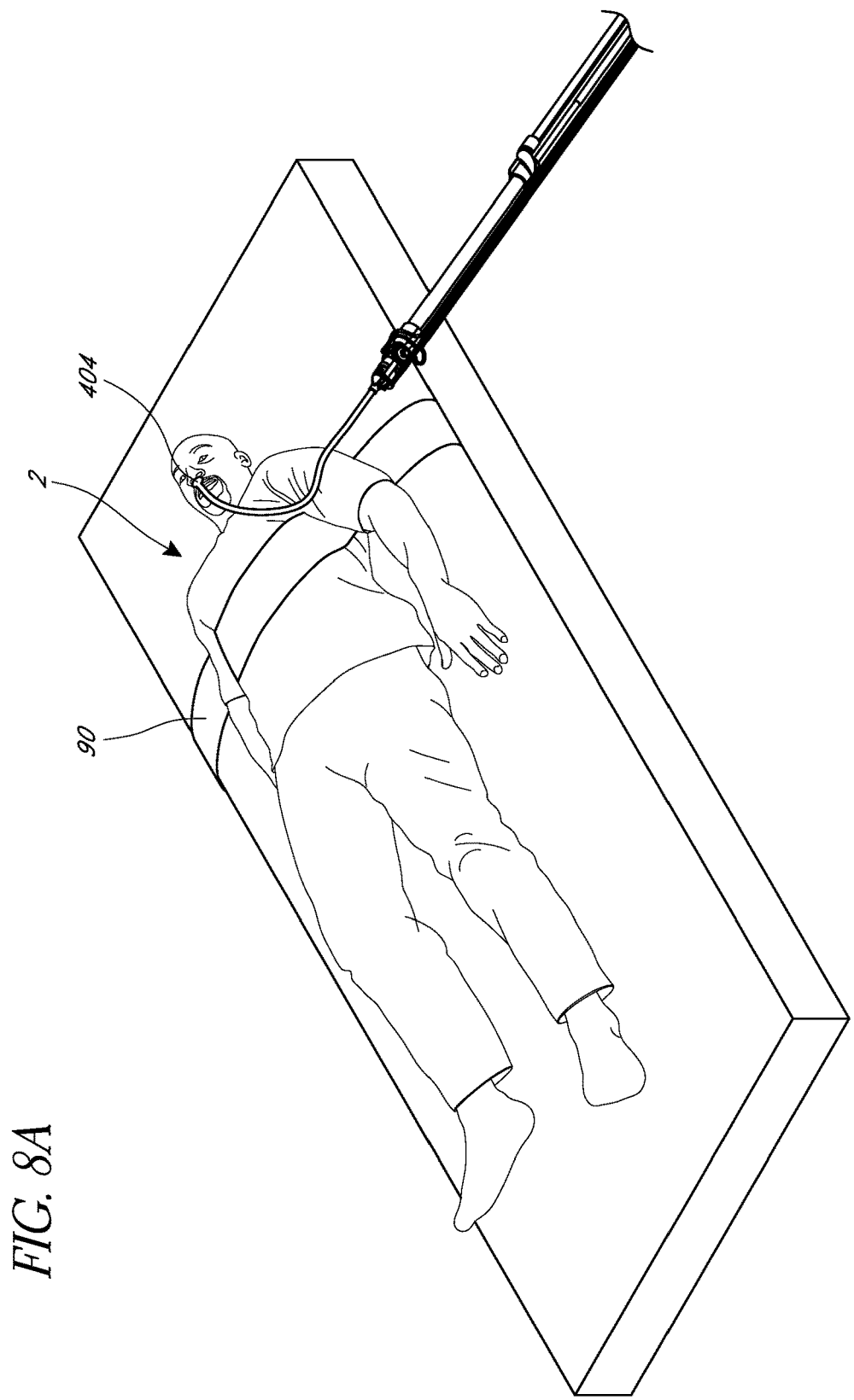
FIG. 8A illustrates a perspective view of a use of an example apparatus with an automatic CPR device on the chest of a patient in accordance with an embodiment of the present disclosure.

FIG. 8A illustrates an embodiment of use of the apparatus 1A, 1B or 1C on a patient with an automated CPR device, such as a Zoll AutoPulse® 80 or other manual or automated CPR device on the chest in accordance with an embodiment of the present disclosure. FIG. 8B is a table illustrating an example embodiment of the timing of opening and closing of all the valves on the apparatus 1A, 1B or 1C at different states of the AutoPulse® 80. For example, when an automated CPR device or a human administering CPR 80 switches to a COMPRESS state 810, the gas delivery (No. 5 valve) valve 2622, the No. 9 valve 1402 and the No. 17 valve 1414 can be closed so that no air is delivered to the patient 2. The suction (No. 10) valve 2620 can open immediately so that air or oxygen and the liquid 50 are vacuumed out of the lungs of the patient 2. On starting a RELAX cycle, the liquid delivery (No. 6) valve 2624 can have a small time delay 830 in opening and the liquid recirculation (No. 8) valve 238 can have a small time delay 830 in closing in accordance with an embodiment of the present disclosure. In one embodiment, the time delay is approximately 90 milliseconds. This time delay can be adjustable and can be used to create an initial puff of gas to precede liquid flow through to enhance alveoli performance and gas exchange based on clinical observation hence PLV. In certain embodiments, the user can adjust the time delay via the user input of the control unit. In certain embodiments, in the inhale phase, a valve in the gas delivery passage allows gas to flow an adjustable number of milliseconds (or other time interval) prior to a delayed opening of a valve in the liquid delivery passage, which in turn can shut off the valve in the gas delivery passage from back pressure or in certain embodiments the valve can be closed in response to an electronic timer. The suction phase or the inhale phase can be delayed momentarily relative to the phase of the CPR to create extra pressure or vacuum respectively in the thoracic cavity of the patient 2 during manual or automated CPR, thus increasing blood flow to the vital organs. As soon as the automated CPR device, or a human administering CPR 80 switches a RELAX state 820 and before the pressure in the patient's airway reaches the preset threshold value, the gas delivery (No. 5 valve) 2622, the liquid delivery (No. 6) valve 2624, the No. 9 valve 1402 and the No. 17 valve 1414 can be open to deliver air or oxygen and the fluid 50 to the patient 2, while the suction (No. 10) valve 2620 and the liquid recirculation (No. 8) valve 238 are closed so that flows in the suction tube 230 and the fluid recirculation tube 240 are closed. The RELAX state 820 may last for approximately 0.375 second or other length of time allowing blood flow into the chambers of the heart except optional "deep breath" parts of the cycle, or alternately a "breathe" part of the manual CPR cycle included to help oxygenate the patient. When the threshold pressure is reached in the patient's airway, the AutoPulse® 80 automatically switches back to a COMPRESS state 810 for approximately the next 0.375 second or other length of time allowing blood flow out of the chambers of the heart excepting optional "deep breath" parts of the cycle, or alternately the "breathe" part of the manual CPR cycle included to help oxygenate the patient for example by getting fresh air into the lungs. The cycle of compression states and relax states can be repeated for as long as needed. In addition, the AutoPulse® 80 is just one way of providing CPR to the patient 2. It is contemplated that compression to the patient's chest can also be achieved by other automated devices such as the "Thumper®" (Michigan Instruments Inc), manually by pulling on an inelastic adjustable band around the chest of the patient, or by any other method of increasing pressure in the heart/lungs known or obvious to one of ordinary skill in the art. One of ordinary skill in the art may contemplate from the disclosure herein other timing schedules of the AutoPulse® states or of opening and closing of the valves in the apparatus. In accordance with one embodiment of the present disclosure, separate timing of valves controlling delivery of the fluid and valves controlling delivery of air or oxygen or other gas may also be contemplated by one of ordinary skill in the art to adjust the exact proportional blend of gases and the liquid.

Figure 11:
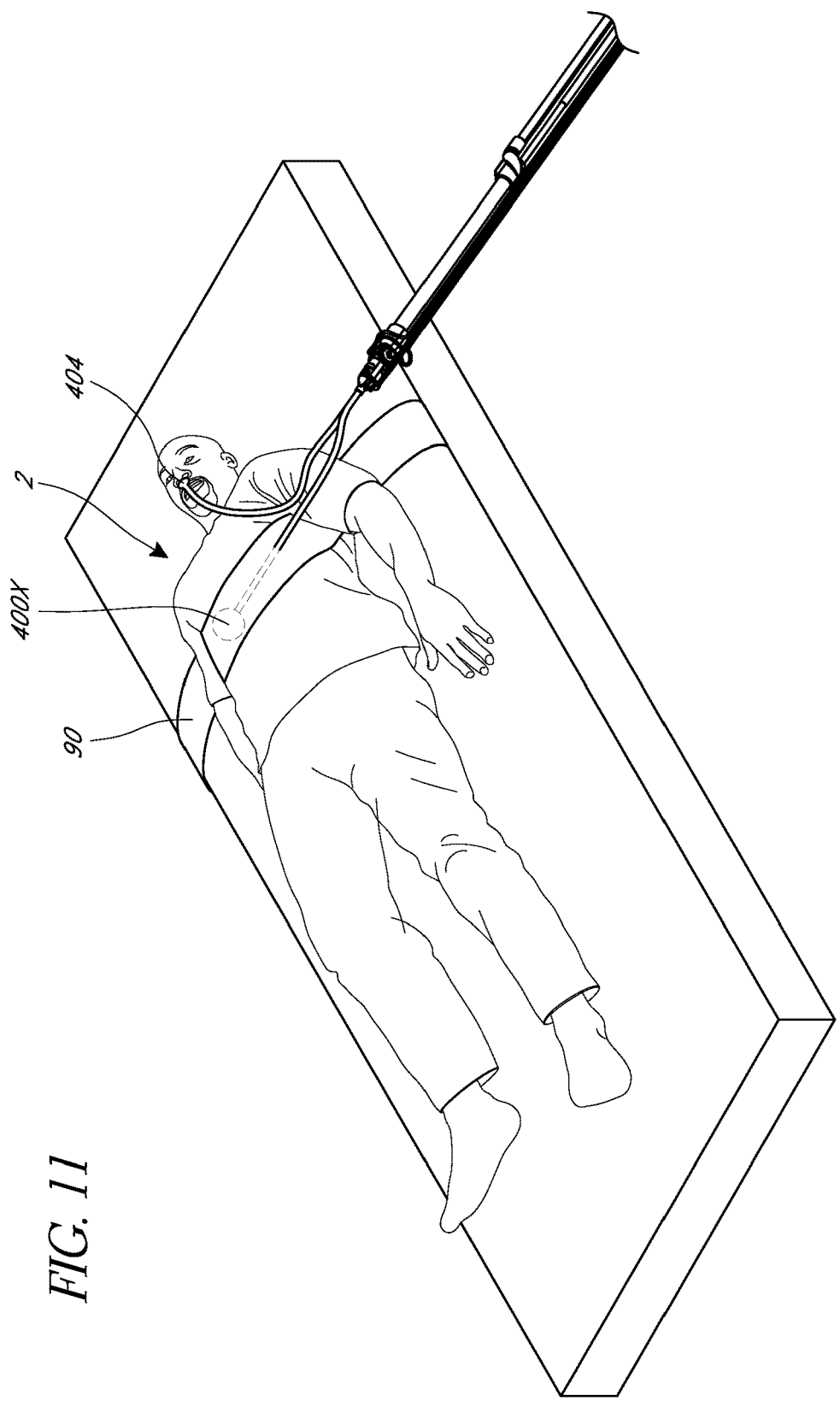
FIG. 11 is a schematic illustration of an example embodiment apparatus used in connection with an embodiment of an inelastic band.

In certain embodiments, for example, as shown in FIG. 11, the apparatus 1A, 1B, 1C can be used in combination with a band 90, which can be an inelastic and/or adjustable band (such as a belt) in certain embodiments, positioned around the patient's chest. A pressure sensor 400X can be coupled to the band, for example, placed underneath the band 90, instead of or in addition to being placed on the endotracheal tube. The band 90 can advantageously providing for an elegant method of registering pressure set points, but can also advantageously limit stretching of the lungs to prevent volutrauma. The lungs may be more susceptible to injury by over-stretching than by high pressure alone. Limiting the stretching of the lungs by the band may advantageously create a higher $P_{aw}$ that is easier for the apparatus to register. In this way, monitoring the $P_{aw}$ may permit a maximum $P_{aw}$ to safely be reached in the patient with reduced fear of potential over-inflation by over-stretching as compared to treatment without a band. This embodiment can be advantageously used on injured, premature, or diseased lungs or other anatomies that must be limited in distension. As with many features and aspects described in this disclosure, the use of a band 90 around the patient's chest can also find utility and be advantageous when used in combination with conventional gas ventilation device, and/or other apparatuses configured for ventilation, TLV and/or PLV and need not be used in combination with the features of the embodiments described herein.

In accordance with certain embodiments of the present disclosure, the embodiments of the fluid of the apparatus 1A, 1B, 1C can be cooled or heated by directly mixing the fluid with cold or hot water or other fluids. In such embodiments, the apparatus 1A, 1B, 1C does not need to include a heat exchange assembly. In such embodiments, if a hydrophobic fluid is used, the fluid and water mixture can form an emulsion which lasts for around 30 minutes. The cold or hot water may be introduced into the canister containing the fluid immediately before connecting the apparatus to a patient. Alternatively, the cold or hot water may be introduced via a connection tube coupled to the proximal end of the endotracheal tube to be mixed with the fluid before entering the lungs of the patient.

In accordance with an embodiment of the present disclosure, the apparatus comprises a driving assembly, a tube assembly and a hot water bath assembly. The hot water bath assembly provides hot water to a heat exchange assembly in the tube assembly in order to warm a liquid that is delivered to lungs of a patient.

As described above, the embodiments described above with reference to apparatus 1A, 1B, 1C can be provided with adjustable timing. That is, in certain embodiments, the user via, for example, a user interface can adjust the timing and/or duration of the inhale phase, the exhale phase, delivery of gas to lungs, and/or delivery of liquid to the lungs. The volume and/or pressure of gas and/or liquid delivered during these phases can also be adjusted by the user. This adjustability can provide several purposes and provide several advantages. For example, in certain embodiments, adjusting the delay of liquid delivery relative to gas delivery in the inhale phase can provide an elegant and robust method of varying the gas/liquid ratio provided to the patient in an apparatus that can also function as a conventional ventilator if so configured or if there is no liquid present in the reservoir. In addition, in certain embodiments, the timing of either the gas delivery and/or liquid delivery and/or extraction event (e.g., application of vacuum) can be used to enhance blood flow, particularly in the absence of an adequate or any heartbeat. For example, momentarily delaying the release of the lungs contents while pressurizing the lungs in CPR can cause a slight temporary pressure on the heart which can serve to pump blood. In a similar manner, momentarily blocking entry of fluid into the lungs in the "relax" phase of CPR can cause a momentary negative pressure on the heart can cause the heart's chambers to fill with blood to a greater volume than without such steps. Accordingly, in certain embodiments, the adjustability described above (e.g., the delay of exhale and/or inhale relative to the CPR) can be used to apply additional pressure or vacuum to enhance blood flow, particularly in the absence of adequate or any heartbeat. In certain embodiments, the apparatus 1A, 1B, 1C can include a manual override to adjust the timing and/or duration of the inhale phase, the exhale phase, delivery of gas to lungs, and/or delivery of liquid to the lungs. In certain embodiments, the apparatus 1A, 1B, 1C can adjust the timing and/or duration of the inhale phase, the exhale phase, delivery of gas to lungs, and/or delivery to liquid to the lungs based on additional signals or through a feedback loop based on for example measured pressure, tension in adjustable band 90 and/or application of pressure to a patient's chest and lungs during a cardiopulmonary resuscitation procedure.

The embodiments described above with reference to apparatus 1A, 1B, 1C can be provided with a fluid containment and/or filter for containing and/or filtering gas and/or liquid removed from the lungs of the patient. In one embodiment, the fluid containment and/or filter is connected to the apparatus by a quick disconnect and can be in communication with the suction passage.

In some embodiments, the protective cage-like frame 108 of the driver assembly 10 in FIG. 1C can be of a shape and size such that the driver assembly 10 fits snugly into an off-the-shelf ice cooler. It is contemplated that this driver assembly 10 can be cheaply and safely transported using the off-the-shelf ice cooler, for example, in the trunk of a car or an overhead cabinet of an airplane. In certain embodiments, the illustrated frame 108 of FIG. 1C can include open frame constructions, which aids the user in accessing the components within the frame 108 and/or the frame 108 can include see through panels or coverings.

Exemplary embodiments described herein may benefit from disposable components. For example, the system may be subdivided into attachable component parts such that those having patient contacting surfaces may be removed and replaced, thereby improving cleaning and/or sterility between uses. System components may also be designed to separate or otherwise be shaped or configured to improve the ability to clean and/or sterilize component parts by other methods. For example, the disclosed snorkel may have multiple versions so that it can be interchangeable such that it can be used as an exclusively wet or exclusively dry or combination of both snorkel. This component may have versions that can be disposable and replaceable between users or cleaned and/or sterilized between users. For the patient contacting surfaces, the components are preferably made of a biocompatible material or include a biocompatible coating or surface layer. The system may therefore be configured to be cleaned and sterilized in place before transport or in the field before use. The system may also be cleanable or disinfectable in the field either by accessing component parts or by replacing disposable components that may be provided in a kit for field use or components packaged together as a total system.

Exemplary embodiments may also include component parts configured to improve serviceability and accessibility of other component parts. For example, components may snap, screw, or otherwise easily be removed or separated to provide access or replacement of failed or worn parts.

Exemplary embodiments may also include internal filters to prevent bacterial or viral infection or growth of undesirable substances. Therefore, fluid lines, including gas and liquid lines may include filters, chemicals, or other mechanism to reduce bacterial or viral growth and limit a spread of infection.

Exemplary embodiments may also include apertures, windows, transparent or semi-transparent portions to visualize an interior portion of the system. For example, to track liquid levels, the reservoir could be transparent, translucent, or combinations thereof or otherwise have a port for viewing a liquid level. Other measurement mechanisms may be used such as a float gauge to monitor a liquid level within the system.

Exemplary embodiments described herein may be manufactured by use of 3D printing. A number of components described herein may not include conventional linear passages or easily machined component parts, including ports, valves, attachment portions, tubes, etc. As described herein, proximal portion of distal flow connector, or parts of the circuit manifold may be such unconventional configurations. Portions of the heat exchanger and endotracheal tube may similarly benefit therefrom.

Exemplary embodiments include an apparatus for providing liquid to a lung, comprising: a delivery device configured to deliver a fluid to the lung; a liquid delivery passage, a gas delivery passage and a suction passage, the liquid delivery, the gas delivery and the suction passages in fluid communication with the delivery device; a fluid reservoir in fluid communication with the liquid delivery passage; a vacuum source in communication with the suction passage; a gas source in communication with the gas delivery passage; a pressure sensor; a one or more valves configured to control flow through the liquid delivery, the gas delivery and/or the suction passages when the apparatus switches between an inhale phase and an exhale phase; a control unit operatively connected to the pressure sensor, mechanical force sensor, or manual switch, and the one or more valves, the control unit configured to, in response to a signal from the pressure sensor, mechanical force sensor, or manual switch, to switch the apparatus between an inhale phase in which the liquid from fluid reservoir is delivered through the liquid delivery passage and to the delivery device and/or gas can be delivered from the gas source to the gas delivery passage to the delivery device and an exhale phase in which liquid and/or gas can be withdrawn from the delivery device into the suction passage.

Exemplary embodiments may also include any combination of exemplary features. For example, the delivery device is an endotracheal tube; the pressure sensor is operatively connected to a portion of the endotracheal tube; the source of liquid in fluid communication with the liquid delivery passage comprises an oxygenated liquid; the one or more valves configured to control flow through the liquid delivery, the gas delivery and/or the suction passages when the apparatus switches between an inhale phase and an exhale phase comprise a liquid delivery valve, a gas delivery valve, and a suction valve; the liquid delivery valve, the gas delivery valve, and the suction valve are positioned within the liquid delivery, the gas delivery and the suction passages respectively; and/or the liquid delivery, the gas delivery and the suction passages are positioned within a hub that is connected to a proximal end of the delivery device.

Exemplary embodiments may also include any combination of additional features, such as, for example a tube assembly comprising a liquid delivery tube, a gas delivery tube, a suction tube, and a heat exchanger extending along a length of the tube assembly, the liquid delivery tube in fluid communication with the liquid delivery tube, the gas delivery tube in fluid communication with the gas delivery passage, the suction tube in fluid communication with the suction passage. In this case, the apparatus may also include a heat reservoir in fluid communication with the heat exchanger. The heat exchanger may comprise a liquid delivery tube and a liquid recirculation tube extending along at least a length of the tube assembly. Heated or cooled fluid may be recirculated through the liquid delivery tube and the liquid recirculation tube during inhale and exhale phases. The liquid delivery tube and the liquid recirculation tube may form a double helix. The delivery line and a return line may be formed from corrugated tubes.

Exemplary embodiments may also include the control unit configured to deliver liquid to the lungs through the delivery device only when the apparatus is in the inhale phase and to withdraw liquid from the lung through the delivery device only when the apparatus is in the exhale phase. The inhale phase may be triggered when the control unit receives a pressure signal equal to a preset vacuum or is triggered by a mechanical force sensor or manual switch and the exhale phase is triggered when the control unit receives a pressure signal equal to a threshold pressure or is triggered by a mechanical force sensor or manual switch. The control unit may include a manual override to control the inhale phase and/or exhale phase. The control unit may include a sensor that detects application of pressure or mechanical force to a patient's lungs or chest, for example, during a cardiopulmonary resuscitation procedure.

Other exemplary features that may be present in any combination include the suction passage is in fluid communication with the fluid reservoir, a recirculation tube passage in fluid communication with the liquid delivery passage and the fluid reservoir, the control unit is configured to recirculate liquid from the liquid delivery passage through the liquid recirculation tube while in the exhale phase, the one or more valves configured to control flow through the liquid, gas supply and/or suction passages when the apparatus switches between the inhale phase and an exhale phase are piloted valves, the piloted valves configured control flow through the liquid, gas supply and/or suction passages when the apparatus switches between the inhale phase and an exhale phase are connected to pilot tubes, the pilot tubes are connected to solenoid valves that are actuated by the control unit, the fluid reservoir is connected to a pump by pressure line and a vacuum line, a valve positioned in the pressure line and a valve positioned in the vacuum line, the valve positioned in the pressure line and a valve positioned in the vacuum line are formed in an integrally formed manifold, the integrally formed manifold is formed by 3D printing, in the inhale phase the valve in the pressure line is open and the valve in the vacuum line is closed and wherein in the exhale phase the valve in the pressure line is closed and the valve in the vacuum line is opened, in the inhale phase a valve in the gas delivery passage opens allowing gas to flow an adjustable amount of time prior to a delayed opening of a valve in the liquid delivery passage which in turn shuts off the valve in the gas delivery passage, the valve in the gas delivery line is closed by back pressure or by active closing, the valve positioned in the pressure line and the valve positioned in the vacuum line are piloted valves, and/or the piloted valves are controlled by a single multiport solenoid valve.

The apparatus, according to exemplary embodiments may also include a turbine pump positioned between the fluid reservoir and the liquid delivery passage. The turbine pump may be configured to aerate, with ambient air, oxygen or other gas(es), the liquid flowing between the fluid reservoir and the liquid delivery passage. The turbine pump may be configured to emulsify a second liquid into the liquid flowing between the fluid reservoir and the liquid delivery passage. The second liquid may be used to cool or heat the first liquid.

Exemplary embodiments may include adjustable timing to switch the apparatus between an inhale phase in which the liquid from the fluid reservoir is delivered through the liquid delivery passage and then to the delivery device and/or gas can be delivered from the gas source to the gas delivery passage to the delivery device and to the exhale phase in which liquid and/or gas can be withdrawn from the delivery device into the suction passage.

Exemplary embodiments include a method for partial liquid ventilation of lungs, comprising detecting a pressure in the lungs; when the pressure reaches a first value, delivering gas into the lungs and subsequently delivering a liquid to the lungs during an inhale phase; and when the pressure reaches a second value, switching to an exhale phase and withdrawing liquid and/or gas from the lungs until the pressure reaches a third value.

The method may include any combination of other exemplary steps or conditions including, for example, the first value is a preset vacuum and the second value is a threshold pressure; heating and/or cooling the liquid and/or gas before the liquid and/or gas is delivered to the lungs; heating and/or cooling the liquid and/or gas before the liquid and/or gas is delivered to the lungs comprises recirculating cool and/or warm liquid during the exhale phase through a tube assembly; delivering liquid in the inhale phase comprises delivering liquid from a fluid reservoir; during the exhale phase recirculating liquid from the fluid reservoir through a tube assembly; during exhale phase returning the withdrawn liquid to the fluid reservoir; switching from the inhale phase to the exhale phase comprising synchronized opening and closing of valves configure to control the flow of gas and/or liquid; delaying the switching from the inhale phase to exhale phase; adjusting the delay in switching from the inhale phase to exhale phase; applying cardiopulmonary resuscitation during the delay between the inhale phase to exhale phase; adjusting a timing between switching to an exhale phase and/or delivering liquid to the lungs after the pressure reaches a first value; adjusting a timing between switching to an exhale phase and/or delivering liquid to the lungs after the airway pressure reaches a first value is used to control the ratio of gas and liquid delivered to the patient; adjusting a timing between switching to an exhale phase and/or delivering liquid to the lungs after the pressure reaches a first value is used to aid pumping blood within the patient; and/or withdrawing liquid and/or gas from the lungs until the pressure reaches a third value comprises applying a vacuum.

Exemplary embodiments also include a method for partial liquid ventilation of lungs, comprising in response to detecting a patient's breathing, delivering gas into the lungs and subsequently delivering a liquid to the lungs during an inhale phase; detecting airway pressure in the lungs; and when the pressure reaches a first value, switching to an exhale phase and withdrawing liquid and/or gas from the lungs until the pressure reaches a second value.

Exemplary embodiments also include a method for partial liquid ventilation of lungs, comprising in response to an application of force to the patient's chest and resulting in the pressure to a patient's lungs during a cardiopulmonary resuscitation, delivering gas into the lungs and subsequently delivering a liquid to the lungs during an inhale phase; detecting airway pressure in the lungs; and when the pressure reaches a first value, switching to an exhale phase and withdrawing liquid and/or gas from the lungs until the pressure reaches a second value.

The exemplary methods may include any combination of additional conditions or steps, including, without limitation, the cardiopulmonary resuscitation comprises manual or automated CPR.

An exemplary embodiment includes a method for liquid ventilation of lungs, comprising aerating a liquid with a turbine pump; and delivering the aerated liquid to the lungs.

An exemplary embodiment includes a method for liquid ventilation of lungs, comprising with a turbine pump mixing a first liquid with a second liquid to create an emulsification of the first and second liquid, wherein the second liquid could be or is at a different temperature than the first liquid; and delivering the emulsification to the lungs.

An exemplary embodiment includes an apparatus for providing liquid and/or gas to a lung, comprising: a delivery device configured to deliver liquid and/or gas to the lung; a liquid delivery passage, a gas delivery passage and a suction passage, the liquid delivery, the gas delivery and the suction passages in fluid communication with the delivery device, a fluid reservoir in fluid communication with the liquid delivery passage; a vacuum source in communication with the suction passage; a gas source in communication with the gas delivery passage; and a one or more valves configured to control flow through the liquid delivery, the gas delivery and/or the suction passages when the apparatus switches between an inhale phase and an exhale phase; wherein the apparatus can be switched between a ventilation mode, a partial liquid ventilation mode and/or a total liquid ventilation mode.

An exemplary embodiment includes an apparatus for providing liquid and/or gas to a lung, comprising: one or more magnetic switches configured to prevent arcing. The exemplary embodiment may include other features, such as, for example, the apparatus is mode configured for conventional gas ventilation, total liquid ventilation and/or partial liquid ventilation and optionally can be switched between modes "on the fly" while ventilating if needed. Conventional gas ventilation mode optionally can be used "stand alone", without the intent of liquid ventilating, to extract liquid from the patient's lungs.

An exemplary embodiment includes an apparatus for providing liquid and/or gas to a lung, comprising: a gas containment and/or filter for containing and/or filtering gas and/or liquid removed from the lung. The exemplary embodiment may include any combination of features including, for example, the gas containment and/or filter is connected to the apparatus by a quick disconnect.

An exemplary embodiment includes an apparatus for providing liquid and/or gas to a lung in combination with a band configured to limit stretching of a patient's lungs.

An exemplary embodiment includes a method for ventilating a lung of a patient, comprising applying a band configured to limit stretching of a patient's lungs; and supplying ventilation to the patient. The method may include any combination of additional steps or conditions, such as, for example, providing liquid ventilation to the patient's lung; applying the band to the patient's lungs comprising limiting distention/extension of the patient anatomy.

It should be emphasized that many variations and modifications may be made to the herein-described embodiments, the elements of which are to be understood as being among other acceptable examples. All such modifications and variations are intended to be included herein within the scope of this disclosure and protected by the following claims. Moreover, any of the steps described herein can be performed simultaneously or in an order different from the steps as ordered herein. Moreover, as should be apparent, the features and attributes of the specific embodiments disclosed herein may be combined in different ways to form additional embodiments, all of which fall within the scope of the present disclosure. Specifically, embodiments described herein include systems and methods for delivering and extracting a fluid from the lungs. The fluid may include liquid, gas, and combinations thereof. Exemplary embodiments describe passages, reservoirs, tubes, canisters or other components as liquid or gas for reference purposes only. These components can be interchangeably used as would be understood by a person of skill in the art for any fluid delivery/retrieval. As such liquid passages, tubes, and reservoirs are not limited to liquid, but can also include any fluid including liquid, gas, and combinations thereof; and gas passages, tubes, and reservoirs are not limited to gas, but can also include any fluid including liquid, gas, and combinations thereof. The disclosure of specific liquid and gas combinations are exemplary only, and not intended to be limiting.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Moreover, the following terminology may have been used herein. The singular forms "a," "an," and "the" include plural referents unless the context clearly dictates otherwise. Thus, for example, reference to an item includes reference to one or more items. The term "ones" refers to one, two, or more, and generally applies to the selection of some or all of a quantity. The term "plurality" refers to two or more of an item. The term "about" or "approximately" means that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide. For example, the terms "approximately", "about", and "substantially" may refer to an amount that is within less than 10% of, within less than 5% of, within less than 1% of, within less than 0.1% of, and within less than 0.01% of the stated amount or characteristic. Numbers preceded by a term such as "about" or "approximately" also include the recited numbers. For example, "about 3.5 mm" includes "3.5 mm. For example, the disclosure expressly contemplates being able a value or range proceeded by a term such as "about" or "approximately" in this disclosure with or without such term.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "about 1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "about 1 to about 3," "about 2 to about 4" and "about 3 to about 5," "1 to 3," "2 to 4," "3 to 5," etc. As another illustration, a numerical range of "about 1 to about 5" would also include the embodiment of a range of "1 to 5." This same principle applies to ranges reciting only one numerical value (e.g., "greater than about 1") and should apply regardless of the breadth of the range or the characteristics being described. A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

What is claimed is:

1. An apparatus for providing liquid to a lung, comprising:
a delivery device configured to deliver a fluid to the lung;
a liquid delivery passage, a gas delivery passage and a suction passage, the liquid delivery, the gas delivery and the suction passages in fluid communication with the delivery device,
a fluid reservoir in fluid communication with the liquid delivery passage;
a vacuum source in communication with the suction passage;
a gas source in communication with the gas delivery passage;
a pressure sensor;
one or more valves configured to control flow through the liquid delivery, the gas delivery and the suction passages when the apparatus switches between an inhale phase and an exhale phase; and
a control unit operatively connected to the pressure sensor and the one or more valves, the control unit configured to, in response to a signal from the pressure sensor, switch the apparatus between an inhale phase in which a fluid is delivered to the delivery device by either a liquid from the fluid reservoir through the liquid delivery passage and to the delivery device or a gas from the gas source to the gas delivery passage to the delivery device and an exhale phase in which a delivered fluid is withdrawn from the delivery device into the suction passage,
wherein the fluid reservoir is connected to a pump by a pressure line and a vacuum line, and having a valve positioned in the pressure line and a valve positioned in the vacuum line, wherein the valve positioned in the pressure line and the valve positioned in the vacuum line are formed in an integrally formed manifold, and wherein in the inhale phase the valve in the pressure line is open and the valve in the vacuum line is closed and wherein in the exhale phase the valve in the pressure line is closed and the valve in the vacuum line is opened.

2. The apparatus according to claim 1, wherein the delivery device is an endotracheal tube.

3. The apparatus according to claim 2, wherein the pressure sensor is operatively connected to a portion of the endotracheal tube.

4. The apparatus according to claim 3, wherein the source of liquid in fluid communication with the liquid delivery passage comprises an oxygenated liquid.

5. The apparatus according to claim 4, wherein the one or more valves configured to control flow through the liquid delivery, the gas delivery and/or the suction passages when the apparatus switches between an inhale phase and an exhale phase comprise a liquid delivery valve, a gas delivery valve, and a suction valve, wherein the liquid delivery valve, the gas delivery valve, and the suction valve each comprise a two state valve having a diaphragm in a normally open configuration.

6. The apparatus according to claim 5, wherein the liquid delivery valve, the gas delivery valve, and the suction valve are positioned within the liquid delivery, the gas delivery and the suction passages respectively, and the liquid delivery, the gas delivery and the suction passages are positioned within a hub that is connected to a proximal end of the delivery device.

7. The apparatus according to claim 6, further comprising a tube assembly comprising a liquid delivery tube, a gas delivery tube, a suction tube, and a heat exchanger extending along a length of the tube assembly, the liquid delivery tube in fluid communication with the liquid delivery passage, the gas delivery tube in fluid communication with the gas delivery passage, the suction tube in fluid communication with the suction passage.

8. The apparatus according to claim 1, wherein the control unit is configured to deliver liquid to the lungs through the delivery device only when the apparatus is in the inhale phase and to withdraw liquid from the lung through the delivery device only when the apparatus is in the exhale phase, and the inhale phase is triggered when the control unit receives a pressure signal equal to a preset vacuum and the exhale phase is triggered when the control unit receives a pressure signal equal to a threshold pressure.

9. The apparatus according to claim 1, comprising a recirculation tube passage in fluid communication with the liquid delivery passage and the fluid reservoir, and the control unit is configured to recirculate liquid from the liquid delivery passage through the liquid recirculation tube while in the exhale phase.

10. An apparatus for providing liquid to a lung, comprising:
a delivery device configured to deliver a fluid to the lung;
a liquid delivery passage, a gas delivery passage and a suction passage, the liquid delivery, the gas delivery and the suction passages in fluid communication with the delivery device,
a fluid reservoir in fluid communication with the liquid delivery passage;
a vacuum source in communication with the suction passage;
a gas source in communication with the gas delivery passage;
a pressure sensor;
one or more valves configured to control flow through the liquid delivery, the gas delivery and the suction passages when the apparatus switches between an inhale phase and an exhale phase;

a control unit operatively connected to the pressure sensor and the one or more valves, the control unit configured to, in response to a signal from the pressure sensor, switch the apparatus between an inhale phase in which a fluid is delivered to the delivery device by either a liquid from the fluid reservoir through the liquid delivery passage and to the delivery device or a gas from the gas source to the gas delivery passage to the delivery device and an exhale phase in which a delivered fluid is withdrawn from the delivery device into the suction passage;

a tube assembly comprising a liquid delivery tube, a gas delivery tube, a suction tube, and a heat exchanger extending along a length of the tube assembly; and a heat reservoir in fluid communication with the heat exchanger, and the heat exchanger comprises a liquid delivery tube and a liquid recirculation tube extending along at least a length of the tube assembly, and heated or cooled fluid is recirculated through the liquid delivery tube and the liquid recirculation tube during inhale and exhale phases, and the liquid delivery tube and the liquid recirculation tube form a double helix.

11. The apparatus according to claim 10, wherein a delivery line and a return line are formed from corrugated tubes.

12. The apparatus according to claim 10, wherein the fluid reservoir is connected to a pump by a pressure line and a vacuum line, and having a valve positioned in the pressure line and a valve positioned in the vacuum line, wherein the valve positioned in the pressure line and the valve positioned in the vacuum line are formed in an integrally formed manifold, and wherein in the inhale phase the valve in the pressure line is open and the valve in the vacuum line is closed and wherein in the exhale phase the valve in the pressure line is closed and the valve in the vacuum line is opened.

13. An apparatus for providing liquid to a lung, comprising:

a delivery device configured to deliver a fluid to the lung;
a liquid delivery passage, a gas delivery passage and a suction passage, the liquid delivery, the gas delivery and the suction passages in fluid communication with the delivery device,
a fluid reservoir in fluid communication with the liquid delivery passage;
a vacuum source in communication with the suction passage;
a gas source in communication with the gas delivery passage;
a pressure sensor;
one or more valves configured to control flow through the liquid delivery, the gas delivery and the suction passages when the apparatus switches between an inhale phase and an exhale phase; and
a control unit operatively connected to the pressure sensor and the one or more valves, the control unit configured to, in response to a signal from the pressure sensor, switch the apparatus between an inhale phase in which a fluid is delivered to the delivery device by either a liquid from the fluid reservoir through the liquid delivery passage and to the delivery device or a gas from the gas source to the gas delivery passage to the delivery device and an exhale phase in which a delivered fluid is withdrawn from the delivery device into the suction passage, wherein in the inhale phase a valve in the gas delivery passage opens allowing gas to flow an adjustable amount of time prior to a delayed opening of a valve in the liquid delivery passage which in turn shuts off the valve in the gas delivery passage.

14. An apparatus for providing liquid to a lung, comprising:

a delivery device configured to deliver a fluid to the lung;
a liquid delivery passage, a gas delivery passage and a suction passage, the liquid delivery, the gas delivery and the suction passages in fluid communication with the delivery device,
a fluid reservoir in fluid communication with the liquid delivery passage;
a vacuum source in communication with the suction passage;
a gas source in communication with the gas delivery passage;
a pressure sensor;
one or more valves configured to control flow through the liquid delivery, the gas delivery and the suction passages when the apparatus switches between an inhale phase and an exhale phase;
a control unit operatively connected to the pressure sensor and the one or more valves, the control unit configured to, in response to a signal from the pressure sensor, switch the apparatus between an inhale phase in which a fluid is delivered to the delivery device by either a liquid from the fluid reservoir through the liquid delivery passage and to the delivery device or a gas from the gas source to the gas delivery passage to the delivery device and an exhale phase in which a delivered fluid is withdrawn from the delivery device into the suction passage; and
a turbine pump positioned between the fluid reservoir and the liquid delivery passage, wherein the turbine pump is configured to aerate liquid flowing between the fluid reservoir and the liquid delivery passage.

15. An apparatus for providing liquid to a lung, comprising:

a delivery device configured to deliver a fluid to the lung;
a liquid delivery passage, a gas delivery passage and a suction passage, the liquid delivery, the gas delivery and the suction passages in fluid communication with the delivery device,
a fluid reservoir in fluid communication with the liquid delivery passage;
a vacuum source in communication with the suction passage;
a gas source in communication with the gas delivery passage;
a pressure sensor;
one or more valves configured to control flow through the liquid delivery, the gas delivery and the suction passages when the apparatus switches between an inhale phase and an exhale phase;
a control unit operatively connected to the pressure sensor and the one or more valves, the control unit configured to, in response to a signal from the pressure sensor, switch the apparatus between an inhale phase in which a fluid is delivered to the delivery device by either a liquid from the fluid reservoir through the liquid delivery passage and to the delivery device or a gas from the gas source to the gas delivery passage to the delivery device and an exhale phase in which a delivered fluid is withdrawn from the delivery device into the suction passage; and a turbine pump positioned between the fluid reservoir and the liquid delivery passage, wherein the turbine pump is configured to emulsify a second liquid into the liquid flowing between the fluid reservoir and the liquid delivery passage, wherein the second liquid cools or heats the first liquid.

16. A method for partial liquid ventilation of lungs, comprising detecting a pressure in the lungs;

when the pressure reaches a first value, delivering gas into the lungs and subsequently delivering a liquid to the lungs during an inhale phase, the delivered gas or the liquid defining a delivered fluid;

when the pressure reaches a second value, switching to an exhale phase and withdrawing the delivered fluid from the lungs until the pressure reaches a third value; and adjusting a timing between switching to an exhale phase and delivering liquid to the lungs after the pressure reaches the first value wherein adjusting the timing between switching to an exhale phase and delivering liquid to the lungs after the pressure reaches the first value is used to control the ratio of gas and liquid delivered to the patient.

17. The method according to claim 16, wherein the first value is a preset vacuum and the second value is a threshold pressure.

18. The method according to claim 16, comprising changing a temperature of the delivered fluid to the lungs before the fluid is delivered to the lungs.

19. The method according to claim 16, wherein the changing the temperature of the fluid delivered to the lungs comprises recirculating the liquid during the exhale through a tube assembly.

20. The method according to claim 16, wherein withdrawing the fluid from the lungs until the pressure reaches a third value comprises applying a vacuum.

* * * * *